(12) United States Patent
Krishnan et al.

(10) Patent No.: US 7,956,160 B2
(45) Date of Patent: Jun. 7, 2011

(54) CONCENTRATED PROTEIN LYOPHILATES, METHODS, AND USES

(75) Inventors: Sampathkumar Krishnan, Camarillo, CA (US); Monica Pallitto, Bellevue, WA (US); Margaret Ricci, Camarillo, CA (US); Wenjin Cao, Simi Valley, CA (US); Hong Lin, Westlake Village, CA (US); Yong Xie, Thousand Oaks, CA (US); Samantha Nagle, Dupont, WA (US); Shon Lee Crampton, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 553 days.

(21) Appl. No.: 11/996,420

(22) PCT Filed: Jul. 20, 2006

(86) PCT No.: PCT/US2006/028476
§ 371 (c)(1),
(2), (4) Date: Jan. 22, 2008

(87) PCT Pub. No.: WO2007/014073
PCT Pub. Date: Feb. 1, 2007

(65) Prior Publication Data
US 2008/0213215 A1 Sep. 4, 2008

Related U.S. Application Data

(60) Provisional application No. 60/702,025, filed on Jul. 22, 2005.

(51) Int. Cl.
*A61K 38/16* (2006.01)
*A61K 39/395* (2006.01)
*C07K 14/00* (2006.01)
*C07K 16/00* (2006.01)
*C07K 19/00* (2006.01)

(52) U.S. Cl. .............. 530/350; 424/130.1; 424/133.1; 424/134.1; 424/499; 514/1.1; 514/777; 530/387.1; 530/387.3

(58) Field of Classification Search .............. None
See application file for complete search history.

(56) References Cited

U.S. PATENT DOCUMENTS

| | | | |
|---|---|---|---|
| 6,180,355 | B1 | 1/2001 | Alexander |
| 6,284,282 | B1 | 9/2001 | Maa et al. |
| 6,821,515 | B1 | 11/2004 | Cleland et al. |
| 2002/0136719 | A1 | 9/2002 | Shenoy et al. |
| 2003/0026813 | A1 | 2/2003 | Gallili et al. |
| 2004/0219224 | A1 | 11/2004 | Yakovlevsky et al. |
| 2005/0220786 | A1 | 10/2005 | Mahler |
| 2007/0196364 | A1* | 8/2007 | Krishnamurthy et al. . 424/133.1 |
| 2008/0213215 | A1* | 9/2008 | Krishnan et al. ............ 424/85.2 |

FOREIGN PATENT DOCUMENTS

| | | | |
|---|---|---|---|
| WO | WO 03/053465 A2 | | 7/2003 |
| WO | WO 2006/014965 | * | 2/2006 |
| WO | WO 2006/042240 A2 | | 4/2006 |
| WO | WO 2006/138181 A2 | | 12/2006 |
| WO | WO 2007/005612 A2 | | 1/2007 |

OTHER PUBLICATIONS

Hawe et al, Europ. Jour. Pharma. Sci., 28, 224-232, 2006.*
Johnson et al, Jour. Pharma. Sci., 91, 914-922, 2002.*
Pyne et al, Jour. Pharma. Sci., 92, 2272-2283, 2003.*
Economides, A.N., et al., "Cytokine traps: multi-component high-affinity blockers of cytokine action", Nature Medicine, Jan. 2003, vol. 9, No. 1, pp. 47-52.

\* cited by examiner

*Primary Examiner* — David A Saunders

(57) ABSTRACT

The invention provides, among other things, lyophilized compositions of high surface area that comprise a protein and that reconstitute quickly and efficiently to solution of high protein concentration with minimal formation, if any, of foam, effervescence, bubbles, turbidity, or particulates that might be deleterious. The invention also provides, among other things, methods for making the lyophilized compositions. The invention in additional aspects also provides Raman Imaging Spectrographic methods for real time analyses of polymorphs in a sample using PLS algorithms. By way of particular example, the use of the method for the analysis of mannitol polymorphs is described, and the use of the analysis to determine optimum compositions and lyophilization methods for producing lyophilates of pharmaceutical proteins having a predefined distribution of mannitol polymorphs and having the aforementioned reconstitution properties is also described.

16 Claims, 7 Drawing Sheets

CONCENTRATED PROTEIN LYOPHILATES, METHODS, AND USES

REFERENCE TO RELATED APPLICATIONS

This application claims the benefit of U.S. Provisional Application Ser. No. 60/702,025 filed 22 Jul. 2005, which is incorporated herein by reference in its entirety.

FIELD OF THE INVENTION

The invention relates to, among other things, high surface area lyophilates that comprise at least one protein and that reconstitute quickly upon addition of diluent to provide solutions of high protein concentrations, with reduced formation of foam, effervescence, bubbles, aggregates, and particulates, among others. The invention also relates to, among other things, lyophilization methods for making such lyophilates. Among preferred compositions, and methods for making the same, are pharmaceutical compositions suitable for administration to human patients for the treatment of disease.

BACKGROUND OF THE INVENTION

Recombinant DNA methods developed since the late 1970s are now commonly employed as the primary means for producing pharmaceutical proteins for veterinary and human use. While recombinant methods have overcome many if not most of the challenges of producing these proteins, there are still problems to overcome regarding their formulation and administration.

Generally, proteins are thoroughly degraded by digestive processes and, as a rule, cannot be administered orally. They also generally are too large for transdermal administration. Furthermore, while many proteins can be prepared as liquid formulations, some at fairly high concentration, they are prone in the liquid state to physical and/or chemical degradation. In particular, aggregation is common in high concentration liquid protein formulations. Lyophilized formulations typically are much more stable. They do not undergo the degradation or aggregation that occurs in liquid formulations. Or if they do, the degradation or loss of protein activity occurs at a very much slower rate. However, it has been difficult or not possible to produce stable lyophilates of many therapeutic proteins that can be reconstituted in the concentrations necessary for therapeutic efficacy.

The problems associated with the formulation of protein therapeutics are especially challenging where high concentrations are desired, as in, for instance, formulations for subcutaneous administration. In fact, many proteins cannot be stably formulated in solution as high concentrations. And, even when proteins can be formulated, at least initially to high concentrations, often the formulations suffer from a variety of undesirable characteristics, such as poor shelf-life, poor or unreliable reconstitution, and unacceptable turbidity, foam, or bubbles upon reconstitution. As a result many protein therapeutics that might be advantageously administered subcutaneously have to be administered intravenously instead. Such problems are characteristic not only of proteins formulated entirely in liquid form, but also of proteins that have been lyophilized and must subsequently be reconstituted into a liquid form for administration.

Clearly there is a need for methods to produce and formulate protein therapeutic agents as stable lyophilates. In particular, there is a need for lyophilates that can be reconstituted to provide high concentration formulations. And in this regard, there is a need for lyophilates that can be reconstituted to high protein concentration formulations suitable for SC injection. One of the main obstacles to achieving such formulations is producing a purified, stable composition that can be reconstituted at the point of care in the high protein concentrations necessary for effective dosing via SC administration.

Obstacles to obtaining such formulations include: (i) uncontrolled and unpredictable protein instability during processing and storage, and loss of activity caused thereby; (ii) excessively long reconstitution times; (iii) unpredictable and uncontrolled formation of aggregates that deleteriously affect activity or result in unacceptable turbidity; (iv) foaming on reconstitution that decreases unit activity or is aesthetically unacceptable to users; (v) bubbling and effervescence that cause denaturation and decrease activity or are unacceptable to users; (vi) bubble entrapment that interferes with proper dosing; (vii) residual particulates that reduce recovery and dosing and/or are unacceptable to users; (viii) high viscosity that makes it difficult to properly load syringes for administration; and (ix) other uncontrollable deleterious alterations to bioactivity, bioavailability, reliability of dosing, or acceptability of dosing, that result from the formulation and reconstitution method.

Shire et al. have reviewed the opportunities and challenges of high concentration protein formulation in their review article, "Challenges in the Development of High Protein Concentration Formulations," J. Pharm. Sci. 93(6): 1390-1402 (June 2004). Several workers have described approaches for improving highly concentrated protein formulations. Roser, in U.S. Pat. No. 4,891,319, describes the use of 0.05 and 25 weight percent trehalose to protect proteins against denaturation during drying. While the trehalose reduces loss of activity under some drying regimes, it does not solve many other of the aforementioned problems. Andya and co-workers, in U.S. Pat. No. 6,685,940, describe an antibody lyophilate made with a non-reducing sugar and histidine and antibody/sugar mole ratio of 100 to 600. Reportedly, the lyophilate could be reconstituted to an isotonic solution containing from 50 to 400 mg/ml antibody. Andya's process requires only one drying step, and often may not produce satisfactory results. While this has apparently proven effective for some antibodies, it has not proven to be generally applicable, and it does not overcome all of the aforementioned problems.

Rapp and Grandgeorge, in US Application Publication No. 2004/0005310 A1, describe methods for reconstituting lyophilized proteins under gas pressure between 1 mbar and atmospheric pressure, which are particularly suitable for blood coagulation proteins. The methods appear to advance the art marginally for some proteins. In particular, the innovation does not appear to be widely applicable and probably is not suitable for patient self-administration.

Thus, despite these and other improvements, there remains a need for improved methods for preparing and formulating highly concentrated proteins and for high concentration protein preparations that have a long shelf life, are stable under relatively unfavorable conditions (that may be encountered during shipping, storage, and use), can be reliably reconstituted, and conveniently administered in form and manner entirely acceptable to a wide variety of users. In particular, there is a need for reliable methods for formulating protein therapeutics in a manner that preserves activity, provides adequate stability to allow long-term storage, and provides reliable formulation at the point of care for high concentration protein formulations suitable for subcutaneous administration.

SUMMARY

It is therefore among the objects of the present invention to provide in certain of its preferred aspects and preferred embodiments each and all of the following. The numbered paragraphs below are self-referential. In particular, the phase "in accordance with any of the foregoing or the following" used in these paragraphs refers to the other paragraphs in the Summary. The phase also means in the following paragraphs that the invention encompasses in various embodiments not only the subject matter described in the individual paragraphs but also the subject matter described by the paragraphs taken in combination. In this regard, it is explicitly applicant's purpose in setting forth the following paragraphs to describe various aspects and embodiments of the invention particularly by the paragraphs taken in combination. Similarly, various aspects and embodiments of the invention relate to specific entries in lists of values provided in the paragraphs below, which are recited in list format rather than individually solely for purposes of brevity. Applicant specifically reserves the right to claim any of the subject matter set out in the following paragraphs, taking the paragraphs alone or in any combination and including one or more (if any) of the values listed therein below.

1. A lyophilate, in certain embodiments a pharmaceutical lyophilate, comprising a protein, wherein within any of 1 or less, 2 or less, 3 or less, 4 or less, or 5 or less minutes after adding a diluent to the lyophilate, a solution is formed, said solution being characterized by any one or more of the following, taken in any combination:
   (a) the lyophilate is any of at least 90, 92, 95, 97, 98, or 99%+/−5 or +/−10% dissolved therein;
   (b) the concentration of the protein in the solution is any of at least 25, 30, 35, 40, 50, 55, 65, 75, 85, 90, 95, 100, 110, 115, 120, 125, 130, 140, 150, 160, 175, 200, 225, 250, or 300 mg/ml;
   (c) the height of foam above the solution is less than any of 5%, 10%, 15%, 20%, 25%, 30%, or 35% of the height of the foam above the solution plus the height of the solution;
   (d) there is in the solution, any one or more of: no visible effervescence, no visible turbidity, no visible bubble and/or no visible particles.

2. A lyophilate, in certain embodiments a pharmaceutical lyophilate, in accordance with any of the foregoing or the following, wherein the foam height is measured under even illumination having an intensity at the sample of approximately 2,000 Lux using non-glare black and white backgrounds, and heights are measured using calipers.

3. A lyophilate, in certain embodiments a pharmaceutical lyophilate, in accordance with any of the foregoing or the following, wherein the composition is gently swirled during or up to three minutes after addition of the diluent.

4. A lyophilate, in certain embodiments a pharmaceutical lyophilate, in accordance with any of the foregoing or the following, wherein the presence of any one or more of: visible effervescence, visible turbidity, visible bubbles, and/or visible particles is determined by observation under even illumination having an intensity at the sample of approximately 2,000 Lux using non-glare black and white backgrounds.

5. A lyophilate, in certain embodiments a pharmaceutical lyophilate, in accordance with any of the foregoing or the following, comprising a protein and having a surface area that is equal to or greater than any of approximately 1.0, 1.1, 1.2, 1.3, or 1.4 $m^2/gm$.

6. A lyophilate, in certain embodiments a pharmaceutical lyophilate, in accordance with any of the foregoing or the following, comprising a protein and having a surface area that is equal to or greater than any of 1.0, 1.1, 1.2, 1.3, or 1.4 $m^2/gm$; in certain particular embodiments greater than 1.0 $m^2/gm$, and in certain particular embodiments greater than 1.2 $m^2/gm$.

7. A lyophilate, in certain embodiments a pharmaceutical lyophilate, in accordance with any of the foregoing or the following, comprising a protein and having a surface area that is equal to or greater than any of approximately 1.0, 1.1, 1.2, 1.3, or 1.4 $m^2/gm$ and equal to or less than any of approximately 1.5, 1.7, 2.0, 2.5, 3.0, 4.0, or 5.0 $m^2/gm$.

8. A lyophilate, in certain embodiments a pharmaceutical lyophilate, in accordance with any of the foregoing or the following, comprising a protein and having a surface area that is equal to or greater than any 1.0, 1.1, 1.2, 1.3, or 1.4 $m^2/gm$ and equal to or less than any of 1.5, 1.7, 2.0, 2.5, 3.0, 4.0, or 5.0 $m^2/gm$.

9. A lyophilate, in certain embodiments a pharmaceutical lyophilate, in accordance with any of the foregoing or the following, comprising a protein and having a surface area that is equal to or greater than approximately 1.0 $m^2/gm$.

10. A lyophilate, in certain embodiments a pharmaceutical lyophilate, in accordance with any of the foregoing or the following, comprising a protein and having a surface area that is equal to or greater than approximately 1.2 $m^2/gm$.

11. A lyophilate, in certain embodiments a pharmaceutical lyophilate, in accordance with any of the foregoing or the following, comprising a protein and having a surface area that is equal to or greater than 1.0 $m^2/gm$.

12. A lyophilate, in certain embodiments a pharmaceutical lyophilate, in accordance with any of the foregoing or the following, comprising a protein and having a surface area that is equal to or greater than 1.2 $m^2/gm$.

13. A lyophilate, in certain embodiments a pharmaceutical lyophilate, in accordance with any of the foregoing or the following, comprising a protein and mannitol wherein the mannitol therein is equal to or greater than approximately 70% delta mannitol, equal to or less than approximately 20% mannitol hydrate, and equal to or less than approximately 10% amorphous mannitol.

14. A lyophilate, in certain embodiments a pharmaceutical lyophilate, in accordance with any of the foregoing or the following, comprising a protein and mannitol wherein the mannitol therein is equal to or greater than approximately 70% delta mannitol, equal to or less than approximately 10% amorphous mannitol, and the sum of mannitol hydrate, alpha mannitol, and beta mannitol is equal to or less than approximately 20%.

15. A lyophilate, in certain embodiments a pharmaceutical lyophilate, in accordance with any of the foregoing or the following, comprising a protein and mannitol wherein the mannitol therein is equal to or greater than 70% delta mannitol, equal to or less than 20% mannitol hydrate, and equal to or less than 10% amorphous mannitol.

16. A lyophilate, in certain embodiments a pharmaceutical lyophilate, in accordance with any of the foregoing or the following, comprising a protein and mannitol wherein the mannitol therein is equal to or greater than 70% delta mannitol, equal to or less than 10% amorphous mannitol, and the sum of mannitol hydrate, alpha mannitol, and beta mannitol is equal to or less than 20%.

17. A lyophilate, in certain embodiments a pharmaceutical lyophilate, in accordance with any of the foregoing or the following, wherein addition of diluent results in a solution with a protein concentration of at least approximately 40, 45, 50, 60 75, 90, 100, or 150 mg/ml.

18. A lyophilate, in certain embodiments a pharmaceutical lyophilate, in accordance with any of the foregoing or the following, wherein addition of diluent results in a solution with a protein concentration of at least 40, 45, 50, 60 75, 90, 100, or 150 mg/ml.

19. A lyophilate, in certain embodiments a pharmaceutical lyophilate, in accordance with any of the foregoing or the following, wherein addition of diluent results in a solution with a protein concentration of approximately 40 to 250, 40 to 200, 75 to 150, or 50 to 100 mg/ml.

20. A lyophilate, in certain embodiments a pharmaceutical lyophilate, in accordance with any of the foregoing or the following, wherein addition of diluent results in a solution with a protein concentration of 40 to 250, 40 to 200, 75 to 150, or 50 to 100 mg/ml.

21. A lyophilate, in certain embodiments a pharmaceutical lyophilate, in accordance with any of the foregoing or the following, wherein the protein is at least approximately any of 85, 90, 95, 97, 98, or 99% stable for at least any of approximately 3, 4, 5, 6, 9, 12, 18, or 24 months storage at any of approximately 4, 21, or 37° C., including any combination of the foregoing percents, months of storage, and storage temperatures.

22. A lyophilate, in certain embodiments a pharmaceutical lyophilate, in accordance with any of the foregoing or the following, wherein the percentage stability is determined relative to the amount of intact protein in the lyophilate when storage is initiated.

23. A lyophilate, in certain embodiments a pharmaceutical lyophilate, in accordance with any of the foregoing or the following, wherein the protein is at least any of 85, 90, 95, 97, 98, or 99% stable for at least any of 3, 4, 5, 6, 9, 12, 18, or 24 months storage at any of 4, 21, or 37° C., including any combination of the foregoing percents, months of storage, and storage temperatures.

24. A lyophilate, in certain embodiments a pharmaceutical lyophilate, in accordance with any of the foregoing or the following, wherein stability is measured by the ratio of the amounts(s) of one or more "native peak(s)" representative of the intact protein to the total amount of protein present (as indicated by the native peaks plus all other peaks of the protein).

25. A lyophilate, in certain embodiments a pharmaceutical lyophilate, in accordance with any of the foregoing or the following, wherein stability is measured by SE-HPLC.

26. A lyophilate, in certain embodiments a pharmaceutical lyophilate, in accordance with any of the foregoing or the following, wherein the solution flows easily.

27. A lyophilate, in certain embodiments a pharmaceutical lyophilate, in accordance with any of the foregoing or the following, wherein the resulting solution is of sufficiently low viscosity to flow efficiently through a hypodermic needle of a gauge effective for subcutaneous injection into a human subject.

28. A lyophilate, in certain embodiments a pharmaceutical lyophilate, in accordance with any of the foregoing or the following, wherein the viscosity of the resulting solution is any one of below 10, 15, 20, 25, 30, 35, 40, 45, 50, 55, 60, 65, 70, 75, 80, 90, or 100 cP, in particular embodiments below 50 cP, in certain embodiments below 25 cP, in various embodiments below 10 cP.

29. A lyophilate, in certain embodiments a pharmaceutical lyophilate, in accordance with any of the foregoing or the following, wherein the diluent is degassed before addition to the lyophilate.

30. A lyophilate, in certain embodiments a pharmaceutical lyophilate, in accordance with any of the foregoing or the following, comprising at least one of any one or more of the following: a bulking agent, a stabilizing agent, a lyoprotectant, and/or a surfactant.

31. A lyophilate, in certain embodiments a pharmaceutical lyophilate, in accordance with any of the foregoing or the following, comprising mannitol.

32. A lyophilate, in certain embodiments a pharmaceutical lyophilate, in accordance with any of the foregoing or the following, comprising any of 2.0, 2.5, 3.0, 3.5, or 4.0% mannitol.

33. A lyophilate, in certain embodiments a pharmaceutical lyophilate, in accordance with any of the foregoing or the following, comprising 2.0 to 4.0% mannitol.

34. A lyophilate, in certain embodiments a pharmaceutical lyophilate, in accordance with any of the foregoing or the following, comprising sucrose.

35. A lyophilate, in certain embodiments a pharmaceutical lyophilate, in accordance with any of the foregoing or the following, comprising 0.5, 1.0, 1.5, 2.0, or 2.5% sucrose.

36. A lyophilate, in certain embodiments a pharmaceutical lyophilate, in accordance with any of the foregoing or the following, comprising 1.0 to 2.0% sucrose.

37. A lyophilate, in certain embodiments a pharmaceutical lyophilate, in accordance with any of the foregoing or the following, comprising a surfactant.

38. A lyophilate, in certain embodiments a pharmaceutical lyophilate, in accordance with any of the foregoing or the following, comprising one or more of a polysorbate and Pluronic F68.

39. A lyophilate, in certain embodiments a pharmaceutical lyophilate, in accordance with any of the foregoing or the following, comprising a polysorbate 80 or a polysorbate 20 in a concentration from 0.004% to 0.15%, and/or Pluronic F68 in a concentration from 0.05% to 1.5%.

40. A lyophilate, in certain embodiments a pharmaceutical lyophilate, in accordance with any of the foregoing or the following, wherein the protein is an agent for human therapeutic use or for veterinary use or for both.

41. A lyophilate, in certain embodiments a pharmaceutical lyophilate, in accordance with any of the foregoing or the following, wherein the protein is an agent for human therapeutic use or for veterinary use or for both and the lyophilate is suitable for human therapeutic use or for veterinary use or for both.

42. A lyophilate, in certain embodiments a pharmaceutical lyophilate, in accordance with any of the foregoing or the following, wherein the protein is a pharmaceutical agent for human therapeutic use, and the lyophilate is suitable for human therapeutic use.

43. A lyophilate, in certain embodiments a pharmaceutical lyophilate, in accordance with any of the foregoing or the following, wherein the solution is suitable for subcutaneous administration to a human subject.

44. A lyophilate, in certain embodiments a pharmaceutical lyophilate, in accordance with any of the foregoing or the following, wherein the composition is disposed in a sterile container under vacuum, the diluent is sterile and degassed, and the resulting solution is sterile, is suitable for administration to a human subject by subcutaneous injection, and is of sufficiently low viscosity to flow efficiently through a hypodermic needle of a gauge effective for subcutaneous injection into human subjects.

45. A lyophilate, in certain embodiments a pharmaceutical lyophilate, in accordance with any of the foregoing or the following, wherein the composition is disposed in a sterile container under vacuum, the diluent is sterile and degassed, and the resulting solution is sterile, is suitable for administration to a human subject by subcutaneous injection, and the viscosity of the resulting solution is below 10, 15, 20, 25, 30, 35, 40, 45, 50, 55, 60, 65, 70, 75, 80, 90, or 100 cP, in particular embodiments below 50 cP, in certain embodiments below 25 cP, in various embodiments below 10 CP.

46. A lyophilate, in certain embodiments a pharmaceutical lyophilate, in accordance with any of the foregoing or the following, wherein the composition is disposed in a sterile container under vacuum, the diluent is sterile and degassed, and the resulting solution is sterile, is suitable for administration to a human subject by subcutaneous injection and is of sufficiently low viscosity to flow efficiently through a hypodermic needle of a gauge effective for subcutaneous injection into human subjects.

47. A lyophilate, in certain embodiments a pharmaceutical lyophilate, in accordance with any of the foregoing or the following, wherein addition of the diluent results in a solution comprising the protein at approximately 40 to 150 mg/ml, approximately 7 to 50 mM histidine, approximately 2% to 4% mannitol, approximately 1.0 to 2.5% sucrose, and approximately 0.004% to 0.015% polysorbate 20 or polysorbate 80, with pH 4.5 to 7.5.

48. A lyophilate, in certain embodiments a pharmaceutical lyophilate, in accordance with any of the foregoing or the following, wherein addition of the diluent results in a solution comprising the protein at approximately 40 to 150 mg/ml, approximately 20 mM histidine, approximately 3.3% mannitol, approximately 2% sucrose, and approximately 0.01% polysorbate 20 or polysorbate 80, with pH approximately 5.0.

49. A lyophilate, in certain embodiments a pharmaceutical lyophilate, in accordance with any of the foregoing or the following, wherein addition of the diluent results in a solution comprising the protein at approximately 40 to 150 mg/ml, approximately 10 mM to 20 mM Tris, approximately 2.0% to 4.2% mannitol, approximately 0.5% to 2.5% sucrose, approximately 0.004% to 0.015% polysorbate 20 or polysorbate 80, at pH 4.5 to 7.6.

50. A lyophilate, in certain embodiments a pharmaceutical lyophilate, in accordance with any of the foregoing or the following, wherein addition of the diluent results in a solution comprising the protein at approximately 40 to 60 mg/ml, approximately 10 mM Tris, approximately 4% mannitol, approximately 2% sucrose, approximately 0.004% polysorbate 20 or polysorbate 80, at approximately pH 7.4.

51. A lyophilate, in certain embodiments a pharmaceutical lyophilate, in accordance with any of the foregoing or the following, wherein the protein comprises a region of an antibody, or of a variant, derivative, fragment, or mimetic thereof.

52. A lyophilate, in certain embodiments a pharmaceutical lyophilate, in accordance with any of the foregoing or the following, wherein the protein comprises a region of an antibody.

53. A lyophilate, in certain embodiments a pharmaceutical lyophilate, in accordance with any of the foregoing or the following, wherein the protein is a human antibody, or of a variant, derivative, fragment, or mimetic thereof.

54. A lyophilate, in certain embodiments a pharmaceutical lyophilate, in accordance with any of the foregoing or the following, wherein the protein comprises a region of a human antibody.

55. A lyophilate, in certain embodiments a pharmaceutical lyophilate, in accordance with any of the foregoing or the following, wherein the protein comprises a region of a human IgG antibody, or a variant, derivative, fragment, or mimetic thereof.

56. A lyophilate, in certain embodiments a pharmaceutical lyophilate, in accordance with any of the foregoing or the following, wherein the protein comprises an effector moiety of an antibody or a variant, derivative, fragment, or mimetic thereof.

57. A lyophilate, in certain embodiments a pharmaceutical lyophilate, in accordance with any of the foregoing or the following, wherein the protein comprises an effector moiety of an Fc region of an antibody or a variant, derivative, fragment, or mimetic thereof.

58. A lyophilate, in certain embodiments a pharmaceutical lyophilate, in accordance with any of the foregoing or the following, wherein the protein is any of an IgA, IgD, IgE, IgG, or IgM antibody or a variant, derivative, fragment, or mimetic thereof.

59. A lyophilate, in certain embodiments a pharmaceutical lyophilate, in accordance with any of the foregoing or the following, wherein the protein comprises a region of a human IgG antibody, or a variant, derivative, fragment, or mimetic thereof.

60. A lyophilate, in certain embodiments a pharmaceutical lyophilate, in accordance with any of the foregoing or the following, wherein the protein comprises a region of a human IgG antibody, or a variant, derivative, fragment, or mimetic thereof.

61. A lyophilate, in certain embodiments a pharmaceutical lyophilate, in accordance with any of the foregoing or the following, wherein the protein is any of an IgG1, IgG2, IgG3, or IgG4, antibody or a variant, derivative, fragment, or mimetic thereof.

62. A lyophilate, in certain embodiments a pharmaceutical lyophilate, in accordance with any of the foregoing or the following, wherein the protein is an IgG antibody or a variant, derivative, fragment, or mimetic thereof.

63. A lyophilate, in certain embodiments a pharmaceutical lyophilate, in accordance with any of the foregoing or the following, wherein the protein is an IgG1 antibody or a variant, derivative, fragment, or mimetic thereof.

64. A lyophilate, in certain embodiments a pharmaceutical lyophilate, in accordance with any of the foregoing or the following, wherein the protein is any of an IgA1 or IgA2 antibody or a variant, derivative, fragment, or mimetic thereof.

65. A lyophilate, in certain embodiments a pharmaceutical lyophilate, in accordance with any of the foregoing or the following, wherein the protein is a single chain antibody or a variant, derivative, fragment, or mimetic thereof.

66. A lyophilate, in certain embodiments a pharmaceutical lyophilate, according to any of the foregoing or the following, wherein the protein is a chimeric antibody or a variant, derivative, fragment, or mimetic thereof.

67. A lyophilate, in certain embodiments a pharmaceutical lyophilate, in accordance with any of the foregoing or the following, wherein the protein is a humanized antibody, or a variant, derivative, fragment, or mimetic thereof.

68. A lyophilate, in certain embodiments a pharmaceutical lyophilate, in accordance with any of the foregoing or the following, wherein the antibody is a human antibody, or a variant, derivative, fragment, or mimetic thereof.

69. A lyophilate, in certain embodiments a pharmaceutical lyophilate, in accordance with any of the foregoing or the following, wherein the protein is a peptibody.

70. A lyophilate, in certain embodiments a pharmaceutical lyophilate, in accordance with any of the foregoing or the following, wherein the protein comprises an effector moiety of an antibody or a variant, derivative, fragment, or mimetic thereof.

71. A lyophilate, in certain embodiments a pharmaceutical lyophilate, in accordance with any of the foregoing or the following, wherein the protein comprises a fragment of an Fc region of an antibody or a variant, derivative, fragment, or mimetic thereof.

72. A lyophilate, in certain embodiments a pharmaceutical lyophilate, in accordance with any of the foregoing or the following, wherein the protein comprises the Fc region of an antibody or a variant, derivative, fragment, or mimetic thereof.

73. A lyophilate, in certain embodiments a pharmaceutical lyophilate, in accordance with any of the foregoing or the following, wherein the protein comprises the Fc region of an antibody.

74. A lyophilate, in certain embodiments a pharmaceutical lyophilate, in accordance with any of the foregoing or the following, wherein the protein is a fusion protein.

75. A lyophilate, in certain embodiments a pharmaceutical lyophilate, in accordance with any of the foregoing or the following, wherein the protein is a fusion protein comprising an effector moiety of an antibody or a variant, derivative, fragment, or mimetic thereof.

76. A lyophilate, in certain embodiments a pharmaceutical lyophilate, in accordance with any of the foregoing or the following, wherein the protein is a fusion protein comprising a fragment of an Fc region of an antibody or a variant, derivative, fragment, or mimetic thereof.

77. A lyophilate, in certain embodiments a pharmaceutical lyophilate, in accordance with any of the foregoing or the following, wherein the protein is a fusion protein comprising the Fc region of an antibody or a variant, derivative, fragment, or mimetic thereof.

78. A lyophilate, in certain embodiments a pharmaceutical lyophilate, in accordance with any of the foregoing or the following, wherein the protein is a fusion protein comprising the Fc region of an antibody.

79. A lyophilate, in certain embodiments a pharmaceutical lyophilate, in accordance with any of the foregoing or the following, wherein the resulting solution comprises the Fc fusion protein at approximately 40 to 60 mg/ml, a buffering agent, approximately 4.0% mannitol, and approximately 2% sucrose, at pH approximately 6.8 to 7.6.

80. A lyophilate, in certain embodiments a pharmaceutical lyophilate, in accordance with any of the foregoing or the following, wherein the resulting solution comprises the Fc fusion protein at approximately 50 mg/ml, approximately 10 mM to 20 mM Tris, approximately 4.0% mannitol, and approximately 2% sucrose, at pH approximately 7.2 to 7.6.

81. A lyophilate, in certain embodiments a pharmaceutical lyophilate, in accordance with any of the foregoing or the following, wherein the resulting solution comprises the Fc fusion protein at approximately 50 mg/ml, approximately 10 mM to 20 mM Tris, approximately 4.0% mannitol, approximately 2% sucrose, and approximately 0.004% polysorbate, at pH approximately 7.4.

82. A lyophilate, in certain embodiments a pharmaceutical lyophilate, in accordance with any of the foregoing or the following, wherein the protein is a fusion protein comprising any or both of an effector moiety of an antibody, or a variant, derivative, fragment, or mimetic thereof and a ligand-binding moiety of a ligand-binding protein, or a variant, derivative, fragment, or mimetic thereof.

83. A lyophilate, in certain embodiments a pharmaceutical lyophilate, in accordance with any of the foregoing or the following, wherein the protein is a fusion protein comprising an Fc region of an antibody, or a variant, derivative, fragment, or mimetic thereof and a TNF binding moiety of a TNF receptor, or a variant, derivative, fragment, or mimetic thereof.

84. A lyophilate, in certain embodiments a pharmaceutical lyophilate, in accordance with any of the foregoing or the following, wherein the protein is a fusion protein comprising an Fc region of a human antibody, or a variant, derivative, fragment, or mimetic thereof, and the TNF alpha binding moiety of a human TNF alpha receptor, or a variant, derivative, fragment, or mimetic of a human TNF alpha receptor.

85. A lyophilate, in certain embodiments a pharmaceutical lyophilate, in accordance with any of the foregoing or the following, wherein the protein is a fusion protein comprising an effector moiety of an antibody, or a variant, derivative, fragment, or mimetic thereof, and a binding moiety of a protein ligand, or a variant, derivative, fragment, or mimetic thereof.

86. A lyophilate, in certain embodiments a pharmaceutical lyophilate, in accordance with any of the foregoing or the following, wherein the protein is a fusion protein comprising an Fc region of an antibody, or a variant, derivative, fragment, or mimetic thereof and the IL-1 binding moiety of a protein ligand of an IL-1 receptor, or a variant, derivative, fragment, or mimetic thereof.

87. A lyophilate, in certain embodiments a pharmaceutical lyophilate, in accordance with any of the foregoing or the following, wherein the protein is a fusion protein comprising an Fc region of a human antibody, or a variant, derivative, fragment, or mimetic thereof, and the IL-1 receptor binding moiety of a human protein ligand of the IL-1 receptor.

88. A lyophilate, in certain embodiments a pharmaceutical lyophilate, in accordance with any of the foregoing or the following, wherein the protein is a fusion protein comprising an Fc region of a human antibody, or a variant, derivative, fragment or mimetic thereof, and the IL-1 receptor binding moiety of an antagonist of the IL-1 receptor.

89. A lyophilate, in certain embodiments a pharmaceutical lyophilate, in accordance with any of the foregoing or the following, wherein the protein is a fusion protein comprising an Fc region of a human antibody, or a variant, derivative, fragment, or mimetic thereof, and the IL-1 receptor binding moiety of the human IL-1ra protein antagonist of the IL-1 receptor.

90. A lyophilate, in certain embodiments a pharmaceutical lyophilate, in accordance with any of the foregoing or the following, wherein the protein is Fc-IL-1ra.

91. A lyophilate, in certain embodiments a pharmaceutical lyophilate, in accordance with any of the foregoing or the following, wherein the protein is Fc-IL-1ra, and wherein in three minutes or less after adding a diluent to said lyophilate: (a) the lyophilate is at least 90%+/−10% dissolved; (b) the height of foam above the resulting solution is less than 35% of the height of the foam above the solution plus the height of the solution; (c) there is no readily visible effervescence in the solution; and (d) the resulting solution contains Fc-IL-1ra at a concentration of 40 to 150 mg/ml in approximately 7 to 50 mM histidine, approximately 2% to 4% mannitol, approximately 1.0 to 2.5% sucrose, and approximately 0.004% to 0.015% polysorbate 20 or polysorbate 80, with pH approximately 4.5 to 7.5.

92. A lyophilate, in certain embodiments a pharmaceutical lyophilate, in accordance with any of the foregoing or the following, wherein addition of the diluent results in a solution comprising Fc-IL-1ra at approximately 75 to 125 mg/ml, in approximately 20 mM histidine, approximately 3.3% mannitol, approximately 2% sucrose, and approximately 0.01% polysorbate 20 or polysorbate 80, with pH approximately 5.0.

93. A method for producing a lyophilized protein composition, in certain embodiments a pharmaceutical lyophilate, in accordance with any of the foregoing or the following, comprising:
(a) annealing a composition comprising a protein under reduced pressure at a first, annealing, temperature;
(b) drying the annealed composition under further reduced pressure at a first drying temperature for a time effective to reduce the moisture content to 75% or less; and
(c) further drying the composition under the further reduced temperature at a second drying temperature for a time effective to reduce the moisture content of the composition to less than 3.5%, thereby producing the lyophilized protein composition.

94. A method for producing a lyophilized protein composition, in certain embodiments a pharmaceutical lyophilate, in accordance with any of the foregoing or the following, comprising:
(a) applying a vacuum to a composition comprising water, a protein, and a lyoprotectant or bulking agent;
(b) cooling the composition under partial vacuum to or below a first reduced temperature;
(c) maintaining the composition under partial vacuum at or below the first reduced temperature until it is completely frozen;
(d) raising the temperature of the composition under partial vacuum to an annealing temperature;
(e) maintaining the composition at the annealing temperature under partial vacuum for a time effective for programmed crystallization of more than 60% of the bulking agent in the composition;
(f) cooling the composition under partial vacuum to a second reduced temperature, keeping the composition below the glass transition temperature throughout the cooling process;
(g) maintaining the composition at the second reduced temperature;
(h) raising the temperature of the composition under vacuum to a first drying temperature less than the glass transition temperature, keeping the composition below the glass transition temperature throughout the heating process;
(i) maintaining the composition under vacuum at the first drying temperature and below the glass transition temperature until the water content of the composition is 10% or less;
(j) raising the temperature of the composition under vacuum to a second drying temperature, keeping the composition below the glass transition temperature throughout the heating process;
(k) maintaining the composition at the second drying temperature until the water content of the composition is 3% or less, maintaining the composition below the glass transition temperature throughout the process, thereby producing the lyophilate.

95. A method for producing a lyophilized protein composition, in certain embodiments a pharmaceutical lyophilate, in accordance with any of the foregoing or the following, comprising:
(a) reducing the temperature of a composition comprising a protein and a bulking agent to a first minimum temperature of 40° C. or less;
(b) raising the temperature of the composition to an annealing temperature between −25° C. and 0° C.;
(c) holding the composition at the annealing temperature;
(d) reducing the temperature of the composition to a second minimum temperature of 0° C. or less;
(e) raising the temperature of the composition to a first drying temperature of or above −10° C.;
(f) holding the composition at the first drying temperature;
(g) raising the temperature of the composition to a second drying temperature;
(h) holding the composition at the second drying temperature until the composition is dry, thereby producing the lyophilate.

96. A method for producing a lyophilized protein composition, in certain embodiments a pharmaceutical lyophilate, in accordance with any of the foregoing or the following, comprising:
(a) reducing the temperature of a lyophilate comprising a protein and a bulking agent to a first minimum temperature of −40° C. or less;
(b) raising the temperature of the composition to an annealing temperature between −25° C. and 0° C.;
(c) holding the composition at the annealing temperature for one hour or more;
(d) reducing the temperature of the composition to a second minimum temperature of 40° C. or less;
(e) raising the temperature of the composition to a first drying temperature of or above −10° C.;
(f) holding the composition at the first drying temperature for five hours or more;
(g) raising the temperature of the composition to a second drying temperature;
(h) holding the composition at the second drying temperature for two hours or more until the composition is dry, thereby producing the protein lyophilate.

97. A method for producing a lyophilized protein composition, in certain embodiments a pharmaceutical lyophilate, in accordance with any of the foregoing or the following, comprising:
(a) reducing the temperature of a lyophilate comprising a protein and a bulking agent at between 0.05 and 1.0° C. per minute to a first minimum temperature of −40° C. or less;
(b) raising the temperature of the composition to an annealing temperature between −25° C. and 0° C.;
(c) holding the composition at the annealing temperature for more than 1 hour;
(d) reducing the temperature of the composition at a rate between 0.05 and 1.0° C. per minute to a second minimum temperature of −40° C. or less;
(e) raising the temperature of the composition at a rate between 0.05 and 1.0° C. per minute to a first drying temperature of or above −10° C.;
(f) holding the composition at the first drying temperature for 5 or more hours;
(g) raising the temperature of the composition at a rate between 0.05 and 1.0° C. per minute to a second drying temperature;
(h) holding the composition at the second drying temperature for at least two hours until the composition is dry, thereby producing the protein lyophilate.

98. A method for producing a lyophilized protein composition, in certain embodiments a pharmaceutical lyophilate, in accordance with any of the foregoing or the following, wherein the composition for lyophilization is degassed prior to the initial freezing step.

99. A method for producing a lyophilized protein composition, in certain embodiments a pharmaceutical lyophilate, in accordance with any of the foregoing or the following, wherein the composition for lyophilization is cooled to 5° C. and held at that temperature until it is fully equilibrated thereto prior to the initial freezing step.

100. A method for producing a lyophilized protein composition, in certain embodiments a pharmaceutical lyophilate, in accordance with any of the foregoing or the following, wherein the resulting lyophilate is a lyophilate comprising a protein in accordance with any of the foregoing.

101. A method for producing a lyophilized composition comprising Fc-IL-1ra, in certain embodiments a pharmaceutical lyophilate comprising Fc-IL-1ra, in accordance with any of the foregoing or the following, comprising:
（a) formulating a solution comprising Fc-IL-1ra, a buffering agent, a bulking agent, and a protectant, and then equilibrating the formulation to a temperature about five degrees above the freezing point;
(b) cooling the composition under partial vacuum to a first freezing temperature at or between −60 and 40° C.;
(c) maintaining the composition under partial vacuum at or below the first reduced temperature until it is completely frozen;
(d) raising the temperature of the composition under partial vacuum to an annealing temperature at or between −10 to −15° C.;
(e) maintaining the composition at the annealing temperature under partial vacuum for a time effective for programmed crystallization of more than 90%+/−10% of the bulking agent in the composition;
(f) cooling the composition under partial vacuum to a second reduced temperature at or between −40 and −60° C.;
(g) maintaining the composition at the second reduced temperature under partial vacuum and then pulling a full vacuum;
(h) raising the temperature of the composition under vacuum to a first drying temperature, keeping the composition below the glass transition temperature throughout the heating process;
(i) maintaining the composition under vacuum at the first drying temperature always below the glass transition temperature until the water content of the composition is 10% or less;
(j) raising the temperature of the composition under vacuum to a second drying temperature, keeping the composition below the glass transition temperature throughout the heating process;
(k) maintaining the composition at the second drying temperature until the water content of the composition is 2% or less, maintaining the composition below the glass transition temperature throughout the process, thereby producing the lyophilate.

102. A method for producing a lyophilized composition comprising Fc-IL-1ra, in certain embodiments a pharmaceutical lyophilate comprising Fc-IL-1ra, in accordance with any of the foregoing or the following, wherein the formulation for lyophilization contains approximately 3.3% mannitol and approximately 2% sucrose, and has a pH of approximately 5.0.

103. A method for producing a lyophilized composition comprising Fc-IL-1ra, in certain embodiments a pharmaceutical lyophilate comprising Fc-IL-1ra, in accordance with any of the foregoing or the following, wherein the formulation for lyophilization contains Fc-IL-1ra at a concentration of approximately 100 mg/ml.

104. A method for producing a lyophilized composition, in certain embodiments a pharmaceutical lyophilate, in accordance with any of the foregoing or the following, comprising an Fc fusion protein, comprising:
(a) formulating a lyophilate comprising an Fc fusion protein, a buffering agent, a bulking agent, and a protectant in solution, degassing the composition, and then equilibrating the composition to a temperature approximately five degrees above the freezing point;
(b) cooling the composition under partial vacuum above 250 mTorr to a first freezing temperature at or between −60 and −40° C.;
(c) maintaining the composition under partial vacuum at or below the first reduced temperature until it is completely frozen;
(d) raising the temperature of the composition under partial vacuum to a temperature at or between −10 to −15° C.;
(e) maintaining the composition at the temperature in (d) under partial vacuum for a time effective for crystallization of more than 60% of the bulking agent in the composition;
(f) cooling the composition under partial vacuum to a second reduced temperature at or between −40 and −60° C.;
(g) maintaining the composition at the second reduced temperature under partial vacuum for a period of time;
(h) under vacuum less than 250 mTorr, raising the temperature of the composition to a first drying temperature, keeping the composition below the glass transition temperature throughout the heating process;
(i) maintaining the composition under vacuum at the first drying temperature always below the glass transition temperature until the water content of the composition is 10% or less;
(j) raising the temperature of the composition under vacuum to a second drying temperature, keeping the composition below the glass transition temperature throughout the heating process;
(k) maintaining the composition at the second drying temperature until the water content of the composition is 3% or less, maintaining the composition below the glass transition temperature throughout the process, thereby producing the lyophilate.

105. A method for producing a lyophilized protein composition, in certain embodiments a pharmaceutical lyophilate, in accordance with any of the foregoing or the following, wherein the composition for lyophilization comprises approximately 3.3% to 4.2% mannitol and approximately 1.5% to 2.5% sucrose.

106. A method for producing a lyophilized protein composition, in certain embodiments a pharmaceutical lyophilate, in accordance with any of the foregoing or the following, wherein the composition for lyophilization comprises the Fc fusion protein at a concentration of approximately 40 to 60 mg/ml.

107. A method for producing a lyophilized protein composition, in certain embodiments a pharmaceutical lyophilate, in accordance with any of the foregoing or the following, wherein the composition for lyophilization comprises approximately 4.0% mannitol and approximately 2% sucrose.

108. A method for producing a lyophilized protein composition, in certain embodiments a pharmaceutical lyophilate, in accordance with any of the foregoing or the following, wherein the composition comprises Tris and has a pH of approximately 7.2 to 7.6.

109. A method for producing a lyophilized protein composition, in certain embodiments a pharmaceutical lyophilate, in accordance with any of the foregoing or the following, wherein the composition comprises approximately 10 mM to 20 mM Tris and has a pH of approximately 7.4.

110. A method for producing a lyophilized protein composition, in certain embodiments a pharmaceutical lyophilate, in accordance with any of the foregoing or the following, wherein the composition comprises the Fc fusion protein at a concentration of approximately 50 mg/ml.

111. A method for producing a lyophilized protein composition, in certain embodiments a pharmaceutical lyophilate, in accordance with any of the foregoing or the following, wherein the lyophilate comprises a protein in accordance with any of the foregoing or following lyophilates.

112. A method for producing a lyophilized protein composition, in certain embodiments a pharmaceutical lyophilate, in accordance with any of the foregoing or the following, comprising:
  (a) equilibrating an approximately 100 mg/ml sample of the protein to approximately 4° C.;
  (b) cooling the sample to approximately −50° C. at approximately −0.5° C./min and then holding the sample at approximately −50° C. for approximately 120 minutes;
  (c) warming the sample to approximately −12° C. at approximately 1.3° C./min and then holding the sample at approximately −12° C. for approximately 360 minutes;
  (d) cooling the sample to approximately −50° C. at approximately 0.6° C./min and then holding the sample at approximately −50° C. for approximately 120 minutes;
  (e) adjusting the ambient pressure on the sample to approximately 100 mTorr;
  (f) maintaining the pressure at approximately 100 mTorr, warming the sample to approximately −25° C. at approximately 0.2° C./min and then holding the sample at approximately −25° C. for approximately 1600 minutes;
  (g) warming the sample to approximately 25° C. at approximately 0.03° C./min, reducing the pressure to approximately 50 mTorr and then holding the sample at approximately 25° C. and approximately 50 mTorr for approximately 800 minutes;

113. A method for producing a lyophilized protein composition, in certain embodiments a pharmaceutical lyophilate, in accordance with any of the foregoing or the following, comprising:
  (a) equilibrating an approximately 100 mg/ml sample of the protein to approximately 4° C.;
  (b) cooling the sample to approximately −50° C. at approximately −0.5° C./min and then holding the sample at approximately −50° C. for approximately 120 minutes;
  (c) warming the sample to approximately −12° C. at approximately 1.3° C./min and then holding the sample at approximately −12° C. for approximately 360 minutes;
  (d) cooling the sample to approximately −50° C. at approximately 0.6° C./min and then holding the sample at approximately −50° C. for approximately 120 minutes;
  (e) adjusting the ambient pressure on the sample to approximately 100 mTorr;
  (f) maintaining the pressure at approximately 100 mTorr, warming the sample to approximately −25° C. at approximately 0.2° C./min and then holding the sample at approximately −25° C. for approximately 1600 minutes;
  (g) warming the sample to approximately 25° C. at approximately 0.03° C./min, reducing the pressure to approximately 50 mTorr and then holding the sample at approximately 25° C. and approximately 50 mTorr for approximately 800 minutes;
wherein the protein comprises an Fc region of an antibody or a variant, derivative, fragment, or mimetic thereof.

114. A method for producing a lyophilized protein composition, in certain embodiments a pharmaceutical lyophilate, in accordance with any of the foregoing or the following, comprising:
  (a) equilibrating an approximately 100 mg/ml sample of the protein to approximately 4° C.;
  (b) cooling the sample to approximately −50° C. at approximately −0.5° C./min and then holding the sample at approximately −50° C. for approximately 120 minutes;
  (c) warming the sample to approximately −12° C. at approximately 1.3° C./min and then holding the sample at approximately −12° C. for approximately 360 minutes;
  (d) cooling the sample to approximately −50° C. at approximately 0.6° C./min and then holding the sample at approximately −50° C. for approximately 120 minutes;
  (e) adjusting the ambient pressure on the sample to approximately 100 mTorr;
  (f) maintaining the pressure at approximately 100 mTorr, warming the sample to approximately −25° C. at approximately 0.2° C./min and then holding the sample at approximately −25° C. for approximately 1600 minutes;
  (g) warming the sample to approximately 25° C. at approximately 0.03° C./min, reducing the pressure to approximately 50 mTorr and then holding the sample at approximately 25° C. and approximately 50 mTorr for approximately 800 minutes;
wherein the protein comprises an Fc region of an antibody.

115. A method for producing a lyophilized protein composition, in certain embodiments a pharmaceutical lyophilate, in accordance with any of the foregoing or the following, comprising:
  (a) equilibrating an approximately 100 mg/ml sample of the protein to approximately 4° C.;
  (b) cooling the sample to approximately −50° C. at approximately −0.5° C./min and then holding the sample at approximately −50° C. for approximately 120 minutes;
  (c) warming the sample to approximately −12° C. at approximately 1.3° C./min and then holding the sample at approximately −12° C. for approximately 360 minutes;
  (d) cooling the sample to approximately −50° C. at approximately 0.6° C./min and then holding the sample at approximately −50° C. for approximately 120 minutes;
  (e) adjusting the ambient pressure on the sample to approximately 100 mTorr;
  (f) maintaining the pressure at approximately 100 mTorr, warming the sample to approximately −25° C. at approximately 0.2° C./min and then holding the sample at approximately −25° C. for approximately 1600 minutes;
  (g) warming the sample to approximately 25° C. at approximately 0.03° C./min, reducing the pressure to approximately 50 mTorr and then holding the sample at approximately 25° C. and approximately 50 mTorr for approximately 800 minutes;
wherein the protein is Fc-IL-1ra.

116. A method for producing a lyophilized protein composition, in certain embodiments a pharmaceutical lyophilate, in accordance with any of the foregoing or the following, comprising:
(a) equilibrating a 100 mg/ml sample of the protein to 4° C.;
(b) cooling the sample to −50° C. at −0.5° C./min and then holding the sample at −50° C. for 120 minutes;
(c) warming the sample to −12° C. at 1.3° C./min and then holding the sample at −12° C. for 360 minutes;
(d) cooling the sample to −50° C. at 0.6° C./min and then holding the sample at −50° C. for 120 minutes;
(e) adjusting the ambient pressure on the sample to 100 mTorr;
(f) maintaining the pressure at 100 mTorr, warming the sample to −25° C. at 0.2° C./min and then holding the sample at −25° C. for approximately 1600 minutes;
(g) warming the sample to 25° C. at 0.03° C./min, reducing the pressure to 50 mTorr and then holding the sample at 25° C. and 50 mTorr for 800 minutes.

117. A method for producing a lyophilized protein composition, in certain embodiments a pharmaceutical lyophilate, in accordance with any of the foregoing or the following, comprising:
(a) equilibrating a 100 mg/ml sample of the protein to 4° C.;
(b) cooling the sample to −50° C. at −0.5° C./min and then holding the sample at −50° C. for 120 minutes;
(c) warming the sample to −12° C. at 1.3° C./min and then holding the sample at −12° C. for 360 minutes;
(d) cooling the sample to −50° C. at 0.6° C./min and then holding the sample at −50° C. for 120 minutes;
(e) adjusting the ambient pressure on the sample to 100 mTorr;
(f) maintaining the pressure at 100 mTorr, warming the sample to −25° C. at 0.2° C./min and then holding the sample at −25° C. for approximately 1600 minutes;
(g) warming the sample to 25° C. at 0.03° C./min, reducing the pressure to 50 mTorr and then holding the sample at 25° C. and 50 mTorr for 800 minutes;
wherein the protein comprises an Fc region of an antibody or a variant, derivative, fragment, or mimetic thereof.

118. A method for producing a lyophilized protein composition, in certain embodiments a pharmaceutical lyophilate, in accordance with any of the foregoing or the following, comprising:
(a) equilibrating a 100 mg/ml sample of the protein to 4° C.;
(b) cooling the sample to −50° C. at −0.5° C./min and then holding the sample at −50° C. for 120 minutes;
(c) warming the sample to −12° C. at 1.3° C./min and then holding the sample at −12° C. for 360 minutes;
(d) cooling the sample to −50° C. at 0.6° C./min and then holding the sample at −50° C. for 120 minutes;
(e) adjusting the ambient pressure on the sample to 100 mTorr;
(f) maintaining the pressure at 100 mTorr, warming the sample to −25° C. at 0.2° C./min and then holding the sample at −25° C. for approximately 1600 minutes;
(g) warming the sample to 25° C. at 0.03° C./min, reducing the pressure to 50 mTorr and then holding the sample at 25° C. and 50 mTorr for 800 minutes;
wherein the protein comprises an Fc region of an antibody.

119. A method for producing a lyophilized protein composition, in certain embodiments a pharmaceutical lyophilate, in accordance with any of the foregoing or the following, comprising:
(a) equilibrating a 100 mg/ml sample of the protein to 4° C.;
(b) cooling the sample to −50° C. at −05° C./min and then holding the sample at −50° C. for 120 minutes;
(c) warming the sample to −12° C. at 1.3° C./min and then holding the sample at −12° C. for 360 minutes;
(d) cooling the sample to −50° C. at 0.6° C./min and then holding the sample at −50° C. for 120 minutes;
(e) adjusting the ambient pressure on the sample to 100 mTorr;
(f) maintaining the pressure at 100 mTorr, warming the sample to −25° C. at 0.2° C./min and then holding the sample at −25° C. for approximately 1600 minutes;
(g) warming the sample to 25° C. at 0.03° C./min, reducing the pressure to 50 mTorr and then holding the sample at 25° C. and 50 mTorr for 800 minutes;
wherein the protein is Fc-IL-1ra.

120. A sealed vial having disposed therein under sterile conditions and reduced pressure a sterile lyophilate composition, in certain embodiments a pharmaceutical lyophilate, in accordance with any of the foregoing or the following.

121. A sealed vial having disposed therein under sterile conditions and reduced pressure a sterile lyophilate composition, in certain embodiments a pharmaceutical lyophilate, in accordance with any of the foregoing or the following, comprising a septum through which a sterile hypodermic needle may be introduced aseptically to add diluent and to withdraw the resulting solution.

122. A sealed vial having disposed therein under sterile conditions and reduced pressure a sterile lyophilate composition, in certain embodiments a pharmaceutical lyophilate, in accordance with any of the foregoing or the following, wherein the composition is a unit dose of a drug for human use, or a multiple thereof.

123. A sealed vial having disposed therein under sterile conditions and reduced pressure a sterile lyophilate composition, in certain embodiments a pharmaceutical lyophilate, in accordance with any of the foregoing or the following, wherein the composition is disposed therein under vacuum below 500 mTorr.

124. A sealed vial having disposed therein under sterile conditions and reduced pressure a sterile lyophilate composition, in certain embodiments a pharmaceutical lyophilate, in accordance with any of the foregoing or the following, wherein the lyophilate therein disposed is produced by a method in accordance with any of the foregoing or the following methods.

125. A sealed vial having disposed therein under sterile conditions and reduced pressure a sterile composition that is a pharmaceutical lyophilate in accordance with any of the foregoing or the following, wherein the lyophilate is suitable for administration to a human subject and the protein comprises an Fc region of an antibody or a variant, derivative, fragment, or mimetic thereof.

126. A sealed vial having disposed therein under sterile conditions and reduced pressure a sterile composition that is a pharmaceutical lyophilate in accordance with any of the foregoing or the following, wherein the lyophilate is suitable for administration to a human subject and the protein comprises an Fc region of a human antibody or a variant, derivative, fragment, or mimetic thereof.

127. A sealed vial having disposed therein under sterile conditions and reduced pressure a sterile composition that is a pharmaceutical lyophilate in accordance with any of the foregoing or the following, wherein the lyophilate is suitable for administration to a human subject and the protein comprises a humanized Fc region of an antibody or a variant, derivative, fragment, or mimetic thereof.

128. A sealed vial having disposed therein under sterile conditions and reduced pressure a sterile composition that is a lyophilate, in certain embodiments a pharmaceutical lyophilate, in accordance with any of the foregoing or the following, comprising an Fc fusion protein, wherein in three minutes or less after adding a diluent to said lyophilate: (a) the lyophilate is at least 90%+/−10% dissolved; (b) the height of foam above the resulting solution is less than 35% of the height of the foam above the solution plus the height of the solution; (c) there is no visible effervescence in the solution; and (d) the resulting solution comprises an Fc fusion protein at a concentration of approximately 40 mg/ml or more, approximately 3% to 4% mannitol, and approximately 1.5% to 2.5% sucrose.

129. A sealed vial in accordance with any of the foregoing or the following, having disposed therein under sterile conditions and reduced pressure a sterile composition that is a lyophilate, in some embodiments a pharmaceutical lyophilate, comprising an Fc fusion protein, wherein the resulting solution comprises the Fc fusion protein at a concentration of approximately 50 mg/ml in approximately 10 mM to 20 mM Tris, approximately 4.0% mannitol, approximately 2.0% sucrose, and approximately 0.001% to 0.01% polysorbate, at pH approximately 7.2 to 7.6.

130. A sealed vial having disposed therein under sterile conditions and reduced pressure a sterile composition that is a pharmaceutical lyophilate in accordance with any of the foregoing or the following, wherein the lyophilate is suitable for administration to a human subject and the protein is Fc-IL-1ra.

131. A sealed vial having disposed therein under sterile conditions and reduced pressure a sterile composition that is a pharmaceutical lyophilate in accordance with any of the foregoing or the following, wherein the lyophilate is suitable for administration to a human subject, the protein is Fc-IL-1.A, and wherein further within in three minutes or less after adding a diluent to said lyophilate: (a) the lyophilate is at least 90%+/−10% dissolved; (b) the height of foam above the resulting solution is less than 35% of the height of the foam above the solution plus the height of the solution; (c) there is no visible effervescence in the solution; and (d) the resulting solution contains Fc-IL-1ra at a concentration of approximately 100 mg/ml in approximately 20 mM histidine, approximately 3.3% mannitol, approximately 2.0% sucrose, approximately 0.01% polysorbate 20, at approximately pH 5.0.

132. A vial in accordance with any of the foregoing or the following, comprising a septum through which a sterile hypodermic needle may be introduced aseptically to add diluent and to withdraw the resulting solution.

133. A method for determining polymorphs in a sample in accordance with any of the foregoing or the following, comprising analyzing second derivative Raman imaging spectra obtained from a sample using a partial least squares based algorithm that deconvolutes overlapping polymorph spectra and quantifies the amounts of polymorphs in the sample based thereon.

134. A method for determining mannitol polymorphs in a sample in accordance with any of the foregoing or the following, comprising analyzing second derivative Raman imaging spectra obtained from a sample using a partial least squares algorithm that deconvolutes overlapping polymorph spectra and quantifies the amounts of the mannitol polymorphs in the sample.

135. A method for determining mannitol polymorphs in a sample in accordance with any of the foregoing or the following, comprising analyzing second derivative Raman imaging spectra obtained using a partial least squares algorithm that deconvolutes overlapping polymorph spectra and quantifies the amounts of alpha mannitol, beta mannitol, delta mannitol, mannitol hydrate, and amorphous mannitol.

136. A method for developing an algorithm to quantify different polymorphs of a substance in a sample in accordance with any of the foregoing or the following, comprising: (a) determining the Raman spectra of the different polymorphs of the substance to be determined; (b) adding the spectra to one another in varying proportions to simulate the spectra of mixtures of the polymorphs with one another; (c) analyzing the simulated mixed spectra using partial least squares analysis; and (d) from the analyses deriving a partial least squares based deconvolution routine to quantify the relative amounts of the individual polymorphs in a mixture.

137. A method for determining polymorphs of a substance in a mixture in accordance with any of the foregoing or the following, comprising determining Raman imaging spectra of a multiplicity of defined areas of a sample, applying a partial least squares deconvolution routine to each of said spectra, deriving thereby a quantitative measure of the amounts relative to one another of the polymorphs of the substance in the sample.

138. A method for deriving a program to quantify different polymorphic forms of a substance in a sample, comprising (a) obtaining a Raman spectrum for each polymorphic form to be determined; (b) normalizing the spectra to the C—H stretch at approximately 2800 $cm^{-1}$; (c) obtaining derivative spectra for the normalized spectra; (d) by linear addition of the derivative spectra deriving a calibration set of spectra; (e) using a Partial Least Squares algorithm to analyze the calibration set of spectra to generate a program for quantifying the amount of each polymorph in a sample to be analyzed.

139. A method for quantifying polymorphs of a substance in a sample, comprising (a) obtaining a Raman spectrum for each polymorphic form to be determined; (b) normalizing the spectra to the C—H stretch at approximately 2800 $cm^{-1}$; (c) obtaining derivative spectra for the normalized spectra; (d) by linear addition of the derivative spectra deriving a calibration set of spectra; (e) using a Partial Least Squares algorithm to analyze the calibration set of spectra to generate a program for quantifying the amount of each polymorph in a sample to be analyzed; (f) obtaining the Raman spectrum of the sample; and (g) processing the Raman spectrum using the program to quantify the polymorphs in the sample.

140. A method for quantifying polymorphs in a sample, according to any of the foregoing or the following, wherein the sample is a solid.

141. A method, according to any of the foregoing or the following, for quantifying polymorphs in a sample according to any of the foregoing or the following, wherein the sample is a solid and the Raman spectra is obtained by Raman imaging spectroscopy.

142. A method, according to any of the foregoing or the following, for quantifying polymorphs in a sample according to any of the foregoing or the following, further comprising correcting the spectrum of the sample for the contribution of other components and quantifying the polymorphs based on the corrected spectrum, 143. A method, according to any of the foregoing or the following, for determining the distribution of different solid forms in the samples using Raman imaging data, comprising, obtaining two-dimensional Raman imaging data over a field of a sample, applying a program, derived from PLS analysis of computed calibration Raman spectra, to the two dimensional imaging data to quantify the relative proportions of each solid form to be determined for each pixel measured in the sample field, obtaining thereby the quantitative spatial distribution of the different forms within the sample and, optionally, displaying the distribution of one or more forms so determined using a color scale on a representation of the sample surface.

144. A method for determining polymorphs of a substance in a mixture in accordance with any of the foregoing or the following, comprising the acquisition of Raman imaging spectra through an instrument comprising in operable linkage a vacuum cryostat operably mounted on a microscope stage in operable optical linkage through an objective lens with an Raman imaging spectrometer.

145. A method for determining polymorphs of a substance in a mixture in accordance with any of the foregoing or the following, comprising the acquisition of Raman imaging spectra through an instrument comprising in operable linkage a vacuum cryostat operably mounted on a microscope stage in operable optical linkage through an objective lens with an Raman imaging spectrometer, wherein the vacuum cryostat is effective for controlled lyophilization of samples and the Raman imaging optics through said operable optical linkage is effective for real time acquisition of Raman spectra of samples during lyophilization.

146. A method for determining polymorphs of a substance in a mixture in accordance with any of the foregoing or the following, comprising the acquisition of Raman imaging spectra through an instrument comprising in operable linkage a vacuum cryostat operably mounted on a microscope stage in operable optical linkage through an objective lens with an Raman imaging spectrometer, wherein the vacuum cryostat is effective for controlled lyophilization of samples and the Raman imaging optics through said operable optical linkage is effective for real time acquisition of Raman spectra of samples during lyophilization, wherein further the substance is mannitol and the polymorphs are the alpha mannitol, beta mannitol and delta mannitol, mannitol hydrate, and amorphous mannitol.

GLOSSARY

Figure 1:
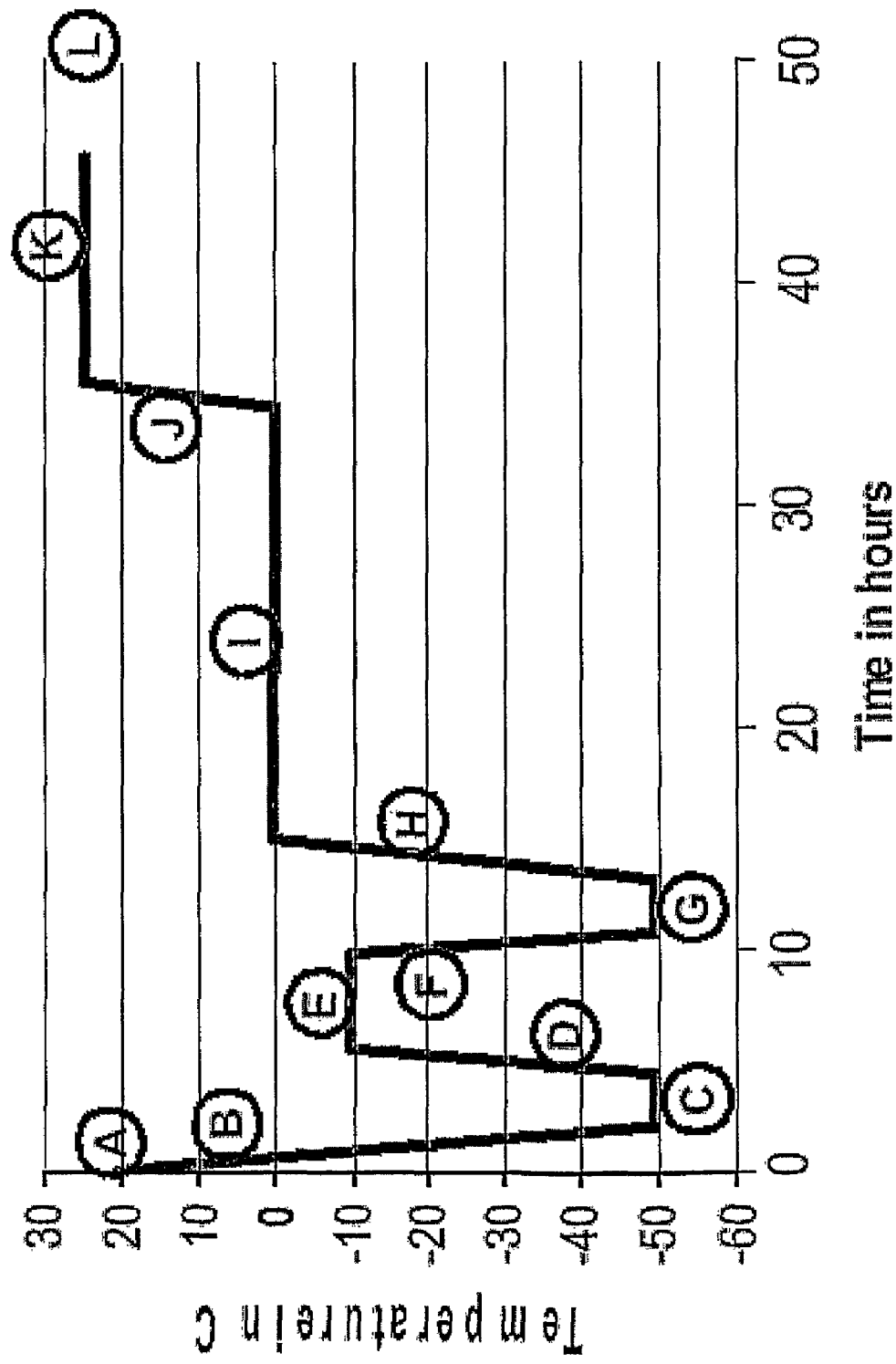
FIG. 1 is a chart showing a typical program for producing protein lyophilates that rapidly and reliably reconstitute in diluent to provide highly concentrated protein formulations.

"A and an" as used herein mean the same as "one or more than one" and the same as "at least one" without further limitation, except as may otherwise be explicitly stated.

"Agonist" as used herein means a molecular entity that is different from a corresponding stimulatory ligand but has that same stimulatory effect. For instance (although agonists work through other mechanisms), for a hormone that stimulates an activity by binding to a corresponding hormone receptor, an agonist is a chemically different entity that binds the hormone receptor and stimulates the same activity as the hormone.

"Annealing" as used herein means a heat treatment that alters the microstructure of a material and changes its properties, typically by providing defect free crystals and minimizing internal stresses. Annealing typically involves heating to a temperature at which the material is too hard to deform but is soft enough for internal stresses to ease, and then holding the material at that temperature until it is thoroughly equilibrated.

In the context of the present invention, annealing particularly involves holding the lyophilate at an annealing temperature for a defined period to ensure crystallization (relatively free of crystal defects) of the crystallizable components in the formulation, particularly the bulking agent. Annealing ensures that such components, particularly the bulking agent, will be stable and will not crystallize during the drying stage. Instability can result in poor cake formation and poor solubility characteristics. Crystallization during the drying stage often causes loss of protein stability in the lyophilate cake and vial breakage, among other deleterious effects.

In general the annealing temperature should be between the Tg of the amorphous phase and the eutectic temperature of the bulking agent to give high crystallization rates and maximize crystallization.

"Antagonist(s)" means herein a molecular entity that is different from a corresponding ligand and has an opposite effect. For instance (although antagonists work through other mechanisms), one type of antagonist of a hormone that stimulates an activity by binding to a corresponding hormone receptor is a chemical entity that is different from the hormone and binds the hormone receptor but does not stimulate the activity engendered by hormone binding, and by this action inhibits the effector activity of the hormone.

"Antibody(s)" is used herein in accordance with its ordinary meaning in the biochemical and biotechnological arts. Among antibodies within the meaning of the term as it is used herein, are those isolated from biological sources, including monoclonal and polyclonal antibodies, antibodies made by recombinant DNA techniques (also referred to at times herein as recombinant antibodies), including those made by processes that involve activating an endogenous gene and those that involve expression of an exogenous expression construct, including antibodies made in cell culture and those made in transgenic plants and animals, and antibodies made by methods involving chemical synthesis, including peptide synthesis and semi-synthesis. Also within the scope of the term as it is used herein, except as otherwise explicitly set forth, are chimeric antibodies and hybrid antibodies, among others.

The prototypical antibody is a tetrameric glycoprotein comprised of two identical light chain-heavy chain dimers joined together by disulfide bonds. There are two types of vertebrate light chains, kappa and lambda. Each light chain is comprised of a constant region and a variable region. The two light chains are distinguished by constant region sequences. There are five types of vertebrate heavy chains: alpha, delta, epsilon, gamma, and mu. Each heavy chain is comprised of a variable region and three constant regions. The five heavy chain types define five classes of vertebrate antibodies (isotypes): IgA, IgD, IgE, IgG, and IgM. Each isotype is made up of, respectively, (a) two alpha, delta, epsilon, gamma, or mu heavy chains, and (b) two kappa or two lambda light chains. The heavy chains in each class associate with both types of light chains; but, the two light chains in a given molecule are both kappa or both lambda. IgD, IgE, and IgG generally occur as "free" heterotetrameric glycoproteins. IgA and IgM generally occur in complexes comprising several IgA or several IgM heterotetramers associated with a "J" chain polypeptide. Some vertebrate isotypes are classified into subclasses, distinguished from one another by differences in constant region sequences. There are four human IgG subclasses, IgG1, IgG2, IgG3, and IgG4, and two IgA subclasses, IgA1 and IgA2, for example. All of these and others not specifically described above are included in the meaning of the term "antibody(s)" as used herein.

The term "antibody(s)" further includes amino acid sequence variants of any of the foregoing as described further elsewhere herein.

"Antibody-derived" as used herein means any protein produced from an antibody, and any protein of a design based on an antibody. The term includes in its meaning proteins produced using all or part of an antibody, those comprising all or part of an antibody, and those designed in whole or in part on the basis of all or part of an antibody. "Antibody-derived" proteins include, but are not limited to, Fc, Fab, and Fab$_2$ fragments and proteins comprising the same, $V_H$ domain and $V_L$ domain fragments and proteins comprising the same, other proteins that comprise a variable and/or a constant region of an antibody, in whole or in part, scFv(s) intrabodies, maxibodies, minibodies, diabodies, amino acid sequence variants of the foregoing, and a variety of other such molecules, including but not limited to others described elsewhere herein.

"Antibody-related" as used herein means any protein or mimetic resembling in its structure, function, or design an antibody or any part of an antibody. Among "antibody-related" proteins as the term is used herein are "antibody-derived" proteins as described above. It is to be noted that the terms "antibody-derived" and "antibody-related" substantially overlap; both terms apply to many such proteins. Examples of "antibody-related" proteins, without implying limitation in this respect, are peptibodies and receptibodies. Other examples of "antibody-related" proteins are described elsewhere herein.

"Antibody polypeptide(s)" as used herein, except as otherwise noted, means a polypeptide that is part of an antibody, such as a light chain polypeptide, a heavy chain polypeptide and a J chain polypeptide, to mention a few examples, including among others fragments, derivatives, and variants thereof, and related polypeptides.

"Approximately" is used herein to mean within a certain fraction of percent of a stated value, and unless stated otherwise, the term nominally denotes a variation about the stated value of plus or minus 20%, preferably plus or minus 10%, very preferably plus or minus 5%.

"Binding moiety(s)" means a part of a molecule or a complex of molecules that binds specifically to part of another molecule or complex of molecules. The binding moiety may be the same or different from the part of the molecule or complex of molecules to which it binds. The binding moiety may be all of a molecule or complex of molecules as well.

"Binds specifically" is used herein in accordance with its ordinary meaning in the art and means, except as otherwise noted, that binding is stronger with certain specific moieties than it is to other moieties in general, that it is stronger than non-specific binding that may occur with a wide variety of moieties, and that binding is selective for certain moieties and does not occur to as strong an extent with others. In the extreme case of specific binding, very strong binding occurs with a single type of moiety, and there is no non-specific binding with any other moiety.

"Composition" means any composition of matter comprising one or more constituents, such as a formulation.

"Comprised of" is a synonym of "comprising" (see below).

"Comprising" means including, without further qualification, limitation, or exclusion as to what else may or may not be included. For example, "a composition comprising x and y" means any composition that contains x and y, no matter what else it may contain. Likewise, "a method comprising x" is any method in which x is carried out, no matter what else may occur.

"Derivative(s)" is used herein to mean derived from, in substance, form, or design, such as, for instance, a polypeptide that is based on but differs from a reference polypeptide, for instance, by alterations to its amino acid sequence, by fusion to another polypeptide, or by covalent modification.

"Effective amount" generally means an amount which provides the desired local or systemic effect. For example, an effective amount is an amount sufficient to effectuate a beneficial or desired clinical result. The effective amount can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

"Effective route" generally means a route which provides for delivery of an agent to a desired compartment, system, or location. For example, an effective route is one through which an agent can be administered to provide at the desired site of action an amount of the agent sufficient to effectuate a beneficial or desired clinical result.

"Etanercept" is a fusion protein that contains the extracellular domain of the p75 TNFalpha receptor fused to an Fc domain of an IgG1 antibody. The resulting dimeric fusion protein binds TNFalpha and inhibits TNFalpha activity. Etanercept is commercially available under the name Enbrel® from Amgen Inc. (Thousand Oaks, Calif.). See for instance Enbrel® package insert, Immunex Corp.; Moreland et al., *Ann Intern Med* 130: 478-486 (1999); E. C. Keystone et al., *Arthritis Rheum* 50: 353-363 (2004); M. E. Weinblatt et al., *N Engl J Med* 340: 253-259 (1999); Klareskog et al., *Lancet* 363: 675-681 (2004); Gorman et al., *N Engl J Med* 346: 1349-1356 (2002); P. J. Mease et al., *Lancet* 356: 385-390 (2000); and C. L. Leonardi et al., *N Engl J Med* 349: 2014-2022 (2003), which are herein incorporated by reference in their entireties, particularly in parts pertinent to the structure and activities of etanercept.

"Fc-IL-1ra" is a fusion protein antagonist of the IL-1 receptor that is formed of an Fc sequence of an antibody and the sequence of an IL-1 receptor binding moiety of the IL-1 receptor antagonist IL-1ra. Fc-IL-1ra is also called IL-1ra-Fc and r-metHu-Fc-IL-1ra. Fc-IL-1ra fusion proteins and related information about Fc-IL-1ra are disclosed in U.S. Pat. No. 6,294,170 to Boone, et al., for "Composition and method for treating inflammatory diseases," issued Sep. 25, 2001, which is herein incorporated by reference in its entirety, in particular in parts pertinent to the structure, formulation, and use of fusion proteins comprising the interleukin-1 receptor antagonist IL-1ra or related polypeptide sequences, as described therein.

"Fragment(s)" herein means part of a larger entity, such as a part of a protein; for instance, a polypeptide consisting of less than the entire amino acid sequence of a larger polypeptide. As used herein, the term includes fragments formed by terminal deletion and fragments formed by internal deletion, including those in which two or more non-contiguous portions of a polypeptide are joined together to form a smaller polypeptide, which is a fragment of the original.

"Fusion protein(s)" herein means a protein formed by fusing all or part of two polypeptides, which may be either the same or different. Typical fusion proteins are made by recombinant DNA techniques, by end to end joining of nucleotides encoding the two (or more) polypeptides. For example, an Fc fusion protein is a protein formed by fusing an Fc protein to another protein.

"Genetically engineered" herein means produced using a deliberate process of genetic alteration, such as by recombinant DNA technology, classical methods of genetic manipulation, chemical methods, a combination of all three, or other methods.

"Glass transition temperature" is the temperature below which a substance loses its elastic properties and becomes hard and brittle (solid) and above which it is elastic (generally, near the transition temperature of glass).

"High concentration" as used herein with reference to protein therapeutic compositions means 40 mg/ml or more.

"Homolog(s)" herein means having homology to another entity, such as a protein that is homologous to another protein. Homologous means resembling in structure or in function.

"Ligand(s)" herein means a molecular entity that binds selectively and stoichiometrically to one or more specific sites on one or more other molecular entities. Binding typically is non-covalent, but can be covalent as well. A very few examples, among many others, are (a) antigens, which typically bind non-covalently to the binding sites on cognate antibodies; (b) hormones, which typically bind hormone receptors, non-covalently; (c) lectins, which bind specific sugars, non-covalently; (d) biotins, which bind multiple sites on avidin and other avidin-like proteins, non-covalently; (e) hormone antagonists, which bind hormone receptors and inhibit their activity and/or that of the corresponding hormone; and (f) hormone agonists, which similarly bind hormone receptors but stimulate their activity.

"Ligand-binding moiety(s)" herein means a molecular entity that binds a ligand, typically, a part of a larger molecular entity that binds the ligand, or a molecular entity derived therefrom.

"Ligand-binding protein(s)" herein means a protein that binds a ligand.

"Ligand moiety(s)" herein means a molecular entity that binds to a ligand-binding molecular entity in much the same way as does the corresponding ligand. A ligand moiety can be all of a ligand, or part of it, derived from a ligand, or generated de novo. Typically, however, the ligand moiety is more or less exclusively the aspect thereof that binds corresponding ligand-binding entities. The ligand moiety need not comprise, and the term generally does not denote, structural features other than those required for ligand binding.

"Mimetic" refers to a chemical entity with structural or functional characteristics of another, generally unrelated chemical entity. For instance, one kind of hormone mimetic is a non-peptide organic molecule that binds to the corresponding receptor in the same way as the corresponding hormone itself.

"Modified protein(s)," "modified polypeptide(s)," or "modified fragment(s)" herein means a protein or a polypeptide or a fragment of a protein or polypeptide comprising a chemical moiety (structure) other than those of the twenty naturally occurring amino acids that form naturally occurring proteins. Modifications most often are covalently attached, but can also be attached non-covalently to a protein or other polypeptide, such as a fragment of a protein.

"Moiety(s)" herein means a molecular entity that embodies a specific structure and/or function, without extraneous components. For instance, in most cases, only a small part of a ligand-binding protein is responsible for ligand binding. This part of the protein, whether continuously encoded or discontinuously, is an example of a ligand-binding moiety.

"Partial vacuum" means a pressure less than atmospheric and above approximately 250 mTorr.

"Peptibody" refers to a molecule comprising an antibody Fc domain (i.e., CH2 and CH3 antibody domains) that excludes antibody CH1, CL, VH, and VL domains as well as Fab and F(ab)$_2$, wherein the Fc domain is attached to one or more peptides, preferably a pharmacologically active peptide, particularly preferably a randomly generated pharmacologically active peptide. The production of peptibodies is generally described in PCT publication WO00/24782, published May 4, 2000, which is herein incorporated by reference in its entirety, particularly as to the structure, synthesis, properties, and uses of peptibodies.

"Peptide(s)" herein means the same as polypeptide; often, but not necessarily, it is used in reference to a relatively short polypeptide, "Pharmaceutical" as used herein means is acceptable for use in a human or non-human subject for the treatment thereof, particularly for use in humans, and approved therefor by a regulatory authority empowered to regulate the use thereof such as, for example, the Food and Drug Administration in the United States, European Agency for the Evaluation of Medicinal Products, Japan's Ministry of Health, Labor and Welfare, or other regulatory agency such as those listed in R. Ng, Drugs: *From Discovery to Approval*, Wiley-Liss (Hoboken, N.J.) (2004), which is herein incorporated by reference in its entirety, particularly as to regulatory authorities concerned with drug approval, especially as listed in Chapter 7. As used herein the phrase "wherein the composition has been approved for pharmaceutical use by an authority legally empowered to grant such approval" means an entity or institution or the like, established by law and by law charged with the responsibility and power to regulate and approve the use of drugs for use in humans, and in some cases, in non-humans. Approval by any one such agency anywhere meets this qualification. It is not necessary for the approving agency to be that of the state in which, for instance, infringement is occurring. Example of such entities include the U.S. Food and Drug Administration and the other agencies listed herein above.

As used herein, "pharmaceutical" also may refer to a product produced in accordance with good manufacturing practices, such as those described in, among others, Chapter 9 and Chapter 10, of R. Ng, *Drugs: From Discovery to Approval*, Wiley-Liss (Hoboken, N.J.) (2004), which is herein incorporated by reference in its entirety, particularly in parts pertinent to good manufacturing practices for pharmaceutical protein formulations, in particular, as set forth in Chapters 9 and 10.

"Pharmaceutically acceptable" is used herein in accordance with its well-known meaning in the art to denote that which is acceptable for medical or veterinary use, preferably for medical use in humans, particularly approved for such use by the U.S. Food and Drug Administration or other authority as described above regarding the meaning of "pharmaceutical."

"Polymorph(s)" means herein chemically identical but structurally different forms of a substance. For instance, mannitol is chemically a distinct entity with five polymorphs. The mannitol is the same in all five polymorphs, but it is organized differently. Three of the polymorphs are crystalline states that differ from one another in their geometric organization of mannitol molecules. One of the forms is mannitol monohydrate, which differs in its geometry from all three crystalline forms. The fifth polymorph is amorphous mannitol, which is not organized in the geometrically precise manner of the three crystalline forms and also is not organized in the same way as the hydrate. While mannitol itself is the same molecule in all five polymorphs, the energy, stability and reactivity of mannitol differs to some extent between them, as a result of their interaction with their effects thereof on one another, which are affected by geometry and by hydration. Since some polymorphs may be better suited to a given formulation than others it can be important to optimize the type and distribution of polymorphs in a composition.

Polymorphs may be stable or they may be unstable, under given conditions of production, formulation, storage, and use. Unstable polymorphs can differ significantly in the energetics and the kinetics of their conversion to more stable forms. It can be useful to take into account the interconversion of a polymorph that may occur during production, formulation, storage, and use of a given composition and optimize the formulation to ensure that the distribution of polymorphs in the composition is optimized over the life of the product. Optimization, notably, may rely as much or more on the kinetics or interconversion as on the energetic stability of the individual polymorphs.

"Polypeptide(s)" see "Protein(s)."

"Precursor(s)" is used herein in accordance with its well-known meaning in the art to denote an entity from which another entity is derived. For instance, a precursor protein is a protein that undergoes processing, such as proteolytic cleavage or modification, thereby giving rise to another precursor protein (which will undergo further processing) or a mature protein.

"Protein(s)" herein means a polypeptide or a complex of polypeptides, in accordance with its well-known meaning in the art. As used herein, "protein(s)" includes both straight chain and branched polypeptides. It includes unmodified and modified polypeptides, including naturally occurring modifications and those that do not occur naturally. Such modifications include chemical modifications of the termini the peptide backbone, and the amino acid side chains; amino acid substitutions, deletions and additions; and incorporation of unusual amino acids and other moieties, to name just a few such modifications. These include, for instance, post-translational modifications, such as, but not limited to, glycosylation, phosphorylation, acetylation, methylation, lipidation, and ubiquitinylation. It also includes "engineered" polypeptides and complexes thereof, such as, but not limited to, any polypeptide or complex of polypeptides that has been deliberately altered in its structure by, for instance, recombinant DNA techniques, chemical synthesis, and/or covalent modification, including deliberate alteration of amino acid sequence and/or posttranslational modifications.

In particular instances, the term as used herein refers more specifically to polypeptides that resist reconstitution at high concentrations due to their relatively high molecular weight, their chemical composition (including amino acid sequence features, modifications and the like), or both.

"Subject" means a vertebrate, such as a mammal, such as a human. Mammals include, but are not limited to, humans, farm animals, sport animals, and pets. Subjects in need of treatment by methods and/or compositions of the present invention include those suffering from a disorder, dysfunction, or disease, or a side effect thereof, or from a side effect of a treatment thereof.

"Substantially" is used herein in accordance with its plain and ordinary definition to mean to a great extent or degree. For example, substantially complete means complete to a great extent, complete to a great degree. By way of further illustration, substantially free of residue means to a great extent free of residue, free of residue to a great degree. Should numerical accuracy be required, depending on context, "substantially," as used herein means, at least, 80% or more, particularly 90% or more, very particularly 95% or more.

"Substantially free of readily visible" means, as used herein, typically as to foam, turbidity, effervescence, particulate formation and settling, or other material, that there is little or no such material visible to a person of average good vision observing directly under average commercial or average residential lighting conditions and that addition of diluent does not engender physical processes associated with one or more of foaming, precipitation, effervescence, and/or aggregation that alter the effective activity or specific activity of the lyophilate in any way that deleteriously affects its efficacy or the acceptability of its appearance for veterinary or human therapeutic use. Thus, "substantially free" in this regard applies not only where there is no visible foam, turbidity, effervescence, or particulate formation and settling, but also where one or more or all of the foregoing are visible but in such small amounts that efficacy and acceptability remain high for veterinary and/or human therapeutic use.

"Tg" means glass transition temperature, also denoted $T_g$.

"Therapeutically effective" is used herein in accordance with its well-known meaning in the art to denote that which achieves an improvement in the prognosis or condition of a subject or that otherwise achieves a therapeutic objective, including, for instance, a reduction in the rate of progress of a disease even if a subject's condition, nonetheless, continues to deteriorate.

"Therapeutically effective amount" generally is used to quantify the amount of an agent to encompass those amounts that achieve an improvement in disorder severity. For example, effective neoplastic therapeutic agents prolong the survivability of the subject, inhibit the rapidly-proliferating cell growth associated with the neoplasm, or effect a regression of the neoplasm. Treatments that are therapeutically effective within the meaning of the term as used herein, include treatments that improve a subject's quality of life even if they do not improve the disease outcome per se.

"TNFR-Fc"—See "Etanercept."

"Treat," "treating," or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

"Vacuum" means pressures of 250 mTorr or less.

"Variant(s)" herein means a naturally occurring or synthetic version of, for instance, a protein that is structurally different from the original but related in structure and/or function, such as an allelic variant, a paralog, or a homolog of a protein.

DESCRIPTION OF THE INVENTION

The present invention relates to methods and compositions that provide protein therapeutic agents in high concentration for administration to a subject. In particular, in certain highly preferred embodiments of one of its aspects the invention provides stable preparations of protein therapeutic agents that reliably and rapidly can be reconstituted to high concentration formulations suitable and effective for subcutaneous administration. In preferred embodiments of the invention in this regard, the protein therapeutic agent is prepared by lyophilization, and the lyophilate is reconstituted for administration at a concentration of about 40 mg/ml or above.

In particular, in certain aspects and preferred embodiments thereof, the invention relates to methods for producing protein lyophilates (and to the lyophilates thereby produced) involving a lyophilization cycle as depicted in FIG. 1 comprising taking a sample (A), freezing it by lowering the temperature (B), maintaining it at a reduced temperature (C), raising the temperature (D), to an annealing temperature and annealing it by maintaining the annealing temperature (E), reducing the temperature after the annealing (F), holding the sample at a reduced temperature (G), raising the temperature to a first drying temperature (H), maintaining the sample for a period of time at the first drying temperature (I), raising the temperature to a second drying temperature (J), maintaining the sample at the second drying temperature (K), thereby producing a lyophilate (L) that, in particular, dissolves fully in suitable diluent, within 10 minutes, to provide a high protein concentration without visible foam, effervescence, turbidity, or particulate formation or settling.

I. Compositions and Reconstitution Thereof

A. Protein Lyophilates and Reconstitution Thereof

The invention herein disclosed, among other things, provides and is useful for preparing protein-containing compositions that are lyophilates that can be reconstituted at high concentrations in diluents suitable for veterinary and human therapeutic use, inter alia. Protein lyophilates of various aspects and embodiments of the invention in this regard are, as described herein, variously, lyophilate compositions wherein in three minutes or less after adding a diluent to said lyophilate: (a) the lyophilate is at least 90%+/−10% dissolved, (b) the height of foam above the resulting solution is less than 35% of the height of the foam above the solution plus the height of the solution, (c) there is no visible effervescence in the solution, and (d) the concentration of said protein in said diluent after reconstitution is at least 40 mg/ml.

In certain embodiments, in addition to any of the foregoing, within three minutes of adding the diluent: (a) the lyophilate is at least 90%+/−10% dissolved, (b) the height of the foam above the resulting solution is less than 25% of the height of the foam plus the height of the solution, and (c) there is visible effervescence in the solution and/or there are no visible bubbles in the solution.

In various embodiments, in addition to any of the foregoing, within three minutes of adding the diluent: (a) the lyophilate is at least 90%+/−10% dissolved, (b) the height of the foam above the resulting solution is less than 15% of the height of the foam plus the height of the solution, and (c) there is no visible effervescence in the solution.

In some embodiments, in addition to any of the foregoing, within three minutes of adding the diluent: (a) the lyophilate is at least 90%+/−10% dissolved, (b) the height of the foam above the resulting solution is less than 5% of the height of the foam plus the height of the solution, and (c) there is no visible effervescence in the solution.

In a variety of embodiments, instead of or in addition to any of the foregoing, within any of 1, 2, 3, 5 or 10 minutes of adding diluent: (a) the lyophilate is any of at least: 75, 85, 90, 93, 95, 97, 98, or 99% dissolved, (b) the height of the foam above the resulting solution is less than 3% of the height of the foam plus the height of the solution, and (c) there is no visible effervescence in the solution.

In various embodiments, in addition to any of the foregoing, the surface area of the lyophilate is equal to or greater than approximately any of 1.0, 1.1, 1.2, 1.3, or 1.4 m$^2$/gm. In various embodiments, in addition to any of the foregoing the surface area of the lyophilate is equal to or greater than any of approximately 10, 1.1, 1.2, 1.3, or 1.4 m$^2$/gm and equal to or less than any of approximately 1.5, 1.7, 2.0, 2.5, 3.0, 4.0, or 5.0 m$^2$/gm. In certain of the embodiments in this regard the surface area of the lyophilate is equal to or greater than 1.0 m$^2$/gm. In certain of the embodiments in this regard the surface area of the lyophilate is equal to or greater than 1.2 m$^2$/gm.

In many embodiments, in addition to any of the foregoing, addition of diluent results in a solution with a protein concentration of approximately 40 to 250 mg/ml. In various embodiments it is approximately 40 to 200 mg/ml. In certain embodiments it is approximately 75 to 150 mg/ml. In particular embodiments it is approximately 50 to 100 mg/ml.

In many embodiments, in addition to any of the foregoing, addition of diluent results in a solution with a protein concentration of 40 to 250 mg/ml. In various embodiments it is 40 to 200 mg/ml. In certain embodiments it is 75 to 150 mg/ml. In particular embodiments it is 50 to 100 mg/ml.

In various embodiments, in addition to any of the foregoing, the protein is stable in the compositions. In embodiments in this regard it is at least approximately any of 85, 90, 95, 97, 98, or 99% stable for at least any of approximately 3, 4, 5, 6, 9, 12, 18, or 24 months storage at any of approximately 4, 21, or 37° C. In particular embodiments it is at least approximately any of 85, 90, 95, 97, 98, or 99% stable for at least any of approximately 3, 4, 5, 6, 9, 12, 18, or 24 months storage at approximately 4° C. In certain embodiments it is at least approximately 95% stable for at least any of approximately 4, 5, 6, 9, 12, 18, or 24 months storage at approximately 4° C. In particular embodiments it is at least approximately 95% stable for at least approximately 12 months storage at 4° C.

With regard to any of the foregoing, stability in certain embodiments is measured by the fractional representation of the native "peak" of the intact form of the protein denominated by the total of "peaks" of the protein, in other words, the amount in the "main peak" divided by the total of the amounts in all peaks, including the main peak. The peaks in this sense may be peaks from an HPLC column, bands in gel or a blot, or other quantitative measures of the intact form of a protein and its breakdown products or aggregates or other forms indicative of instability.

In numerous embodiments, in addition to any of the foregoing, within any of 10, 5, 3, 2 or 1 minutes of adding diluent to the lyophilate there is no visible turbidity in the solution and/or there are no visible bubbles in the solution and/or there are no visible particles in the solution and/or the solution flows easily.

In numerous embodiments, in addition to any of the foregoing, the resulting solution is of sufficiently low viscosity to flow efficiently through a hypodermic needle of a gauge effective for subcutaneous injection into human subjects. In aspects and embodiments of the invention in this regard the viscosity of the solution is any of less than 10, 15, 20, 25, 30, 35, 40, 45, 50, 55, 60, 65, 70, 75, 80, 90, or 100 cP. For instance, in certain embodiments it is below 50 cP. In certain embodiments it is below 25 cP. In various other embodiments it is below 10 cP.

In various embodiments, in addition to any of the foregoing, the composition comprises any one or more of at least one bulking agent, and/or at least one stabilizing agent, and/or at least one surfactant In certain embodiments in this regard, in addition to any of the foregoing, the bulking agent is mannitol. In particular embodiments in this regard, the mannitol is comprised of polymorphs in the following amounts: equal to or greater than approximately 70% delta mannitol, equal to or less than approximately 20% mannitol hydrate, and equal to or less than approximately 10% amorphous mannitol. In various embodiments in this regard as well, the mannitol is comprised of polymorphs in the following amounts: equal to or greater than 70% delta mannitol, equal to or less than 20% mannitol hydrate, and equal to or less than 10% amorphous mannitol.

In certain embodiments, in addition to any one of the foregoing, the stabilizing agent is sucrose.

In various embodiments in addition to any of the foregoing, the surfactant is a polysorbate. In particular embodiments in this regard the concentration of the polysorbate is from 0.004% to 0.15%. In numerous embodiments in this regard, the surfactant is a polysorbate 80 or a polysorbate 20 in a concentration from 0.004% to 0.15%, In certain embodiments in addition to any of the foregoing, the surfactant is Pluronic F68. In particular embodiments in this regard the surfactant is Pluronic F68 in a concentration of 0.05% to 1.5%.

In certain embodiments, the composition comprises a buffer. In particular embodiments the buffer is a glutamate, citrate, succinate, phosphate, or acetate buffer. In certain embodiments the buffer is glutamate buffer. In particular embodiments the buffer is glutamate buffer in the range of pH 3.0 to 6.0. In certain embodiments the buffer is citrate buffer. In various embodiments it is citrate buffer in the range of pH 2.0 to 7.5. In certain embodiments it is succinate buffer. In various embodiments it is succinate buffer in the range of pH 3.0 to 7.0. In particular embodiments the buffer is phosphate buffer. In certain embodiments it is phosphate buffer in the range of pH 4.0 to 7.4. In various embodiments the buffer in acetate buffer. In particular embodiments it is acetate buffer in the range of pH 3.5 to 6.0.

In certain embodiments the protein is self-buffering. In particular embodiments the protein is self-buffering and the self-buffering action of the protein provides substantially all of the buffering capacity of the composition, at the desired pH. In particular embodiments the protein is self-buffering and buffers the composition in the range of pH 4.5 to pH 7.0. In all of these regards in certain embodiments the self-buffering action of the protein provides 90% or more of the buffering capacity of the composition.

In many embodiments, in addition to any of the foregoing, the protein is an agent for human therapeutic use or for veterinary use. In particular embodiments furthermore the protein is a pharmaceutical agent for human therapeutic use.

In certain embodiments in addition to any of the foregoing, addition of the diluent results in a solution comprising the protein at approximately 40 to 150 mg/ml, approximately 7 to 50 mM histidine, approximately 2% to 4% mannitol, approximately 1.0 to 2.5% sucrose, and approximately 0.004% to 0.015% polysorbate 20 or polysorbate 80, with pH 4.5 to 7.5. In particular embodiments in this regard, addition of the diluent results in a solution comprising the protein at approximately 40 to 150 mg/ml, approximately 20 mM histidine, approximately 3.3% mannitol, approximately 2% sucrose, and approximately 0.01% polysorbate 20 or polysorbate 80, with pH approximately 5.0. In further particular embodiments in this regard, addition of the diluent results in a solution comprising the protein at approximately 40 to 150 mg/ml, approximately 10 mM to 20 mM Tris, approximately 2.0% to 4.2% mannitol, approximately 0.5% to 2.5% sucrose, approximately 0.004% to 0.015% polysorbate 20 or polysorbate 80, at pH 4.5 to 7.6. In still further embodiments in this regard, addition of the diluent results in a solution comprising the protein at approximately 40 to 60 mg/ml, approximately 10 mM Tris, approximately 4% mannitol, approximately 2% sucrose, approximately 0.004% polysorbate 20 or polysorbate 80, at approximately pH 7.4. In additional further embodiments in this regard, addition of the diluent results in a solution comprising the protein at approximately 40 to 60 mg/ml, approximately 10 mM Tris, approximately 4% mannitol, approximately 1% sucrose, approximately 0.004% polysorbate 20 or polysorbate 80, at approximately pH 7.4.

Particular proteins and other aspects of compositions in accordance with the invention are described in greater detail below and elsewhere herein.

Reconstitution Procedure(s)

Lyophilized compositions in various aspects and embodiments of the invention may be reconstituted by a variety of methods, including, for instance, the procedures specified by a manufacturer and/or supplier for reconstituting a pharmaceutical protein-comprising lyophilate composition for veterinary or human use. In assessing various parameters of compositions as set forth herein, the specific instructions provided with a lyophilate are preferred procedures for reconstitution. Also among procedures for reconstitution are those described below and elsewhere herein.

For instance, lyophilized compositions in accordance herewith typically may be disposed within a lyophilization vial. Before addition of diluent, each vial for reconstitution is allowed to equilibrate to ambient temperature (typically room temperature). Equilibration time will depend on the initial temperature of the lyophilate, the ambient temperature for equilibration, whether the vial is stirred, whether the equilibration is by exposure to air or to a water bath, and other conditions. A standard equilibration time for analytical purposes is one hour at room temperature exposed to air. Vacuum in the vial, if any, is released, typically by inserting a high gauge needle, such as a 25G precision glide needle, through the septum. Diluent, such as USP sterile water for irrigation, which also has been equilibrated to the desired temperature, typically room temperature, is then introduced into the vial by syringe, again using a needle to puncture the septum. Generally, best results are obtained by introducing the diluent without touching the lyophilate. For timing reconstitution, a stop watch should be started as soon as the diluent is started into the vial. After the desired volume of diluent has been introduced, the vial is swirled gently for approximately 10 seconds, preferably 10 seconds.

As described below and elsewhere herein, reconstitution should be monitored under controlled conditions with a known intensity of light incident on the sample, against uniform black and uniform white backgrounds, as described below and elsewhere herein. In conjunction with visible inspection in this manner, the extent to which the protein in the lyophilate dissolves in the diluent may be monitored, often by optical absorbance at 280 nm (as described in greater detail below and elsewhere herein). Reconstitution time, as measured by $OD_{280}$, is defined, in certain embodiments, as the time in which for 90% plus or minus 7.5% of the protein in the lyophilate is dissolved in the diluent. Foam height, particulars, turbidity and other aspects of the resulting solution are determined and measured as described below and elsewhere herein.

B. Protein Concentration

Upon addition of a diluent and reconstitution, compositions in accordance with various aspects and embodiments of the invention provide, among other things, solutions of high concentration of lyophilized proteins. By high concentration in this regard is meant concentrations of or above 35 mg protein per ml of solution, preferably 40 mg/ml or above, especially preferably 50 mg/ml or above. It is to be appreciated that there are many measures of protein concentration that can be useful in accordance with the invention, including but not limited to: (A) Weight Percent (i)=weight of solute per 100 units of solvent volume; (B) Weight Percent (ii)=weight of solute per 100 units of solution volume; (C) Weight Percent (iii)=weight of solute per 100 units of solvent by weight; (D) Weight Percent (iv)=weight of solute per 100 units of solution by weight; (E) Weight Percent (v)=weight of solute in quantity of solvent ("qs") sufficient to bring the total volume to 100 units; (F) Weight Percent (vi)=weight of solute in quantity of solvent sufficient to bring the total weight to 100 units; (G) Mass Percent=mass of solute per 100 mass units of solution; (H) Mole Fraction=moles of solute per total moles of all components; (I) Molarity=moles of solute per liter of solution (i.e., solute plus solvent); (J) Molality=moles of solute per Kg of solvent; and (K) Volume Molality=moles of solute per liter of solvent. However, for simplicity and clarity, protein concentrations herein are expressed as mass/volume, typically mg/ml.

C. Rapid Reconstitution

The lyophilates, in a further particular embodiment, fully dissolve quickly in suitable diluents. In certain embodiments of the invention in this regard, protein lyophilates of the invention dissolve fully in 10 minutes or less, in certain preferred embodiments 5 minutes or less, in various particularly preferred embodiments 3 minutes or less, and in certain very particularly preferred embodiments 2 minutes or less.

By fully dissolved in this regard is meant that at least 90% of the protein in the lyophilate is dissolved. In certain preferred embodiments in this regard, 90%+/−10% or more of the protein is dissolved. In certain particularly preferred embodiments at least 97% of the protein is dissolved. And, in certain especially preferred embodiments of the invention in this regard substantially all of the protein is dissolved.

$OD_{280}$

A variety of methods may be employed to determine the degree of reconstitution of a lyophilate in accordance with this and with other aspects of the invention. For instance, as discussed further below, for a protein (or proteins) of known extinction coefficient, present in a known amount in a lyophilate and reconstituted in a known volume of a diluent, the degree of reconstitution can be determined by measuring optical absorbance at 280 nm, using well-known and routine techniques. Optical density determinations of this type will, of course, be effected by all the species that contribute to absorbance at 280 nm in the reconstituted solution.

Such problems often can be circumvented by determining the optical absorbance of the pre-lyophilization solution as the reference value for 100% reconstitution and then comparing the value for the reconstituted lyophilate with this value. The comparison must take into account, of course, any difference between the volume that was lyophilized to make the lyophilate and the volume into which the lyophilate was reconstituted.

To a first approximation, the contribution of the dry lyophilate to the volume of solution resulting from reconstitution often can be ignored, in which case the volume of the reconstituted lyophilate can be assumed to be the same as the volume of added diluent. However, where greater accuracy is required, the total volume of the reconstituted lyophilate should be determined and used in calculating the degree of reconstitution, rather than the volume of the added diluent.

With the foregoing two considerations taken into account, and other aspects of the determination being held constant, the ratio of the absorbance of the reconstituted lyophilate to the reference standard provides the fractional reconstitution of the lyophilate and, upon multiplication by 100, the percent reconstitution.

It is to be appreciated that the accuracy of optical density measurements is limited in routine laboratory practice and, generally, limits the accuracy in reconstitution determinations to plus and minus 5% of any particularly determined value. Care must be taken to achieve better accuracy.

Visual Inspection

A highly preferred method for determining the degree of reconstitution of a lyophilate is visual inspection, under carefully controlled conditions.

Among preferred methods for measuring foam height are visual/manual measurement methods such as the following. The vial containing the reconstituted lyophilate is observed under certain carefully controlled conditions. The light intensity at the sample should be approximately 2000 Lux. The solution should be observed against a uniform non-reflective white background and a uniform non-reflective black background for the appropriate period of time.

A suitable black background is a uniformly flat, uniformly black, uniformly non-reflective laminate, such as Home Depot UPC #724667060190 or equivalent thereof. A suitable white background is a uniformly flat, uniformly white, uniformly non-reflective laminate, such as Home Depot UPC #724667074234 or equivalent.

The sample and the viewing areas should be protected from stray light and thus should be enclosed to the extent possible, at least on the bottom and three sides (other than the back panel). Samples should be viewed so that the background for each is either entirely white or entirely black.

Notably, visual inspection is a well established quality control procedure in pharmaceutical manufacturing and, in particular, in the production of pharmaceutical products, such as lyophilates. Generally, procedures for visual inspection of pharmaceuticals are designed specifically to meet requirements specified by a regulatory authority concerned with the manufacture of drugs, such as the United States Food and Drug Administration ("USFDA"), and are specified in an operating protocol approved thereby. Certain such USFDA approved protocols for visual inspection of pharmaceutical products can be used in accordance with this aspect of the invention herein disclosed.

D. Foam Bubbles, Effervescence, Turbidity, and Particulates

In accordance with various aspects and embodiments of the invention in this regard, within 10 minutes or less of adding suitable diluent the resulting solution is substantially free of readily visible foam, effervescence, turbidity, and particulate formation and settling. In certain preferred embodiments in this regard, within 10 minutes of adding the diluent, the resulting solution is free of readily visible foam, effervescence, turbidity, and particulate formation and settling.

In certain particularly preferred embodiments of the invention further in this regard, within 5 minutes or less of adding suitable diluent the resulting solution is substantially free of readily visible foam, effervescence, turbidity and particulate formation and settling. In certain especially particularly preferred embodiments in this regard, within 3.5 minutes of adding the diluent the resulting solution is free of readily visible foam, effervescence, turbidity, and particulate formation and settling.

1. Foam. At the end of 10 minutes, preferably 5 minutes, more preferably 3 minutes, and especially preferably 2 minutes, in accordance with preferred embodiments of the invention, in this regard, the foam height is less than 35%, preferably 30% or, particularly preferably 25% or less, very particularly preferably 20% or less, very highly particularly preferably 15% or less, especially particularly preferably 10% or less, very especially particularly preferably 5% or less of the height of the foam plus the height of the solution resulting from addition of a diluent to the lyophilate.

In certain of the preferred embodiments in this regard the lyophilate is reconstituted with a standard volume of diluent, such as the manufacturer recommended diluent and diluent volume. In certain further preferred embodiments in this regard, the lyophilate is reconstituted in a standard size and shape container used for pharmaceutical lyophilate production, especially, for instance, a vial of the type used for etanercept lyophilates.

Foam Height Measurement

Foam height can be measured in accordance with the invention by a variety of methods using routine techniques that are well-known to those skilled in the arts to which the invention pertains.

Among preferred methods for measuring foam height are visual/manual measurement methods such as the following. The vial containing the reconstituted lyophilate is observed under certain carefully controlled conditions. The light intensity at the sample should be approximately 2000 Lux. The solution should be observed against a uniform non-reflective white background and a uniform non-reflective black background.

A suitable black background is a uniformly flat, uniformly black, uniformly non-reflective laminate, such as Home Depot UPC #724667060190 or equivalent thereof A suitable white background is a uniformly flat, uniformly white, uniformly non-reflective laminate, such as Home Depot UPC #724667074234 or equivalent.

The sample and the viewing areas should be protected from stray light and thus should be enclosed to the extent possible, at least on the bottom and three sides (other than the back panel). Samples should be viewed so that the background for each is either entirely white or entirely black.

With the container illuminated in accordance with the foregoing, the foam height is the distance between the top of the foam to the interface between the foam and the underlying liquid. The total height is measured from the top of the foam to the bottom of the underlying liquid (and thus is the total of the foam height plus the height of the underlying liquid). In an embodiment of the invention in this regard, heights are measured in this fashion using calipers.

2. Particulates. At the end of 10 minutes, preferably 5 minutes, more preferably 3 minutes, and especially preferably 2 minutes, in accordance with preferred embodiments of the invention, in this regard, particulates in the reconstituted formulation are characterized in that there are few visible particles and/or suspended particulates that barely decrease the clarity of the solution, preferably there are no visible particles but suspended particulates barely decrease clarity, equally preferably there are a few visible particles but suspended particulates have no visible effect on clarity, and most preferably there are no visible particles and the solution is clear.

Visible examination for particulates should be carried out under controlled conditions suitable for visual examination of pharmaceuticals, such as those described elsewhere herein.

3. Effervescence. At the end of 10 minutes, preferably 5 minutes, more preferably 3 minutes, and especially preferably 2 minutes, in accordance with preferred embodiments of the invention, in this regard, there is no visible effervescence. Most preferably there is no effervescence as a result of reconstitution.

Visible assessment of effervescence should be carried out under controlled conditions suitable for visual examination of pharmaceuticals, such as those described elsewhere herein.

4. Bubbles. At the end of 10 minutes, preferably 5 minutes, more preferably 3 minutes, and especially preferably 2 minutes, in accordance with preferred embodiments of the invention, in this regard, there are visible bubbles but their number, size, and distribution will not deleteriously affect reconstitution, stability, or dosing, preferably there are only one or two small visible bubbles that will not deleteriously affect reconstitution, stability, or dosing, and most preferably there are no visible bubbles.

Visible assessment for bubbles should be carried out under controlled conditions suitable for visual examination of pharmaceuticals, such as those described elsewhere herein.

5. Turbidity. At the end of 10 minutes, preferably 5 minutes, more preferably 3 minutes, and especially preferably 2 minutes, in accordance with preferred embodiments of the invention, in this regard, turbidity is present but it reduces transmittance by less than 20%, preferably by less than 10%, particularly preferably by less than 5%, especially preferably by less than 3%, and most especially preferably there is no visible turbidity.

Turbidity can be measured in accordance with the invention using well-known routine techniques and widely available instruments. For instance, turbidity can be measured using a Hach 2100 ANIS Laboratory Tubidimeter, typically using the following settings: Auto Range—on; Ration Option—off; Units—NTU; Signal Average—On. The instrument should have been calibrated within a month and reliable turbidity standards (zero and, for instance, NTU 20) should be used to set up the instrument. One suitable set of standards is Hach StablCal Calibration Set Catalog #26595-05 or equivalent.

Turbidity also can be gauged qualitatively by eye, using carefully controlled lighting and viewing conditions as described elsewhere herein, and appropriate turbidity standards for comparison. Other well-known and routine methods for measuring turbidity also can be used in the invention for this purpose.

E. Surface Area

Compositions in accordance with certain aspects and preferred embodiments of the present invention have a surface area following lyophilization that is equal to or greater than any of approximately 1.0, 1.1, 1.2, 1.3, or 1.4 $m^2/gm$. Among compositions in accordance with certain aspects and preferred embodiments of the invention in this regard are those having a surface area that is equal to or greater than any of 1.0, 1.1, 1.2, 1.3, or 1.4 $m^2/gm$. Further among compositions in this regard are those having a surface area that is equal to or greater than any of approximately 1.0, 1.1, 1.2, 1.3, or 1.4 $m^2/gm$ and equal to or less than any of approximately 1.5, 1.7, 2.0, 2.5, 3.0, 4.0, or 5.0 $m^2/gm$, including any combination of upper and lower bounds thereof. Additional compositions in accordance with certain aspects and embodiments further in this regard are those having a surface area that is equal to or greater than any of 1.0, 1.1, 1.2, 1.3 or 1.4 $m^2$/gm and equal to or less than any of 1.5, 1.7, 2.0, 2.5, 3.0, 4.0, or 5.0 $m^2$/gm, including any combination of upper and lower limits thereof. Among particular compositions in this regard are those having a surface area that is equal to or greater than approximately 1.0 $m^2$/gm, those having a surface area that is equal to or greater than approximately 1.2 $m^2$/gm, those having a surface area that is equal to or greater than 1.0 $m^2$/gm and those having a surface area that is equal to or greater than 1.2 $m^2$/gm.

Surface area as discussed herein is a measure of the accessible surface of a sample on a molecular level. Surface area in accordance with the invention in this regard can be determined using a variety of routine techniques well-known to those skilled in the arts to which the invention pertains. See, for instance, J. M. Smith, *Chemical Engineering Kinetics*, 3$^{rd}$ Ed., McGraw-Hill, Inc. (1981), especially Chapter 8, pages 327-348, especially Section 8-1 "Determination of Surface Area," which is incorporated herein by reference in its entirety particularly in parts pertinent to the determination of surface area, pore volume, mean pore radii, and related subject matter.

Methods of measuring surface area most often are based on Brunauer, Emmet, Teller theory (("BET"); but, some also are based on the Langmuir model. (See the foregoing references). Whether calculated using the BET or Langmuir models, surface area determinations for dispersed solids generally are based on measuring the quantity of an agent that binds a known quantity of the solid. The agent typically is one that adheres to surfaces in the solid with substantially uniform molecular density (i.e., molecules per unit surface area), so that the quantity of agent adhering to the sample provides an accurate measure of its surface area. The agent typically is in a form that can reach all of the accessible surfaces of the solid as well, usually a gas.

Commonly, surface areas are measured by methods generally in accordance with the following outline. Samples are first freed of adhering impurities, most often by heating, in vacuo or "under" a flowing stream of gas. The thus-prepared samples are then cooled, typically in liquid nitrogen. When cooled, the samples are exposed to a gas, typically nitrogen or krypton, at a series of set pressures. Krypton typically is used when the surface area is estimated to be 2 $m^2$/gm or less, as generally is the case for protein lyophilates. The amount of gas absorbed at each pressure is measured, and the surface area of the sample is derived from these measurements.

Preferred methods for measuring surface area of lyophilates in accordance with various aspects and embodiments of the invention in this regard include surface area determinations using a Micrometrics® ASAP 2020 Accelerated Surface Area and Porosimetry System in accordance with the manufacturer's instructions.

A typical procedure for measuring the surface area of a lyophilate in this regard is as follows. About 50 to 200 milligrams of lyophilized cake is thoroughly mixed with a mini spatula (which does not disturb the cake structure) and weighed into a round bottom tube. Using the degassing port on the ASAP 2020, the cake is degassed for 3 to 4 hours at 10 microns pressure and 30° C. Thereafter, the sample is accurately weighed. The surface area then is determined using krypton and the sample port of the ASAP 2020. Generally, five data points are obtained this way, and surface areas are calculated from the data using the BET equation.

Figure 5:
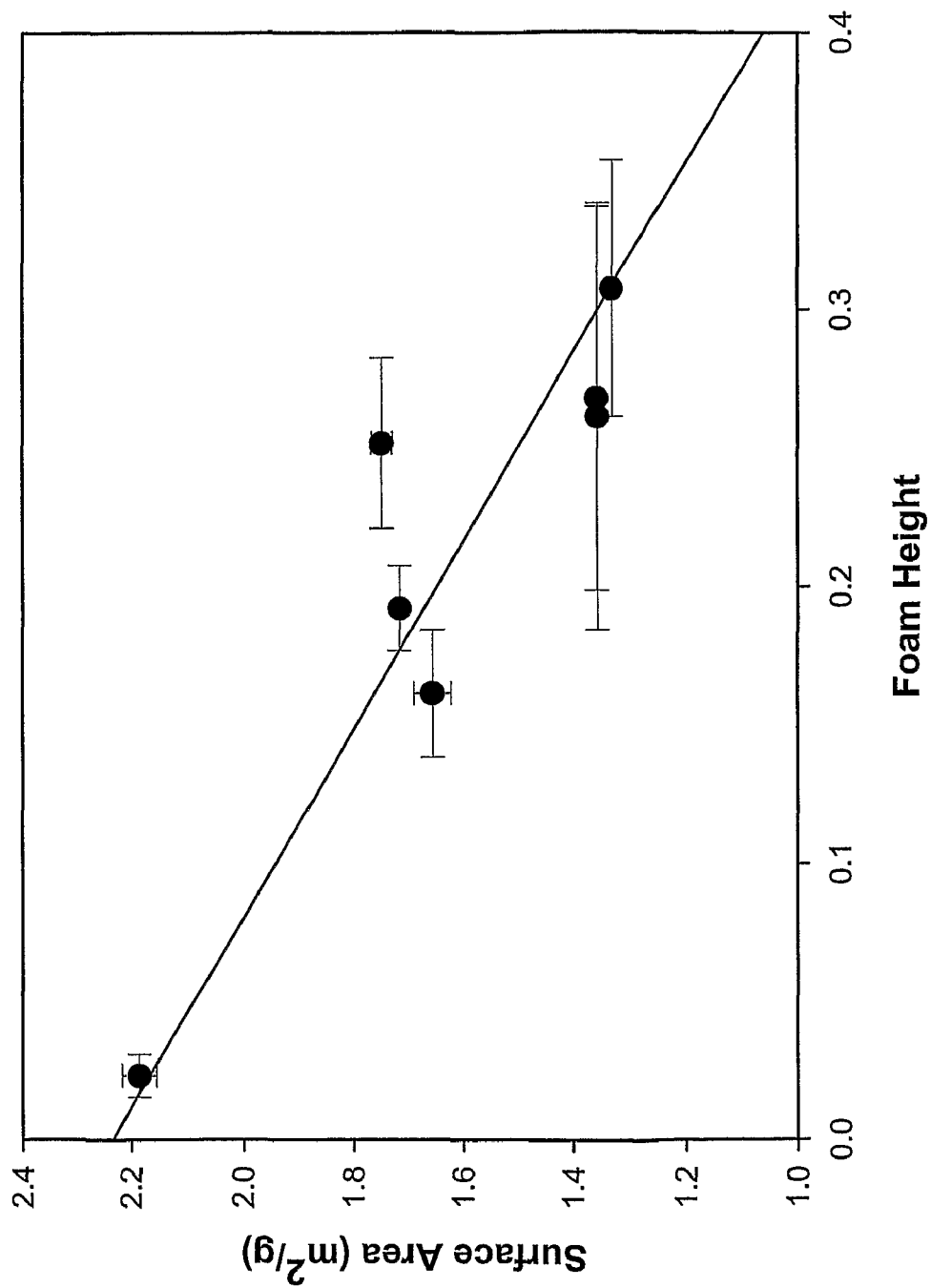
FIG. 5 is a graph showing the relationship between surface area and reconstitution properties.

FIG. 5 shows the relationship between BET surface areas for several related formulations. Surface areas were determined in accordance with the foregoing. Foam heights were determined as described elsewhere herein.

F. Polymorphs and Crystallinity

Crystallinity of components of a lyophilate can have a significant effect on preservation of protein activity during lyophilization and on protein stability in a stored lyophilate over time. Accordingly, certain aspects and embodiments of the invention provide compositions and methods for producing the compositions in which the occurrence and/or distribution of polymorphs of one or more components therein are optimized to prevent protein damage and ensure protein integrity during lyophilization and to prevent protein damage and ensure protein integrity upon storage, particularly upon storage in the lyophilized state.

Aspects and embodiments of the invention in this regard are illustrated by optimization of mannitol polymorphs in compositions. In accordance therewith, for instance, in certain compositions of the invention comprising mannitol, in addition to a protein lyophilate, the mannitol is at least approximately 70% delta mannitol, not more than approximately 20% mannitol hydrate and not more than approximately 10% amorphous mannitol. In preferred embodiments in this regard, plus and minus the mean experimental error in determining the relative amounts of mannitol hydrates in a sample, the mannitol in the lyophilate composition is at least 70% delta mannitol, not more than 20% mannitol hydrate and not more than 10% amorphous mannitol. In addition, in various other embodiments in this regard, the mannitol is at least 65, 60, 55, or 50% delta mannitol, not more than, respectively, 12.5, 17.5, 22.5, or 27.5% mannitol hydrate and not more than, respectively, 22.5, 27.5, 32.5, or 37.5% amorphous mannitol. (That is: $\geq 65/\leq 12.5/\leq 22.5$; $\geq 60/\leq 17.5/\leq 27.5$; $\geq 55/\leq 22.5/\leq 32.5$; $\geq 50/\leq 27.5/\leq 37.5$, wherein/means "and", and ";" separates different sets of the parameters that apply, and all numbers are percentages.) Methods for determining polymorphs, such as, in particular mannitol polymorphs and their optimum distributions in a lyophilate composition, are described below.

Optimum crystallinity can be determined using a variety of well-known techniques, including X-ray diffraction ("XRD"), FT-IR, differential scanning calorimetry ("DSC") and Raman spectroscopy. See, for instance, Burger et al., "Energy/temperature Diagram and Compression Behavior of the Polymorphs of D-Mannitol," *J. Pharm. Sci.* 89(4): 457-468 (2000) regarding XRD, FT-IR, DSC and Raman methods in this regard, Walter-Ley, L., "Crystallochimie-Sur les varieties cristallines du D-mannitol," *C. R. Acad. Sci., Paris, Ser C.* 267: 1779-1782 (1968) regarding XRD methods, Izutso et al. "Effect of Mannitol Crystallinity on the Stabilization of Enzymes during Freeze Drying," *Chem. Pharm. Bull.* 42(10 5-8 (1994) regarding XRD and DSC, and Vehring, R., "Red-Excitation Dispersive Raman Spectroscopy is a Suitable Technique for Solid-State Analysis of Respirable Pharmaceutical Powders," *Applied Spectroscopy* 59(3) 286-292 (2005) regarding Raman spectroscopy, each of which is incorporated herein by reference in its entirety particularly in parts pertinent to XRD, FT-IR, DSC, and Raman spectroscopy and their use to determine polymorphs in lyophilates in particular in accordance with various aspects and embodiments of the invention herein disclosed.

Each of these techniques has its advantages, and some disadvantages as well. Using them to analyze structures in numerous samples to determine optimum conditions for lyophilization can be a substantial undertaking, although not involving undue experimentation or effort. Furthermore, present XRD, DSC, and Raman methods are not able accurately to quantify and/or discriminate certain structures.

The inventors have developed a quantitative real time Raman spectroscopy method for determining polymorphs of lyophilate components. The method uses a Partial Least Squares ("PLS") algorithm to quantify the different polymorphs of compounds in a sample. In contrast to prior art methods, which rely typically on discrete individual "signature" frequencies and internal standards to distinguish and quantify polymorphic forms of a compound, the method developed by the present inventors utilizes a broad range Raman spectrum for each polymorph, to distinguish them from one another and to quantify them, without requiring an internal standard. Utilizing a broad spectrum for each polymorph, and a PLS algorithm for analysis better discriminates between polymorphs and improves quantitative accuracy over prior art methods. Moreover, because it does not require an internal standard, the present method avoids substantial errors caused by instability of internal standards and/or non-uniformity in the distribution of an internal standard in a sample. The method is described in greater detail below, and illustrated by its application to the analysis of Mannitol polymorphs in high concentration protein lyophilates By way of introduction, Vehring (cited above) showed that crystalline mannitol polymorphs can be distinguished from one another and quantified using an internal standard, albeit with somewhat limited accuracy, by Raman spectroscopic frequencies. The use of an internal standard necessitated the addition of the standard to the sample, and necessarily incurred the drawbacks mentioned above. Furthermore, Vehring used single peak intensities for calibration and intensity, necessarily limiting the ability of the method to distinguish method polymorphs and its quantitative accuracy.

Vehring identified particular frequency lines that differ between mannitol polymorphs. That is, the contribution of the polymorphs were deconvoluted from the Raman spectra of samples by iteratively minimizing the residuals of marker peaks (i.e., spectral line frequencies) that were selected as signatures of the individual polymorphs. The signature frequencies were selected by analyzing each polymorph by itself (or in a mixture of known components and proportions). Relying on one signature frequency for each polymorph limits the ability of the method to discriminate between and quantify the polymorphs.

The use of Raman spectroscopy for the determination polymorphs also has been described by Roberts et al., "Quantitative Analysis of Mannitol Polymorphs: FT-Raman Spectroscopy," *J. Pharma. Biomed. Analysis* 28(6): 1135-1147 (2002) and by Auer et al., "Qualitative and quantitative study of polymorphic forms in drug formulations by near infrared FT-Raman spectroscopy," *J. Molec. Structure* 661: 307-317 (2003) each of which is incorporated herein by reference in its entirety particularly in parts pertinent to the determination of polymorphs in lyophilates in accordance with various aspects and embodiments of the present invention.

The present method, in contrast, utilizes a broad range spectrum for each polymorph for discrimination and for quantification. Polymorphs are discriminated and quantified by deconvoluting the sample spectrum using a Partial Least Squares algorithm. In brief, the method involves: obtaining a Raman spectrum for each polymorph over a broad range; normalizing the Raman spectra against their C—H stretch band at about 2800 cm$^{-1}$; deriving derivative spectra from the normalized spectra; computationally simulating a calibration set of spectra by linear addition of the normalized derivative spectra; generating a quantitation procedure using the Partial Least Squares algorithm and the calibration set; and then applying the procedure to the Raman spectrum of a sample to calculate the relative amounts of the polymorphs therein. (Partial Least Squares analysis is described in Wold, H., "The Fix Point Approach to Independent Systems, North-Holland," Amsterdam (1981) and Geladi et al., "Partial Least-Squares Regression: A Tutorial," *Anal. Chim. Acta* 185: 1-17 (1986), each of which is incorporated herein by reference in its entirety particularly in parts pertinent to the use of PLS for analysis of polymorphs in a sample. In the present method polymorphs are quantified by regression vectors that are derived from the spectra obtained from a sample. The regression vectors are generated from selected latent variables using a spectral matrix. The matrix is generated from calibration standards: converged regression vectors generated from the calibration are used to predict a set of pseudo-probabilities from the sample spectra. The sum of the pseudo-probabilities for all possible identities for the spectra is equal to one.

For instance, for mannitol a set of simulated Raman spectra is used for calibrating the PLS program to calculate the regression vectors between the matrix of Raman spectra and the matrix of percentages for the five mannitol forms. The calibration spectra are generated by linear addition of the processed Raman spectra for each pure polymorph (based on their percentages). This procedure avoids bias and variance arising from non-uniform distribution and instability of calibration standards in samples, problems which beset traditional methods.

It is assumed that the Raman cross sections of all C—H stretch-related modes are the same for all of the polymorphs, and that the interaction between different polymorphs is negligible. Given the first assumption, the normalized spectra for the polymorphs will have the same C—H mode integration intensity at 2800 cm$^{-1}$. Given the first assumption, the 2800 cm$^{-1}$ peak integral will fix the relationship between Raman peak intensity and the percentage of each polymorph in the sample. Given the second assumption, the Raman spectrum of polymorphs in a sample will be the linear addition of the Raman spectra of the individual polymorphs in the sample. The regression factor is obtained from normalized second derivative spectra. Normalization removes the error that would be caused by absolute peak fluctuation. Use of second derivative spectra reduces the effect of Raman background intensity.

In accordance with various embodiments of the present method, the effects of grating drift can be removed using a grating drift correction algorithm. Typical correction algorithms in this regard are based on a measured drift value that is used to derive corrected pixel value by, for instance, a linear curve fit to the two adjacent data points. The drift value may be derived from measurements of the Raman spectra of two standards, such as neon and acetaminophen, taken under two conditions, with the same settings. In order to filter out the variance associated with absolute peak intensity and spectral background, normalized second derivative Raman spectra are obtained for both standards. Linear curve fitting is based on two consecutive data points. The drift value obtained from previous steps gives the corrected pixel value of raw drifted spectra.

G. Proteins

The invention herein disclosed may be practiced with practically any protein. It is applicable in particular to proteins of therapeutic significance in veterinary and/or human therapeutic applications. The specific procedures and formulations of the invention pertaining to any particular such protein often will be generic; but, in many cases also may be unique. In particular, proteins that are not soluble in water and those that spontaneously form water insoluble aggregates may not be adaptable to the general methods of the present invention disclosed herein, and may require specialized procedures to adapt them to the present methods. Likewise, proteins that are prone to irreversible loss of activity when dried (as by lyophilization) also may require specialized procedures for use in the present invention. The development of such methods, while it may require significant experimentation, should be very considerably effectuated by the information provided herein and knowledge of the structural features of the proteins that cause insolubility and/or aggregation. Thus, it will be within the skill of those in the art to develop such methods, in view of the guidance herein provided, without undue experimentation.

While virtually any protein can be utilized in accordance with the invention herein disclosed, certain types of proteins are preferred. In particular, proteins with good solubility in water and those that do not have a strong propensity spontaneously to form insoluble aggregates are preferred.

Preferred proteins of the invention include those that are a veterinary or human therapeutic pharmaceutical agent, especially therapeutic pharmaceutical agents.

Preferred proteins of the invention particularly include proteins that bind selectively to specific targets, including ligand-binding proteins and protein ligands. Antigen-binding proteins, proteins derived therefrom, and proteins related thereto are among the particularly preferred embodiments of the invention in this regard. Highly preferred proteins of the invention in this regard are antibodies and proteins derived from antibodies or incorporating antibodies, in whole or part, including, to name just a few such entities: monoclonal antibodies, polyclonal antibodies, genetically engineered antibodies, hybrid antibodies, bi-specific antibodies, single chain antibodies, genetically altered antibodies, including antibodies with one or more amino acid substitutions, additions, and/or deletions (antibody muteins), chimeric antibodies, antibody derivatives, antibody fragments, which may be from any of the foregoing and also may be similarly engineered or modified derivatives thereof, fusion proteins comprising an antibody or a moiety derived from an antibody or from an antibody fragment, which may be any of the foregoing or a modification or derivative thereof, conjugates comprising an antibody or a moiety derived from an antibody, including any of the foregoing, or modifications or derivatives thereof, and chemically modified antibodies, antibody fragments, antibody fusion proteins, and the like, including all of the foregoing.

Especially preferred ligand binding moieties in this regard are the TNF binding moieties of TNF receptor, especially the TNFalpha binding moieties of TNFalpha receptors, particular those of a human TNFalpha receptor, most especially the TNF binding moiety in etanercept.

Especially preferred ligands in this regard are IL-1 receptor antagonists that bind IL-1 receptors. Especially highly preferred in this regard is the IL-1 antagonist IL-1ra and proteins derived therefrom or functionally homologous thereto.

Very especially highly preferred in this regard are IL-1 receptor antagonist moieties derived from IL-1ra. In particular, the IL-1ra-derived polypeptide sequence of Fc-IL-1ra is very highly especially particularly preferred in certain embodiments of the invention in this regard.

Among the most very highly preferred proteins of the invention in this regard are the TNFR-Fc fusion proteins and IL-1ra-Fc fusion proteins. Among the most highly preferred embodiments in this regard are etanercept and Fc-IL-1ra.

Also among preferred proteins of the invention in these regards are those described below.

1. Antibodies and Antibody-Related Proteins

Among particularly preferred proteins in accordance with the invention are antibody polypeptides, such as heavy and light chain polypeptides that have the same amino acid sequence as those that occur in and make up naturally-occurring antibodies, such as those that occur in sera and antisera, including such polypeptides and proteins isolated from natural sources, as well as those that are made by hybridoma technologies, by activation of an endogenous gene (by homologous or non-homologous recombination, for instance), by expression of an exogenous gene under the control of an endogenous transcription control region, by expression of an exogenous expression construct, by semi-synthesis and by de novo synthesis, to name some techniques commonly employed for making antibodies and antibody-related polypeptides and proteins that can be used to produce antibody polypeptides and proteins in accordance with the invention.

Included among these antibody-related polypeptides and proteins are those in whole or part having a de novo amino acid sequence, those that comprise all or one or more parts of an antibody (that is: a continuous chain of amino acids having the same sequence as any four or more residues in the amino acid sequence of a naturally occurring antibody polypeptide), those having an amino acid sequence that matches in some way that of a naturally occurring antibody, but differs from it in other ways, those that have the same but different amino acid sequences as a naturally occurring counterpart or sequence relating thereto, but differ from the counterpart in one or more post-translational modifications, and those comprised in part of any of the foregoing (in part or in whole) fused to one or more polypeptide regions that can be of or derived from or related to a second, different antibody polypeptide, and can be of or derived from any other polypeptide or protein, whether naturally occurring, resembling but differing therefrom, having a semi-de novo amino acid sequence and/or a de novo sequence, among others. Such hybrids are generally referred to herein as fusion polypeptides and/or fusion proteins.

Further among preferred proteins in accordance with the invention herein described are modified proteins in accordance with all of the foregoing. Included among such modified proteins are proteins modified chemically by a non-covalent bond, covalent bond, or both a covalent and non-covalent bond. Also included are all of the foregoing further comprising one or more post-translational modifications which may be made by cellular modification systems or modifications introduced ex vivo by enzymatic and/or chemical methods, or introduced in other ways.

Among preferred proteins of the invention in this regard are Fab fragment(s), such as those produced by cleaving a typical dimeric $(LH)_2$ antibody with certain protease that leave the light chain intact while cleaving the heavy chains between the variable region and the adjacent constant region, "above" the disulfide bonds that hold the heavy chains together. Such cleavage releases one Fc fragment comprising the remaining portions of the heavy chains linked together, and two dimeric Fab fragments each comprising an intact light chain and the variable region of the heavy chain. Fab fragments also can be produced by other techniques that do not require isolation of a naturally occurring antibody and/or cleavage with a protease.

Also preferred are $Fab_2$ fragment(s) such as those produced in much the same manner as Fab fragments using a protease that cleaves "between or below" the disulfide bonds. As a result, the two Fab fragments are held together by disulfide bonds and released as a single $Fab_2$ fragment. $Fab_2$ fragments can be produced by many other techniques including those that do not require isolation of an intact antibody or cleavage with a protease having the required specificity. Furthermore, both mono- and bi-specific Fab$_2$ fragments can now be made by a variety of routine techniques.

Also among preferred proteins in this regard are Fab$_3$ fragments, which are engineered antibody fragments in which three Fab fragments are linked together. Fab$_3$ fragments can be mono-, bi-, or tri-specific. They can be made in a variety of ways well-known to those of skill in the pertinent arts.

Among other preferred proteins in this regard are Fc fragments(s), such as those produced by cleavage with a protease in the same manner used for the production of either Fab fragments or Fab$_2$ fragments. However, for the production of Fc fragments, the dimeric heavy chain containing fragments are isolated rather than the light chain containing fragments. Fc fragments lack antigen combining sites, but comprise effector regions that play a role in physiological processes involving antibodies. Fc fragments can be made by a variety of techniques that are well-known and routinely employed by those of skill in the art for this purpose.

Among other preferred proteins in this regard are single-chain variable fragments ("scFv(s)"). scFv(s) are fusion proteins made by joining the variable regions of the heavy and light chains of an immunoglobulin. The heavy and light chains in an scFv typically are joined by a short serine, glycine linker. scFv(s) have the same specificity as the antibodies from which they were derived. Originally produced through phage display, scFv(s) now can be made by a variety of well-known methods.

Also preferred are Bis-scFv(s) which are fusions of two scFv(s). Bis-scFv(s) can be mono- or bi-specific. A variety of methods are well-known and can be applied in making Bis-scFv(s) in accordance with the invention.

Also preferred in accordance with the invention in this regard are minibodies; mono- and bi-specific diabodies; mono-, bi-, and tri-specific triabodies; mono-, bi-, tri-, and tetra-specific tetrabodies; VhH domains; V-NAR domains; V$_H$ domains; V$_L$ domains; camel Igs; Ig NARs; and others.

Also among preferred embodiments in accordance with various aspects and preferred embodiments of the invention in these and other regards are proteins comprising one or more CDR and/or CDR-derived and/or CDR-related regions of an antibody or one or more FR and/or FR-derived and/or FR-related regions of an antibody. In this regard CDR means complementary determining region; that is, a hypervariable region of a light or heavy chain of an antibody, typically about 9 to 12 amino acids in length that usually is an important part of an antigen specific binding moiety of an antibody. FR in this regard means a framework region of an antibody; that is, a region of about 15 to 20 amino acids that separates CDRs in the antigen specific binding moiety of an antibody. The terms CDR-derived and CDR-related, and the terms FR-derived and FR-related have the same meanings as to CDR and FR, respectively, as set forth in the above Glossary for the terms antibody-derived and antibody-related as to the term antibody.

Regarding antibodies, antibody-derived, and antibody-related proteins in accordance with the foregoing and with other aspects of the invention herein disclosed, see, for instance, *Protein Engineering: Principles and Practice*, Jeffrey L. Cleland and Chares S. Craik, eds. Wiley-Liss, Inc., New York (1996), particularly therein Kelley, Robert F., "Engineering Therapeutic Antibodies," Chapter 15, pp. 399-434 and Hollinger, P. & Hudson, P., "Engineered antibody fragments and the rise of single domains," *Nature Biotechnology*, September 2005, 1126-1136, each of which is herein incorporated by reference in its entirety particularly in parts pertinent to the structure and engineering of antibodies, particularly biopharmaceutical antibodies, and antibody-derived and antibody-related proteins, particularly antibody-derived and antibody-related pharmaceutical proteins in accordance with the invention herein described.

As to all of the foregoing, particularly preferred in the invention are human, humanized, and other proteins that do not engender a significantly deleterious immune response when administered to a human. Also preferred in the invention are proteins in accordance with all the foregoing that similarly do not cause a significantly deleterious immune response on administration to non-humans.

Among very particularly preferred proteins in accordance with the invention in these regards are fusion proteins comprising antibodies and/or antibody-derived proteins, polypeptides, or fragments or the like, including all of those described above. Among very particularly preferred fusion proteins of the invention in this regard are fusion proteins comprising an antibody or antibody-derived protein or fragment such as those described above and a ligand-binding moiety, such as those illustratively described herein.

2. Target Binding Proteins

Also among preferred proteins of the invention in this regard are antibodies and other types of target binding proteins, and proteins relating thereto or derived therefrom, and protein ligands, and proteins derived therefrom or relating thereto. Among especially preferred ligand-binding proteins in this regard are proteins that bind signal and effector proteins, and proteins relating thereto or derived therefrom.

Among such binding proteins, including antibodies, including proteins derived therefrom and proteins related thereto, are those that bind to one or more of the following, alone or in any combination:

(a) CD proteins including but not limited to CD3, CD4, CD8, CD19, CD20, and CD34;

(b) HER receptor family proteins, including, for instance, HER2, HER3, HER4, and the EGF receptor;

(c) cell adhesion molecules, for example, LFA-1, Mol, p 150, 95, VLA-4, ICAM-1, VCAM, and alpha v/beta 3 integrin;

(d) growth factors, including but not limited to, for example, vascular endothelial growth factor ("VEGF"); growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), nerve growth factor, such as NGF-beta, platelet-derived growth factor (PDGF), fibroblast growth factors, including, for instance, aFGF and bFGF, epidermal growth factor (EGF), transforming growth factors (TGF), including, among others, TGF-alpha and TGF-beta, including TGF-beta1, TGF-beta2, TGF-beta3, TGF-beta4, or TGF-beta5, insulin-like growth factors-I and -II (IGF-I and IGF-II), des(1-3)-IGF-I (brain IGF-I), and osteoinductive factors;

(e) insulins and insulin-related proteins, including but not limited to insulin, insulin A-chain, insulin B-chain, pro-insulin, and insulin-like growth factor binding proteins;

(f) coagulation and coagulation-related proteins, such as, among others, factor VIII, tissue factor, von Willebrands factor, protein C, alpha-1-antitrypsin, plasminogen activators, such as urokinase and tissue plasminogen activator ("t-PA"), bombazine, thrombin, and thrombopoietin;

(g) colony stimulating factors (CSFs), including the following, among others, M-CSF, GM-CSF, and G-CSF;
(h) other blood and serum proteins, including but not limited to albumin, IgE, and blood group antigens;
(i) receptors and receptor-associated proteins, including, for example, flk2/flt3 receptor, obesity (OB) receptor, growth hormone receptors, and T-cell receptors;
(j) neurotrophic factors, including but not limited to, bone-derived neurotrophic factor (BDNF) and neurotrophin-3, -4, -5, or -6 (NT-3, NT-4, NT-5, or NT-6);
(k) relaxin A-chain, relaxin B-chain, and prorelaxin;
(l) interferons, including for example, interferon-alpha, -beta, and -gamma;
(m) interleukins (ILs), e.g., IL-1 to IL-10;
(n) viral antigens, including but not limited to, an AIDS envelope viral antigen;
(o) lipoproteins, calcitonin, glucagon, atrial natriuretic factor, lung surfactant, tumor necrosis factor-alpha and -beta, enkephalinase, RANTES (regulated on activation normally T-cell expressed and secreted), mouse gonadotropin-associated peptide, DNAase, inhibin, and activin;
(p) integrin, protein A or D, rheumatoid factors, immunotoxins, bone morphogenic protein (BMP), superoxide dismutase, surface membrane proteins, decay accelerating factor (DAF), AIDS envelope, transport proteins, homing receptors, addressins, regulatory proteins, immunoadhesins, antibodies; and
(q) biologically active fragments or variants of any of the foregoing.

As to all of the foregoing, particularly preferred are those that are effective therapeutic agents, particularly those that exert a therapeutic effect by binding a target, particularly a target among those listed above, including targets derived therefrom, targets related thereto, and modifications thereof.

3. Particular Illustrative Proteins

Figure 2:
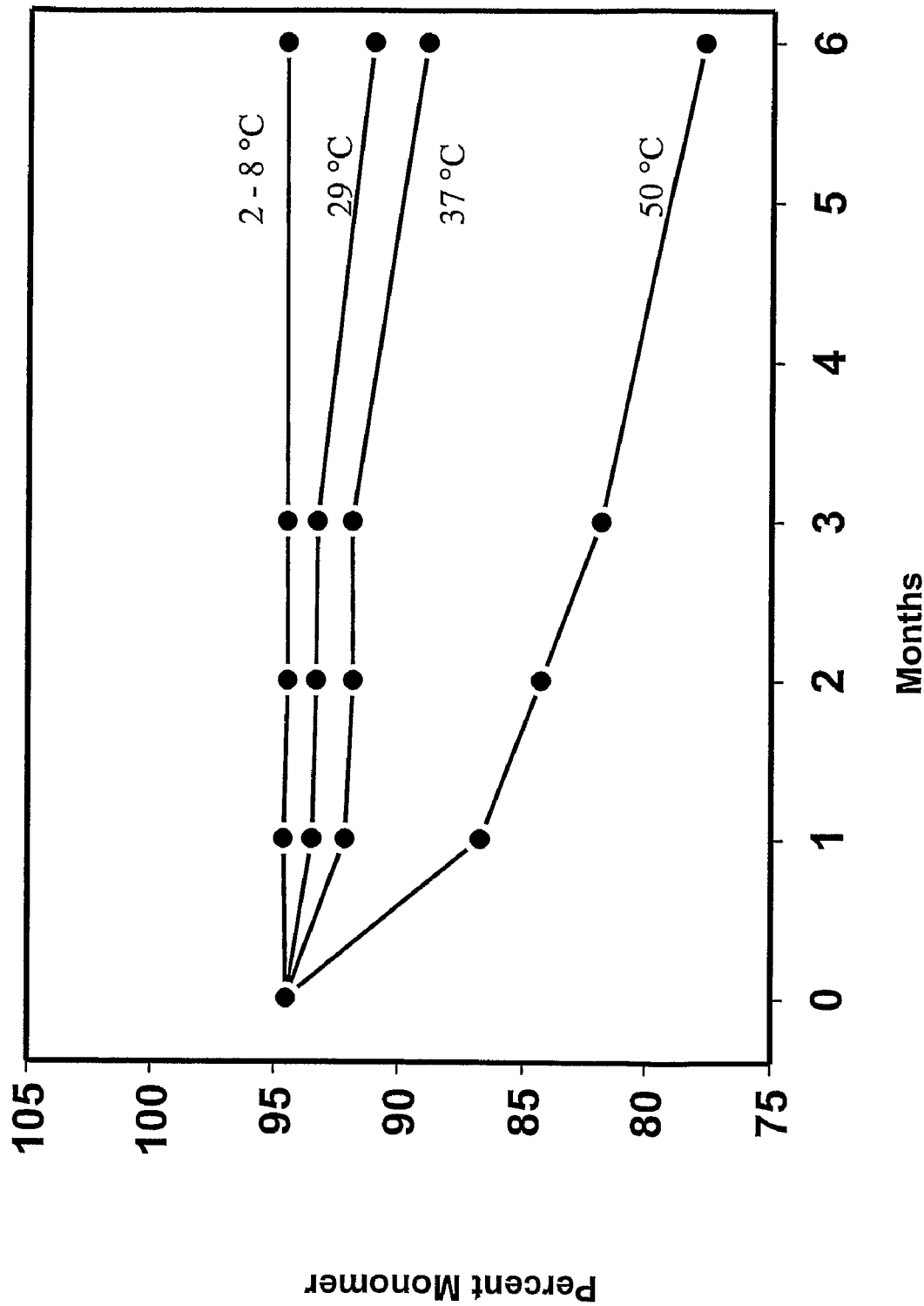
FIG. 2 is a chart showing the stability of lyophilized etanercept determined as described in Example 26.
Figure 4:
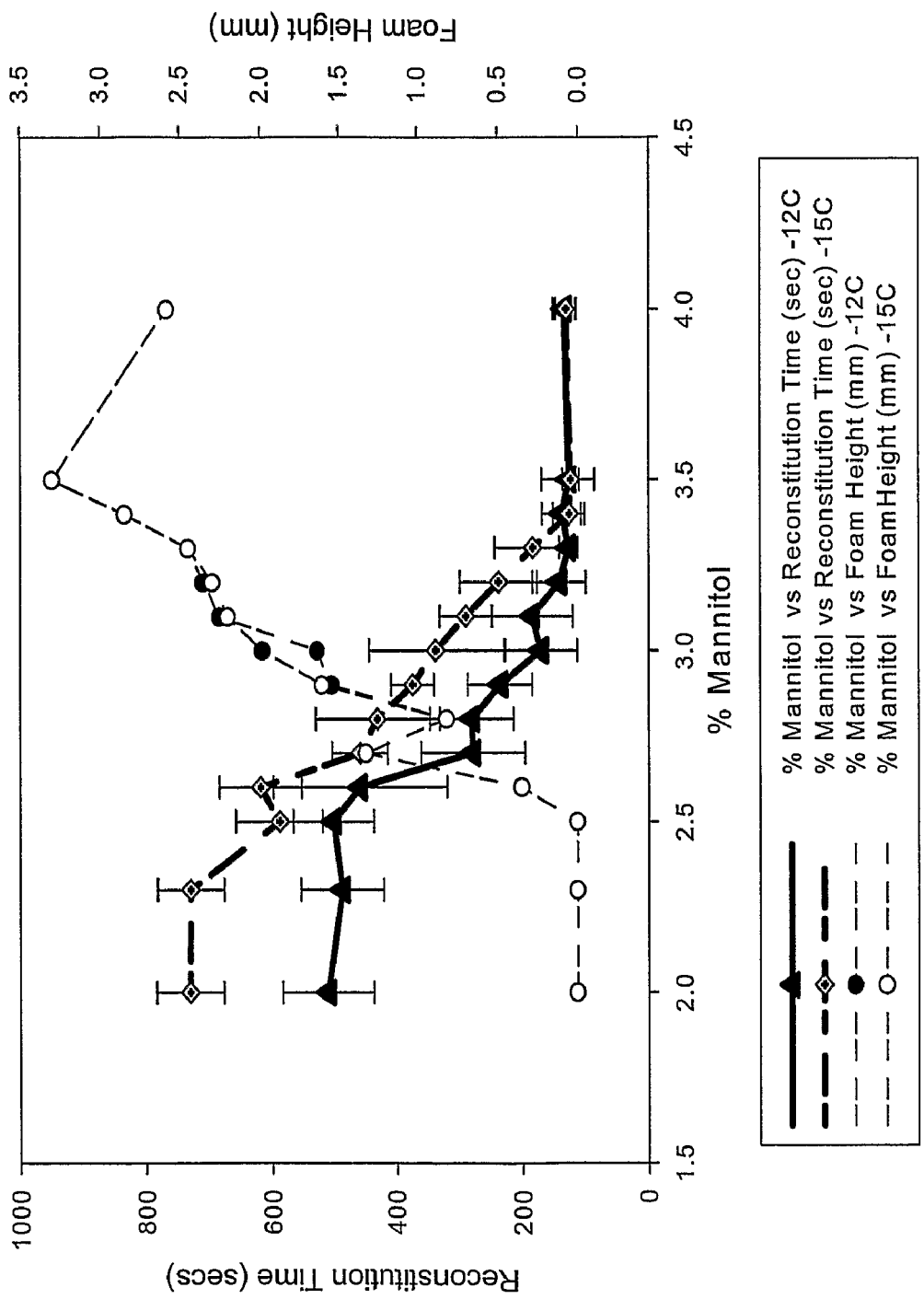
FIG. 4 is a chart showing reconstitution time and foam height as a function of mannitol concentration for lyophilate compositions comprising the protein prepared with annealing temperatures of −12° C. and −15° C. Mannitol is indicated on the horizontal axis at the bottom of the graph. Reconstitution time is indicated in seconds on the left vertical axis. Foam height is indicated as a percentage of total height (volume plus foam) on the right vertical axis. Filled circles indicate foam height data for annealing at −12° C. Open circles indicate foam height data for annealing at −15° C. Triangles indicate reconstitution time data for annealing at −12° C. Diamonds indicate reconstitution time data for annealing at −15° C.

Among particular illustrative proteins are certain antibody and antibody-related proteins, including peptibodies, such as, for instance, those listed immediately below and elsewhere herein:

OPGL specific antibodies and peptibodies and the like (also referred to as RANKL specific antibodies, peptibodies and the like), including fully humanized and human OPGL specific antibodies, particularly fully humanized monoclonal antibodies, including but not limited to the antibodies described in International Publication Number WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication.

Myostatin binding agents or peptibodies, including myostatin specific peptibodies, particularly those described in US Application Publication Number 2004/0181033, which is incorporated by reference herein in its entirely particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in its entirety fully as disclosed in the foregoing publication.

IL-4 receptor specific antibodies, particularly those that inhibit activities mediated by binding of IL-4 and/or IL-13 to the receptor, including those described in International Publication No. WO 2005/047331 of International Application Number PCT/US2004/03742, which is incorporated herein by reference in its entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L213; L2H14; L3H1; L4H1; L5H1; L6H1, each of which is individually and specifically incorporated by reference herein in its entirety fully as disclosed in the foregoing publication.

Interleukin 1-receptor 1 ("IL-1-R1") specific antibodies, peptibodies and related proteins and the like, including but not limited to those described in U.S. Application Publication Number US2004/097712A1 which is incorporated herein by reference in its entirety in parts pertinent to IL-1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. application publication.

Ang2 specific antibodies and peptibodies and related proteins and the like, including but not limited to those described in International Publication Number WO 03/057134 and U.S. Application Publication Number US2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1 (N) WT; Con4 (N), Con4 (N) 1K WT, 2×Con4 (N) 1K; L1 (C); L1 (C) 1K; 2×L1 (C); Con4 (C); Con4 (C) 1K; 2×Con4 (C) 1K; Con-4-L1 (N); Con-4-L1 (C); TN-12-9 (N); C17 (N); TN8-8 (N); TN8-14 (N); Con 1 (N), also including anti-Ang 2 antibodies and formulations such as those described in International Publication Number WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1KAb1P; and Ab1P, in their various permutations as described therein, each of which is individually and specifically incorporated by reference herein in its entirety fully as disclosed in the foregoing publication.

NGF specific antibodies, including, in particular, but not limited to those described in U.S. Application Publication Number US2005/0074821, which is incorporated herein by reference in its entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication.

CD22 specific antibodies and related proteins, such as those described in U.S. Pat. No. 5,789,554 which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0.

IGF-1 receptor specific antibodies and related proteins such as those described in International Patent Application Number PCT/US2005/046493, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, and L52H52, each of which is individually and specifically incorporated by reference herein in its entirety fully as disclosed in the foregoing International Application.

B-7 related protein 1("B7RP-1") specific antibodies, (B7RP-1 also is referred to in the literature as B7H2, ICOSL, B7h, and CD275) particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Provisional Application No. 60/700,265, filed 18 Jul. 2005, which is incorporated herein by reference in its entirety as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 431H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Provisional Application.

IL-15 specific antibodies, peptibodies and related proteins, such as, in particular, humanized monoclonal antibodies, particularly antibodies such as those disclosed in U.S. Application Publication Numbers: US2003/0138421; US2003/023586; and US2004/0071702, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7.

IFN gamma specific antibodies, especially human IFN gamma specific antibodies, particularly fully human anti-IFN gamma antibodies, such as, for instance, those described in U.S. Application Publication Number US2005/0004353, which is incorporated herein by reference in its entirety as to IFN gamma specific antibodies, particularly, for example, the antibodies therein designated 1118; 1118*; 1119; 1121; and 1121* each of which is individually and specifically incorporated by reference herein in its entirety fully as disclosed in the foregoing U.S. Application Publication.

TALL-1 specific antibodies and other TALL specific binding proteins such as those described in U.S. Application Publication Number 2003/0195156 which is incorporated herein by reference in its entirety as to TALL-1 binding proteins, particularly the molecules of Tables 4 and 5B, each of which is individually and specifically incorporated by reference herein in its entirety fully as disclosed in the foregoing US Application Publication.

Stem Cell Factor(s) ("SCF") and related proteins such as those described in U.S. Pat. Nos. 6,204,363 and 6,207,802, each of which is incorporated herein by reference in its entirety as to stem cell factors and related proteins, particularly, for example, the stem cells factor "STEMGEN™,"

Flt3-Ligands, ("Flt3L") and related proteins such as those described in U.S. Pat. No. 6,632,424 which is incorporated herein by reference as to Flt3-ligands and related proteins in this regard.

IL-17 receptors and related proteins ("IL-17R"), such as those described in U.S. Pat. No. 6,072,033 which is incorporated herein by reference as to Flt3-ligands and related proteins in this regard.

Etanercept, also referred to as Enbrel, and related proteins.

Actimmune (Interferon-gamma-1b), Activase (Alteplase), Aldurazme (Laronidase), Amevive (Alefacept), Avonex (Interferon beta-1a), BeneFIX (Nonacog alfa), Beromun (Tasonermin), Beatseron (Interferon-beta-1b), BEXXAR (Tositumomab), Tev-Tropin (Somatropin), Bioclate or RECOMBINATE (Recombinant), CEREZME (Imiglucerase), ENBREL (Etanercept), Eprex (epoetin alpha), EPOGEN/Procit (Epoetin alfa), FABRAZYME (Agalsidase beta), Fasturtec/Elitek ELITEK (Rasburicase), FORTEO (Teriparatide), GENOTROPIN (Somatropin), GlucaGen (Glucagon), Glucagon (Glucagon, rDNA origin), GONAL-F (follitropin alfa), KOGENATE FS (Octocog alfa), HERCEPTIN (Trastuzumab), HUMATROPE (SOMATROPIN), HUMIRA (Adalimumab), Insulin in Solution, INFERGEN® (Interferon alfacon-1), KINERET® (anakinra), Kogenate FS (Antihemophilic Factor), LEUKIN (SARGRAMOSTIM Recombinant human granulocyte-macrophage colony stimulating factor (rhuGM-CSF)), CAMPATH (Alemtuzumab), RITUXAN® (Rituximab), TNKase (Tenecteplase), MYLOTARG (gemtuzumab ozogamicin), NATRECOR (nesiritide), ARANESP (darbepoetin alfa), NEULASTA (pegfilgrastim), NEUMEGA (oprelvekin), NEUPOGEN (Filgrastim), NORDITROPIN CARTRIDGES (Somatropin), NOVOSEVEN (Eptacog alfa), NUTROPIN AQ (somatropin), Oncaspar (pegaspargase), ONTAK (denileukin diftitox), ORTHOCLONE OKT (muromonab-CD3), OVIDREL (choriogonadotropin alfa), PEGASYS (peginterferon alfa-2a), PROLEUKIN (Aldesleukin), PULMOZYME (dornase alfa), Retavase (Reteplase), REBETRON Combination Therapy containing REBETOL® (Ribavirin) and INTRON® A (Interferon alfa-2b), REBIF (interferon beta-1a), REFACTO (Antihemophilic Factor), REFLUDAN (lepirudin), REMICADE (infliximab), REOPRO (abciximab), ROFERON®-A (Interferon alfa-2a), SIMULECT (baasiliximab), SOMAVERT (Pegivisomant), SYNAGIS® (palivizumab), Stemben (Ancestim, Stem cell factor), THYROGEN, INTRON® A (Interferon alfa-2b), PEG-INTRON® (Peginterferon alfa-2b), XIGRIS® (Drotrecogin alfa activated), XOLAIR® (Omalizumab), ZENAPAX® (daclizumab), ZEVALIN® (Ibritumomab Tiuxetan).

4. Sequence Variation

Particularly preferred proteins in regard to all of the foregoing and the following, include those that comprise a region that is 70% or more, especially 80% or more, more especially 90% or more, yet more especially 95% or more, particularly 97% or more, more particularly 98% or more, yet more particularly 99% or more identical in amino acid sequence to a reference amino acid sequence of a binding protein, as illustrated above, particularly a pharmaceutical binding protein, such as a GenBank or other reference sequence of a reference protein.

Identity in this regard can be determined using a variety of well-known and readily available amino acid sequence analysis software. Preferred software includes those that implement the Smith-Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include FASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by MasPar.

The BLASTN, BLASTX, and BLASTP programs are among preferred programs for such determinations, the former for polynucleotide sequence comparisons and the latter two for polypeptide sequence comparisons: BLASTX for comparison of the polypeptide sequences from all three reading frames of polynucleotide sequence and BLASTP for a single polypeptide sequence.

BLAST provides a variety of user definable parameters that are set before implementing a comparison. Some of them are more readily apparent than others on graphical user interfaces, such as those provided by NCBI BLAST and other sequence alignment programs that can be accessed on the internet. The settings and their values are set out and explained on the service web sites and are explained and set out in particular detail in a variety of readily available texts, including but not limited to *Bioinformatics: Sequence And Genome Analysis, 2nd* Ed., David W. Mount, Cold Spring Harbor Laboratory Press, Cold Spring Harbor, N.Y. (2004), especially Chapters 3, 4, 5, and 6 as to comparison of protein and nucleic acid sequences in general and as to BLAST comparisons and searches in particular; *Sequence Analysis In A Nutshell: A Guide To Common Tools And Databases*, Scott Markel and Darryl León, O'Reilly & Associates, Sebastopol, Calif. (2003), especially Chapter 7 as to BLAST in particular, each of which is herein incorporated by reference in its entirety particularly in parts pertinent to comparison of nucleotide and polypeptide sequences and to determining their degree of identity, similarity, homology and/or the like, especially as to comparison of a test sequence and a reference sequence to calculate a degree (percent) of identity between them.

In preferred embodiments of the invention in this regard, relatedness of sequences is defined as the identity score in percent returned by any one or another of the aforementioned BLAST comparison searches with e=10 and all other parameters set to their default values on the NCBI web server as set forth in *Sequence Analysis In A Nutshell: A Guide To Common Tools And Databases*, Scott Markel and Darryl León, O'Reilly & Associates, Sebastopol, Calif. (2003), pages 47-51 which are incorporated herein by reference in their entireties and in all particulars of the preferred settings for parameters of the present invention for comparing sequences using BLAST, such as those on NCBI BLAST.

The following references provide additional information on sequence comparisons in this regard, and in others. *Guide To Human Genome Computing*, Ed. Martin J. Bishop, Academic Press, Harcourt Brace & Company Publishers, New York (1994), which is incorporated herein by reference in its entirety with regard to the foregoing, particularly in parts pertinent to determining identity and or homology of amino acid or polynucleotide sequences, especially Chapter 7. The BLAST programs are described in Altschul et al., "Basic Local Alignment Research Tool," *J Mol Biol* 215: 403-410 (1990), which is incorporated by reference herein in its entirety. Additional information concerning sequence analysis and homology and identity determinations are provided in, among many other references well-known and readily available to those skilled in the art: *Nucleic Acid And Protein Sequence Analysis: A Practical Approach*, Eds. M. J. Bishop and C. J. Rawings, IRL Press, Oxford, UK (1987); *Protein Structure: A Practical Approach*, Ed. T. E. Creighton, IRL Press, Oxford, UK (1989); Doolittle, R. F., "Searching through sequence databases," *Met Enz.* 183: 99-110 (1990); Meyers and Miller, "Optimal alignments in linear space" *Comput. Applica. in Biosci* 4: 11-17 (1988); Needleman and Wunsch, "A general method applicable to the search for similarities in amino acid sequence of two proteins," *J Mol Biol* 48: 443-453 (1970) and Smith and Waterman, "Identification of common molecular subsequences," *J Mol Biol* 147: 1950 et seq. (1981), each of which is incorporated herein by reference in its entirety with reference to the foregoing, particularly in parts pertinent to sequence comparison and identity and homology determinations.

Particularly preferred embodiments in this regard have 50% to 150% of the activity of the aforementioned reference protein, particularly highly preferred embodiments in this regard have 60% to 125% of the activity of the reference protein, yet more highly preferred embodiments have 75% to 110% of the activity of the reference protein, still more highly preferred embodiments have 85% to 125% of the activity of the reference, still more highly preferred embodiments have 90% to 110% of the activity of the reference.

H. Buffers and Diluents

Buffers in accordance with this aspect of the invention are compatible with the protein appropriate to the desired end use, provide adequate buffering capacity at concentrations consistent with acceptable osmolarity, are inert, stable, and have their maximum buffering capacity at or near the desired pH.

A variety of buffers can be used in the lyophilization solution in accordance with various aspects and preferred embodiments of the invention in this regard. (Some of the same buffers can be used to reconstitute lyophilates, as discussed below.) Preferred buffers in this aspect of the invention include histidine, glutamate, Tris, and succinate, to mention just a few. Particularly preferred for some proteins are histidine buffering systems, e.g., Fc-IL-1ra. For other proteins, Tris is highly preferred, e.g., etanercept. Buffer concentration preferably is in the range of 5 to 100 mM. Particularly preferably it is in the range of 10 to 50 mM. In certain preferred embodiments, the preferred buffer concentration is 10 to 20 mM.

Buffers in accordance with this aspect of the invention are effective to maintain appropriate pH. The exact optimal pH will vary from protein to protein. Accordingly, different buffer systems will be more or less better than one another for different proteins. Generally, however, the preferred buffers are effective for pH in the range of 5 to 8, especially in the range of 5.5 to 7.5.

I. Bulking Agents

A variety of bulking agents can be used in accordance with various aspects and preferred embodiments of the invention herein disclosed. In particular, bulking agents can be used in this regard to facilitate the formation of uniform lyophilate cakes with desired structure and porosity.

Among bulking agents useful in this regard are mannitol, anhydrous lactose, sucrose, D(+)-trehalose, dextran 40, povidone (PVP K24), glycine, and hydroxyethyl starch. Among particularly preferred bulking agents in this regard are mannitol, trehalose, and glycine. Especially particularly preferred in this regard are mannitol, glycine, and hydroxyethyl starch.

J. Lyoprotectants

Lyoprotectants are substances that, generally, protect proteins against denaturation as a result of lyophilization. In certain aspects and preferred embodiments of the invention thereof, lyoprotectants are used in the lyophilization process, and the resulting lyophilates and compositions produced thereby comprise the same. Among lyoprotectants in accordance with certain preferred embodiments of the invention are sucrose, trehalose, and mannitol.

K. Anti-Foaming Agents/Surfactants

Anti-foaming agents and/or surfactants also can be used in accordance with various aspects and preferred embodiments of the invention. Among preferred anti-foaming agents are the non-ionic surfactants, low concentrations of organic solvents (less than 10% w/v), anti-gas agents, such as simethicone, and salting agents, such as $CaCl_2$ and $MgCl_2$.

Preferred non-ionic surfactants include polysorbate and Pluronic surfactants. Especially particularly preferred polysorbates and Pluronic surfactants are polysorbate 20, polysorbate 80, and Pluronic F68. Among commercially available polysorbates, Tween 20 and Tween 80 are often preferred.

In certain of the preferred embodiments in this regard, polysorbate 80 is particularly preferred, alone or with other anti-foaming agents and/or surfactants, particularly at a concentration of 0.0005% to 2% w/v. Very particularly preferred is a concentration from 0.001% to 0.5% w/v. Further in this regard, polysorbate 80 concentration from 0.002% to 0.1% w/v is highly particularly preferred, and a concentration of polysorbate 80 from 0.002% to 0.05% w/v is very highly particularly preferred. Polysorbate 80 at a concentration of approximately 0.004% w/v is very highly especially preferred. Among commercially available polysorbate 80 surfactants, Tween 80 is often preferred.

In certain additional preferred embodiments in this regard, Pluronic F68 is particularly preferred, alone or with other anti-foaming agents and/or surfactants, particularly at a concentration of 0.2% to 2% w/v. Very particularly preferred concentrations of Pluronic F68 are from 0.5% to 1.5%. Further in this regard, a concentration from 0.8% to 1.2% is highly particularly preferred, and a concentration of 1.0% is very highly particularly preferred.

In certain of the preferred embodiments in this regard, polysorbate 20 is preferred, alone or with other anti-foaming agents and/or surfactants, particularly at a concentration of 0.0005% to 2% w/v. Very particularly preferred is a concentration from 0.001% to 0.5% w/v. Further in this regard, polysorbate 20 concentration from 0.002% to 0.1% w/v is highly particularly preferred, and a concentration of polysorbate 20 from 0.002% to 0.05% w/v is very highly particularly preferred. Polysorbate 20 at a concentration of approximately 0.004% w/v is very highly especially preferred. Among commercially available polysorbate 20 surfactants, Tween 20 is often preferred.

II. Lyophilization Methods

Methods provided by embodiments of the present invention provide compositions as described above. Various embodiments of aspects of the invention in this regard provide lyophilization methods in which: (a) a vacuum pressure is maintained during freezing that ensures the formation of a lyophilate with the desired surface area and/or porosity; and/or (b) the concentrations of protein and the bulking agent(s) (if any) during freezing are selected to ensure the formation of a lyophilate with the desired surface area and/or porosity; and/or (c) the temperatures selected for annealing and secondary drying ensure desired formation of polymorphs during lyophilization and/or the desired distribution of polymorphs in the lyophilized composition.

In particular embodiments, the composition to be lyophilized comprises mannitol and the conditions of lyophilization, including any one or more of (a), (b), and (c) in the foregoing paragraph, ensure that the mannitol in the lyophilate is made up of equal to or greater than approximately 70% delta mannitol, equal to or less than approximately 20% mannitol hydrate, and equal to or less than approximately 10% amorphous mannitol. In particular embodiments in this regard the composition and the lyophilization conditions ensure that the mannitol in the lyophilate is made up of equal to or greater than approximately 70% delta mannitol, equal to or less than approximately 20% mannitol hydrate, and equal to or less than approximately 10% amorphous mannitol.

In various embodiments, the composition to be lyophilized and the conditions of lyophilization, including any one or more of (a), (b), or (c) in the foregoing paragraph, ensure that the surface area of the lyophilate is greater than or equal to approximately 1.0 $m^2$/gm and equal to or less than approximately 1.7 $mm^2$/gm. In particular embodiments in this regard, the composition and the conditions ensure that the surface area of the lyophilate is greater than or equal to 1.0 $m^2$/gm and equal to or less than 1.7 $mm^2$/gm.

In certain embodiments of the invention, in addition to any of the foregoing, solutions are degassed prior to lyophilization and/or diluent is degassed prior to addition to the lyophilate composition. In various embodiments of the invention the diluent used for reconstituting the lyophilized composition comprises a surfactant. In particular embodiments in this regard the surfactant is one or both of polysorbate 20 and Pluronic F68.

In embodiments of the invention, in addition to any of the foregoing, the solution for lyophilization and the lyophilization conditions ensure the formation of lyophilate compositions wherein in three minutes or less after adding a diluent to said lyophilate: (a) the lyophilate is at least 90%+/−10% dissolved; (b) the height of foam above the resulting solution is less than 35% of the height of the foam above the solution plus the height of the solution; (c) there is no visible effervescence in the solution, and (d) the concentration of said protein in said diluent after reconstitution is at least 40 mg/ml.

In certain embodiments, in addition to any of the foregoing, the formulation of the composition for lyophilization and the conditions for lyophilization provide lyophilate compositions wherein within three minutes of adding the diluent: (a) the lyophilate is at least 90%+/−10% dissolved, (b) the height of the foam above the resulting solution is less than 25% of the height of the foam plus the height of the solution, and (c) there is no visible effervescence in the solution and/or there are no visible bubbles in the solution.

In various embodiments, in addition to any of the foregoing, the composition for lyophilization and the lyophilization conditions ensure the formation of a lyophilate, wherein within three minutes of adding the diluent: (a) the lyophilate is at least 90%+/−10% dissolved, (b) the height of the foam above the resulting solution is less than 15% of the height of the foam plus the height of the solution, and (c) there is no visible effervescence in the solution.

In some embodiments, in addition to any of the foregoing, the composition for lyophilization and the lyophilization conditions ensure the formation of a lyophilate, wherein within three minutes of adding the diluent: (a) the lyophilate is at least 90%+/−10% dissolved, (b) the height of the foam above the resulting solution is less than 5% of the height of the foam plus the height of the solution, and (c) there is no visible effervescence in the solution.

In a variety of embodiments, instead of or in addition to any of the foregoing, the composition for lyophilization and the lyophilization conditions ensure the formation of a lyophilate, wherein within any of 10, 5, 3, 2 or 1 minutes of adding diluent: (a) the lyophilate is any of at least: 75, 85, 90, 93, 95, 97, 98, or 99% dissolved, (b) the height of the foam above the resulting solution is less than 5% of the height of the foam plus the height of the solution, and (c) there is no visible effervescence in the solution.

In various embodiments, in addition to any of the foregoing, the composition for lyophilization and the lyophilization conditions ensure the formation of a lyophilate having a surface area that is equal to or greater than any of approximately 1.0, 1.1, 1.2, 1.3, or 1.4 $m^2$/gm. In particular embodiments in this regard the lyophilate has a surface area that is equal to or greater than any of 1.0, 1.1, 1.2, 1.3, or 1.4 $m^2$/gm; in certain particular embodiments greater than 1.0 $m^2$/gm, and in certain particular embodiments greater than 1.2 $m^2$/gm. In various embodiments the lyophilate has a surface area that is equal to or greater than any of approximately 1.0, 1.1, 1.2, 1.3, or 1.4 $m^2$/gm and equal to or less than any of approximately 1.5, 1.7, 2.0, 2.5, 3.0, 4.0, or 5.0 $m^2$/gm, in particular embodiments having any combination of the foregoing lower and upper limits. In certain embodiments in this regard the lyophilate has a surface area that is equal to or greater than any 1.0, 1.1, 1.2, 1.3, or 1.4 $m^2$/gm and equal to or less than any of 1.5, 1.7, 2.0, 2.5, 3.0, 4.0, or 5.0 $m^2$/gm, in particular embodiments having any combination of the foregoing lower and upper limits. In certain embodiments the lyophilate has a surface area that is equal to or greater than approximately 1.0 $m^2$/gm. In various embodiments the lyophilate has a surface area that is equal to or greater than approximately 1.2 $m^2$/gm. In particular embodiments the lyophilate has a surface area that is equal to or greater than 1.0 $m^2$/gm. In a variety of embodiments the lyophilate has a surface area that is equal to or greater than 1.2 $m^2$/gm.

In many embodiments, in addition to any of the foregoing, the composition for lyophilization and the lyophilization conditions ensure the formation of a lyophilate, wherein addition of diluent results in a solution with a protein concentration of approximately 40 to 250 mg/ml. In various embodiments it is approximately 40 to 200 mg/ml. In certain embodiments it is approximately 75 to 150 mg/ml. In particular embodiments it is approximately 50 to 100 mg/ml. In numerous embodiments it is at least approximately 35 mg/ml. In various embodiments it is at least approximately 40 mg/ml.

In many embodiments, in addition to any of the foregoing, the composition for lyophilization and the lyophilization conditions ensure the formation of a lyophilate, wherein addition of diluent results in a solution with a protein concentration of any of 40 to 250, 35 to 225, 40 to 200, 75 to 150, or 50 to 100 mg/ml. In numerous embodiments the concentration is any of at least 35, 40, 45, 50, 60, 75, 90, 100, 125, or 150 mg/ml. In numerous embodiments, in addition to any of the foregoing, the composition for lyophilization and the lyophilization conditions ensure the formation of a lyophilate, wherein within any of 10, 5, 3, 2 or 1 minutes of adding diluent to the lyophilate there is no visible turbidity in the solution and/or there are no visible bubbles in the solution and/or there are no visible particles in the solution and/or the solution flows easily.

In numerous embodiments, in addition to any of the foregoing, the composition for lyophilization and the lyophilization conditions ensure the formation of a lyophilate, wherein the resulting solution is of sufficiently low viscosity to flow efficiently through a hypodermic needle of a gauge effective for subcutaneous injection into human subjects. In various embodiments, in addition to any of the foregoing, the composition for lyophilization and the lyophilization conditions ensure the formation of a lyophilate, wherein the composition comprises any one or more of at least one bulking agent, and/or at least one stabilizing agent and/or at least one surfactant In certain embodiments, in addition to any one of the foregoing, the stabilizing agent is sucrose.

In various embodiments in addition to any of the foregoing, the surfactant is a polysorbate. In particular embodiments in this regard the concentration of the polysorbate is from 0.004% to 0.15%. In numerous embodiments in this regard, the surfactant is a polysorbate 80 or a polysorbate 20 in a concentration from 0.004% to 0.15%, In certain embodiments in addition to any of the foregoing, the surfactant is Pluronic F68. In particular embodiments in this regard the surfactant is Pluronic F68 in a concentration of 0.05% to 1.5%.

In many embodiments, in addition to any of the foregoing, the protein is an agent for human therapeutic use or for veterinary use. In particular embodiments furthermore the protein is a pharmaceutical agent for human therapeutic use.

FIG. 1 provides a schematic depiction of the steps of a preferred lyophilization method in accordance with the invention. It is to be appreciated that FIG. 1 is provided by way of illustration only and does not represent any particular limitations of the invention. In particular, the temperatures, times, slopes, and the number of steps and their natures will vary from those in FIG. 1 in accordance with other aspects and embodiments of the invention, as discussed below.

A. Sample Preparation

Proteins may be prepared for lyophilization in accordance with the invention using standard techniques. Thus, for instance, proteins may be formulated in a solution with the desired buffering agents, bulking agents, lyoprotectants, surfactants, and other desired components by dialysis, diafiltration, precipitation and resuspension, and/or dilution, among other methods that are well-known and conventionally employed in this regard. Generally, the methods of preparation employed and the components of the sample formulation for the lyophilization process will not deleteriously affect the protein, will be stable, will provide a formulation upon reconstitution suitable for the intended use of the lyophilate, and will be both compatible and acceptable therefore.

In preferred embodiments of the invention in this regard, the sample formulation is degassed prior to lyophilization. Degassing of the formulation may be accomplished by well-known conventional means. A preferred method for degassing is vacuum degassing. Whatever method is used, it should be compatible with the sample and the end use for veterinary and human therapeutic uses. Degassing should be carried out under appropriate sterile conditions.

Optionally, in certain preferred embodiments of the invention, prior to freezing, sample formulations are cooled to an initial holding temperature and maintained at the temperature for a holding period before being further reduced in temperature and frozen as described in the following step. Preferred temperatures in this regard are 3° C. to 7° C. Particularly preferred are temperatures of 4° C. to 6° C., and highly particularly preferred is approximately 5° C.

B. Freezing

In accordance with certain aspects and preferred embodiments of the invention, a composition comprising a protein of interest formulated in accordance with the above step is frozen under carefully controlled conditions. Without being limited to any particular mechanism, it is currently believed that optimum freezing conditions program ice nucleation and pore formation in the frozen material that allow the efficient sublimation of the frozen water in the frozen sample (typically during subsequent drying steps, as described below). In certain of the preferred embodiments in this regard, freezing is carried out under partial vacuum. In certain further preferred embodiments in this regard, the protein-comprising composition is cooled slowly. In yet still further preferred embodiments in this regard, the composition is cooled until it is very completely frozen and, in certain particularly preferred embodiments in this regard, it is supercooled.

Optimum cooling rates for freezing in accordance with this aspect of the invention will vary with the exact nature of the protein comprising composition. Generally, conditions for cooling and freezing in this regard are chosen so that the ice formed in the frozen material and the structure of the material itself facilitates efficient and complete sublimation of water without deleterious effects on the frozen protein or its reconstitution. Some experimentation may be required to determine exactly the optimum conditions for freezing a given protein-containing composition so that it may be reliably and rapidly reconstituted at high concentration in a desired diluent. However, for the vast majority of protein comprising compositions, the conditions will fall within the preferred conditions set forth below.

Preferred freezing rates of the invention in this regard are between 0.001° C. and 5.0° C. per minute. Particularly preferred rates in this regard are between 0.005° C. and 2.0° C. per minute. Very particularly preferred rates in this regard are between 0.01° C. and 1.0° C. per minute. Very highly particularly preferred rates in this regard are between 0.01° C. and 0.8° C. per minute. Especially preferred rates in this regard are between 0.2° C. and 0.5° C. per minute.

Among preferred freezing temperatures reached at the end of the cooling cycle in accordance with the invention are temperatures in the range −5° C. to −200° C. Particularly preferred are temperatures in the range −15° C. to −150 C. Highly particularly preferred are temperatures in the range −25° C. to −100° C. Especially preferred are temperatures in the range −35° C. to −6° C. Very especially preferred are temperatures in the range −35° C. to −60° C.

For certain illustrative examples provided herein below, for instance, compositions containing proteins of interest are cooled from 20° C. to −50° C. at 0.3° C. per minute, and then held at −50° C. for a time.

C. Low Temperature Hold

After the sample is cooled to the desired freezing temperature, it is held at that temperature. Preferred freezing temperatures are mentioned in the foregoing section. While the hold time will differ for different samples, and optimum hold times likely will often differ for the same samples, lyophilized in different geometries or using different machines, preferred hold times will generally be in accordance with the following. For holding samples at −50° C., preferred hold times will often be in the range of 30 minutes to several hours. Particularly preferred, for samples and processes similar to those of the examples provided below, are hold times from 30 minutes to 2 hours. Especially preferred in this regard, are hold times in the range of 45 minutes to 90 minutes, especially hold times of approximately 1 hour.

D. Heating to the Annealing Temperature

In accordance with various additional aspects and embodiments of the invention herein described, after freezing as described above, compositions comprising proteins in accordance with the invention are heated and annealed. Without being limited to any particular mechanism or explanation of underlying processes, it is believed that proper annealing conditions can program crystallization of substantially all excipients in the composition, such as bulking agents. For instance, annealing parameters can ensure that substantially all the small excipient crystals fuse with one another (join together). Alternatively, annealing parameters can be adjusted to ensure that excipients stay in the amorphous phase, such as may be desirable for sucrose and trehalose, for example. Annealing prevents crystallization at other times when it may deleteriously affect structure of the composition, such as its porosity, and adversely impact lyophilization and properties of the lyophilate ultimately obtained. It also prevents crystal movement that might have similar deleterious effects, particularly at the higher temperatures used in the drying steps (discussed below).

A certain amount of experimentation may be required to determine optimal conditions for heating and annealing for different compositions, such as those comprising different bulking agents and/or other excipients. However, optimum conditions for heating and annealing the vast majority of protein-comprising compositions will fall within the parameters provided herein below.

Preferred critical warming rates of the invention in this regard are between 0.001° C. and 5.0° C. per minute. Particularly preferred rates in this regard are between 0.01° C. and 2.0° C. per minute. Very particularly preferred rates in this regard are between 0.1° C. and 1.0° C. per minute. Very highly particularly preferred rates in this regard are between 0.2° C. and 0.8° C. per minute.

Among preferred annealing temperatures reached at the end of the heating ramp in accordance with the invention in this regard are temperatures in the range −35° C. to 0.0° C. Particularly preferred are temperatures in the range −30° C. to −5.0° C. Highly particularly preferred are temperatures in the range −25° C. to −5.0° C. Especially preferred are temperatures in the range −25° C. to −10° C. Very especially preferred are temperatures in the range −20° C. to −10° C.

E. Holding at the Annealing Temperature

After the sample reaches the annealing temperature it is maintained at that temperature for a period of time. Typically a sample is maintained at the annealing temperature for a period of time sufficient for substantially all of the excipient(s) in the composition to anneal, generally for several hours. Preferred in this regard are annealing periods of 2 to 20 hours. Particularly preferred are annealing periods of 5 to 15 hours. Very particularly preferred are annealing periods of 1 to 6 hours, especially 2 to 5 hours, very especially 3 to 4 hours.

It is crucial to keep the sample below the Tg throughout the period of the hold at the annealing temperature.

F. Temperature Reduction

When the prior period is complete, compositions in accordance with certain aspects and preferred embodiments of the invention herein described are cooled and their temperature is reduced. Without being limited to any particular explanation or underlying mechanism in this regard, it is believed that lowering the temperature at this point reduces thermal motion in the composition to near minimum and, in essence, locks down structures in the composition, in particular, those formed during the previous step.

It is particularly important in accordance with certain aspects and preferred embodiments of the invention in this regard to maintain the temperature of the composition below the Tg during the temperature reduction and in subsequent process steps.

Preferred temperature reduction rates of the invention in this regard are between 0.001° C. and 5.0° C. per minute. Particularly preferred rates in this regard are between 0.005° C. and 2.0° C. per minute. Very particularly preferred rates in this regard are between 0.01° C. and 1.0° C. per minute. Very highly particularly preferred rates in this regard are between 0.01° C. and 0.8° C. per minute. Especially preferred rates in this regard are between 0.2° C. and 0.5° C. per minute.

Among preferred temperatures reached at the end of this step in accordance with the invention are temperatures in the range −5° C. to −200° C. Particularly preferred are temperatures in the range −15° C. to −150° C. Highly particularly preferred are temperatures in the range −25° C. to −100° C. Especially preferred are temperatures in the range −35° C. to −65° C. Very especially preferred are temperatures in the range −35° C. to −60° C.

G. Low Temperature Hold

After the sample is cooled to the desired temperature, it is held at that temperature. Preferred temperatures are mentioned in the foregoing section. While the hold time will differ for different samples and optimum hold times likely will often differ for the same samples lyophilized in different geometries or using different machines, preferred hold times will generally be in accordance with the following. Preferred hold times are in the range of 25 minutes to 50 minutes. Particularly preferred are hold times from 25 minutes to 35 minutes, especially hold times of approximately 30 minutes.

Prior to initiating the next step which involves heating the sample and raising its temperature, atmospheric pressure on the sample should be reduced. For samples similar to those described herein and illustrated in the examples below, preferred pressures are in the range of 25 to 250 mTorr. Particularly preferred are pressures in the range of 50 to 200 mTorr. Very particularly preferred are pressures between 75 and 175 mTorr.

H. Heating to a First Drying Temperature

In accordance with certain aspects and preferred embodiments of the invention herein described, after the previous step, the compositions are heated to a first drying temperature. Preferred heating rates are in the range of 0.05° C. to 2.5° C. per minute. Particularly preferred are rates in the range of 0.1° C. to 2.0° C. Especially particularly preferred are rates in the range of 0.25° C. to 1.25° C., and very especially particularly preferred are rates in the range of 0.5° C. to 1.0° C.

Importantly, the temperature is maintained below the glass transition temperature of the composition throughout the process. It will be appreciated by those skilled in the pertinent arts that the Tg of the composition depends on water content. For instance (purely for illustrative purposes and without limitation) in examples provided below, the composition at the beginning of heating to the first drying temperature is frozen at −50° C., contains approximately 80% water, and has a Tg of −32° C. At the end of the heating ramp and holding at the first heating temperature, as described in subsection (I) immediately below, the composition is frozen at 0° C., contains about 50% water, and has a Tg of about 5° C.

The exact conditions optimally employed for a given composition may vary from the exact conditions provided herein, and a certain amount of experimentation may be required in a given case to determine the optimum conditions. However, for the vast majority of protein-comprising compositions, optimal conditions will lie within or near the conditions and ranges herein provided.

The vacuum throughout this step should be maintained at the pressures noted in the previous step. Optionally, however, the pressure may be further reduced during this step so that when the first drying temperature is reached the vacuum is below 200 mTorr, preferably below 150 mTorr, particularly preferably about 50 mTorr.

I. First Drying Period

In accordance with certain aspects and preferred embodiments of the invention, following the heating ramp, the composition is dried under vacuum. In particular, the composition is dried under vacuum at a temperature below the Tg for a time sufficient to reduce the water content to a desired value.

It is particularly important to maintain the temperature below the Tg throughout the drying process.

Without being limited to any particular mechanism or explanation of underlying processes, maintaining the composition under vacuum at the first heating temperature (and always below the Tg) facilitates sublimation of frozen water from the composition without deleteriously affecting the structure or desirable properties of non-volatile components of the composition that are not removed by the process.

The exact conditions for primary heating of a given composition may differ from the precise conditions disclosed in the examples below. A certain amount of experimentation may be required to determine optimal conditions for the primary heating step for different compositions, such as those comprising different bulking agents and/or other excipients. However, for the majority of protein-comprising compositions these optimum conditions will fall within the parameters provided herein below and for the most part will be similar to the specific conditions reported in the illustrative examples below.

In preferred embodiments of the invention in this regard, the first drying temperature is at least 1° C., particularly preferably at least 2° C., highly preferably at least 4° C., especially at least 5° C. or more, below the initial Tg of the composition. In particular, preferred ranges for the first drying temperature are 2° C. to 20° C., particularly preferable, 3° C. to 10° C., especially 4° C. to 8° C., below the initial Tg of the composition at the first drying temperature.

In certain of further preferred embodiments in this regard, the composition is held at the first drying temperature for an extended period of time. In particularly preferred embodiments in this regard, the composition is held at the first drying temperature for 5 to 50 hours, and in highly preferred embodiments it is held at the first drying temperature for 10 to 30 hours. In especially preferred embodiments in this regard, the composition is held at the first drying temperature for 10 to 20 hours.

As noted above, the temperature should always be kept at least a few degrees below the Tg, which places a practical maximum on the initial temperature for the first drying step for any given compound. In preferred embodiments of the invention in this regard, the drying temperature is 2° C. to 15° C. below the Tg, 3° C. to 12° C. below in particularly preferred embodiments, and 4° C. to 8° C. below in certain especially preferred embodiments. In certain especially highly preferred embodiments, it is 5° C. to 6° C. below the Tg.

In addition, in certain aspects and preferred embodiments of the invention in this regard, the composition is maintained under vacuum at or below 200 mTorr at the drying temperature until the amount of water has been reduced to between 5% and 25% by weight of the composition, preferably to between 5% and 20%, particularly preferably to between 7% and 15%.

In the illustrative examples provided below, the first drying step was carried out at 0° C. for about 15 hours until the water content of the composition was reduced to approximately 10%.

J. Heating to a Second Drying Temperature

At the end of the first drying period at the first drying temperature, in accordance with certain aspects and preferred embodiments of the invention herein disclosed, the composition is heated to a second drying temperature. The temperature of the composition is maintained below the Tg throughout the ramp in temperature to the second drying temperature.

Preferred heating rates are in the range of 0.05° C. to 2.5° C. per minute. Particularly preferred are rates in the range of 0.1° C. to 2.0° C. Especially particularly preferred are rates in the range of 0.25° C. to 1.25° C., and very especially particularly preferred are rates in the range of 0.5° C. to 1.0° C.

Preferred temperatures for the second drying step are 15° C. to 35° C. Particularly preferred temperatures are in the range of 20° C. to 30° C. Especially particularly preferred is a temperature of approximately 25° C. (±2° C.).

Vacuum is maintained throughout this step. It may be kept at the same pressure as the previous step or it may be further reduced. Where the pressures of the first and second drying steps differ, preferred vacuum pressures for the second drying step are provided below.

K. Second Drying Period

In accordance with certain aspects and preferred embodiments of the invention herein disclosed, the composition is maintained under vacuum at a second drying temperature for a time sufficient at least to reduce residual water to less than 1% by weight of the composition and, in particularly preferred embodiments of the invention in this respect, to reduce residual water to 0.5% or less.

The second drying period will, of course, depend on the temperature. It is to be expected that it will be shorter in general for higher temperatures, all other things being relatively equal. The following preferred drying times relate to drying at around 25° C. Preferred times in this regard are 4 to 14 hours, particularly preferred 6 to 12 hours, especially particularly preferred 8 to 10 hours, and very especially particularly preferred approximately 9 hours.

The vacuum pressure in the second drying period can be the same or different than that of the first drying period. Preferably the pressure is below 150 mTorr, particularly preferably below 100 mTorr, especially particularly preferably 50 mTorr or less.

L. The Lyophilate

At the end of the drying period, a lyophilate is obtained under vacuum with desirably low moisture content, a cake structure, and other properties that provide for stability and ease of reconstitution as described elsewhere herein. Preferred lyophilates of the invention can be reformulated by addition of appropriate diluent to form concentrated protein solutions wherein the protein concentration is as described in greater detail elsewhere herein. Furthermore, the lyophilates dissolve rapidly preferably in 10 minutes or less, particularly preferably in 5 minutes or less, especially preferably in 3 minutes or less. Solvation in the diluent also occurs without formation of excess foam, effervescence, or particulate formation. Few if any bubbles are formed, and they do not interfere with proper dosing. The resulting solutions exhibit minimal turbidity or are completely clear, also as described elsewhere herein in greater detail. Finally, when reconstituted, lyophilates of the invention provide formulations suitable for their intended use.

M. Reconstitution

As described above, the invention provides composition with improved properties of reconstitution. Generally known and used methods for reconstituting conventional lyophilates can be used to reconstitute lyophilates in accordance with the present invention. Self-evidently, parameters of lyophilization must be designed to result in a lyophilate that can readily and conveniently be reconstituted to provide the formulation appropriate to the given application.

In the present invention, in preferred embodiments, reconstitution of the lyophilate provides a highly concentrated protein solution as described elsewhere herein. In particularly preferred embodiments the resulting formulation is suitable for subcutaneous injection. In preferred embodiments in the invention in this regard, the diluent used to reconstitute the lyophilate is degassed before use. Degassing may be accomplished by standard methods, typically by vacuum. Typically a lyophilate is reconstituted in water of a grade and sterility appropriate to the intended use for many applications. The water, preferably, is free of bubbles.

Otherwise, lyophilates in accordance with the present invention are reconstituted using well-known conventional methods.

N. Resulting Formulations

Preferred lyophilates, in accordance with certain preferred embodiments of the invention, provide highly concentrated protein formulations suitable for, in particular, human therapeutic use, and use in other organisms. In particularly preferred embodiments in this regard, lyophilates in accordance with the invention can be reliably and conveniently reconstituted to provide formulations suitable for subcutaneous administration, not only by health care professionals, but also by patients, and not only in health care facilities, but also at home or other places.

Accordingly, lyophilates in accordance with preferred embodiments of the invention in this regard, as noted above, dissolve quickly upon addition of diluent with a minimum of foaming effervescence, bubbling, turbidity, and particulate formation. Preferred lyophilates are sufficiently stable and soluble for reliable dosing in home self-administration after prolonged storage.

In accordance with the foregoing, particularly preferred embodiments are reconstituted using water that meets the standards required for medical use. Upon addition of the diluent, particularly preferred lyophilates in this regard form aqueous solutions containing the lyophilized protein at a concentration of at least 35 mg/ml. In addition to other preferred embodiments described elsewhere herein, in certain preferred embodiments of the invention in this regard, reconstitution provides a formulation with a high protein concentration. In certain particularly preferred embodiments the concentration is very high. In yet further preferred embodiments, it is extremely high. Numerically in this regard, preferred concentrations are at least 35 mg/ml. Particularly preferred concentrations are in the range of 35 mg/ml to 400 mg/ml. Very particularly preferred concentrations in this regard range from 40 mg/ml to 350 mg/ml. In very highly particularly preferred embodiments, it is in the range from 45 mg/ml to 300 mg/ml. In especially preferred embodiments, it is 50 mg/ml to 250 mg/ml.

In addition, the osmolarity and viscosity of the resulting formulations are suitable for the intended uses. In particular, the viscosity should not be so high as to interfere with homogeneity of the formulation and/or administration. In particular the viscosity should be low enough for rapid mixing of all components. Furthermore in preferred embodiments it is low enough for convenient loading into syringes for subcutaneous injection.

EXAMPLES

The following examples are illustrative of particular aspects and embodiments of the invention and in no way limit its scope. Many other aspects and embodiments of the invention will be immediately clear to those skilled in the art from the contents of this disclosure, and a full understanding of the invention herein disclosed can be obtained only by careful scrutiny of the present disclosure in all its details as it should be understood by the skilled person fully knowledgeable in the pertinent arts.

Example 1

Etanercept/Starting Preparation

Lyophilized etanercept (25 mg/ml) in TMS (10 mM Tris, 1% sucrose, 4% Mannitol, and pH 7.4) was used as the starting material. The protein was concentrated using 15 ml Centriprep filtering devices (M·wt cut off—10000) to 50 mg/ml in TMS. The starting material and the concentrated material were characterized structurally and compared. No lyophilization induced damage was observed. This material was used in the examples provided below.

Example 2

Etanercept/UV Spectroscopy

Protein concentration was determined by UV absorbance, using an extinction coefficient at 280 nm of 1.14 for a 1 mg/ml solution. Diluent was used as the blank. Placebo samples were scanned from 240 nm to 400 nm using a water blank to confirm the absence of protein in the diluent. The absorbance maxima and exact wavelength of the peaks were recorded as well.

Example 3

Etanercept/Lyophilization Cycles

Etanercept at 25 mg/ml or 50 mg/ml in TMS was lyophilized on a Genesis 12 EL lyophilizer (Virtis, Gardiner, N.Y.), using four different cycles, set out in Table 1.

For each of the cycles, etanercept vials were filled with 1 ml solution in a biosafety cabinet. Copper-constantan thermocouples were inserted into select vials through holes in the sides of specialized stoppers. The distance between the thermocouple and the bottom of the vial was adjusted to be approximately 1 to 3 mm. The product vials were surrounded by at least two rows of placebo TMS vials. To achieve a more uniform contact between the vials and the shelf, stainless steel trays with removed bottoms were used.

Except as noted in Table 1, for all cycles the shelves were pre-cooled to 5 C and the product was equilibrated at this temperature to reach a uniform temperature prior to ice crystallization. The shelf was then cooled to −50 C followed by annealing at different temperatures. The formulation was then cooled back to −50 C. This was followed by primary drying at 0 C under controlled pressure and secondary drying at 25 C (in most cases).

After the completion of the cycle the vials were stoppered simultaneously under a chamber pressure of 200 mTorr.

TABLE 1

Etanercept Lyophilization Cycles

| FIG. 1 Reference | Step | Cycle 1 | Cycle 2 | Cycle 3 | Cycle 4 |
|---|---|---|---|---|---|
| A | Etanercept Initial Protein Concentration | 25 mg/ml | 50 mg/ml | 50 mg/ml | 50 mg/ml |
| A | Load Temperature | 20° C. | 20° C. | 20° C. | 20° C. |
| A | Freezing Step 1 | None | Ramp to 5° C. and hold | Ramp to 5° C. and hold | Ramp to 5° C. and hold |
| B & C | Freezing Step 2 | Ramp 0.7 to −50° C. and hold for 60 min | Ramp 0.7 to −50° C. and hold for 60 min | Ramp 0.7 to −50° C. and hold for 60 min | Ramp 0.7 to −50° C. and hold for 60 min |
| D & E | Annealing Step 1 | Ramp 0.5 to −20° C. and hold for 120 min | Ramp 0.5 to −20° C. and hold for 300 min | Ramp 0.5 to −20° C. and hold for 300 min | Ramp 0.5 to −12° C. and hold for 120 min |
| F & G | Annealing Step 2 | Ramp 0.7 to −50° C. and hold for 30 min | Ramp 0.7 to −50° C. and hold for 30 min | Ramp 0.7 to −50° C. and hold for 30 min | Ramp 0.7 to −50° C. and hold for 30 min |
| G | Chamber evacuation to pressure set point | 150 mTorr | 100 mTorr | 100 mTorr | 150 mTorr |
| H | Primary Drying Step 1 | (a) Ramp 0.17 to −45° C., then (b) Ramp 0.22 to −25° C., then (c) Ramp 0.4 to 0° C. | Ramp 1 to 0° C. at 50 mTorr | Ramp 1 to 0° C. | Ramp 1 to 0° C. |

TABLE 1-continued

Etanercept Lyophilization Cycles

| FIG. 1 Reference | Step | Cycle 1 | Cycle 2 | Cycle 3 | Cycle 4 |
|---|---|---|---|---|---|
| I | Primary Drying Step 2 | Hold at 0° C. for 360 min at 38 mTorr | Hold at 0° C. for 1080 min at 50 mTorr | Hold at 0° C. for 1140 min at 50 mTorr | Hold at 0° C. for 1080 min at 150 mTorr |
| J & K | Secondary Drying Step | Ramp 0.083 to 25° C. and hold for 540 min | Ramp 0.25 to 45° C. and hold for 180 min | Ramp 0.25 to 25° C. and hold for 540 min | Ramp 0.25 to 25° C. and hold for 540 min |
|  | Total Drying Time | 30.0 hr | 35.9 hr | 42.9 hr | 37.5 hr |

Example 4

Etanercept/Second-Derivative FTIR Spectroscopy

Protein secondary structure in both control and sample lyophilates was examined using Fourier Transform Infrared Spectroscopy. In a dry nitrogen-purged glove box, dry protein samples (approximately 0.5 mg protein) were mixed with 400 mg KBr. The mixture was ground and then pressed into a pellet at 12,500 PSI. This procedure does not alter the structure of proteins in the dry solid. Spectra were acquired with a Bomem MB series spectrometer and processed. Second-derivative spectra in the conformationally sensitive amide 1 region were normalized for area and compared.

Example 5

Etanercept/Differential Scanning Calorimetry (DSC)

Thermal analysis was carried out using a Pyris DSC (Perkin Elmer Corp.) equipped with liquid nitrogen cooling. Temperature calibration was done using the melting points of n-dodecane, hexane, and indium. About 15 µl of solution was hermetically sealed in an aluminum pan. An empty aluminum pan and lid was used as a reference. Thermograms were recorded during the heating cycle at heating rates of 5 C and 10 C/min.

Example 6

Etanercept/Size Exclusion Chromatography (SEC)

Lyophilates were analyzed by size exclusion chromatography. Elution was isocratic with a mobile phase of 100 mM sodium phosphate/50 mM NaCl, pH 6.8. The SEC column used was a Tosohaas TSK 3000SWxl, and the flow rate was 0.6 ml/min. Absorbance was measured at 215 and 280 nm. Run time was 30 minutes. Prior to injection, frozen liquid samples were thawed and diluted in USP Water For Injection (WFI) to 2.0 mg/ml. Lyophilized samples were reconstituted and diluted with WFI to 2.0 mg/ml prior to injection. Sample injection amounts were 20 micrograms. Peak areas in the chromatogram were used to quantify the amounts of monomer, high molecular weight species (HMW), and low molecular weight species (LMW).

Example 7

Etanercept/X-Ray Powder Diffractometry (XRPD)

X-ray powder diffraction patterns of freeze-dried powders were determined using a Phillips X-Pert diffractometer. A current of 40 mA and a voltage of 45 kV were used. Alignment of the equipment was verified before each measurement using a silicon reflection peak at 28.443°. The powders from different formulations were gently broken up and mounted on a low background aluminum holder. Samples were scanned from 2° to 40° at a rate of 2°/min.

Example 8

Etanercept/Scanning Electron Microscope (SEM)

Lyophilized cakes were broken into powder and then sputter-coated with gold. Sample morphology was then analyzed at different magnifications using a Philips ESEM XL30 scanning electron microscope.

Example 9

Etanercept/Reconstitution Properties (a) The time for reconstitution of lyophilized samples in DP vials was determined by visual inspection.

(b) The height of the foam observed at the end of 2 minutes after reconstitution was measured using calipers.

(c) Reconstitution was videotaped using a digital camera concurrently with visual observation.

Example 10

Etanercept/Residual Moisture

Residual moisture in the lyophilized material was measured for each lot of control and sample DP vials. Vials selected from throughout the fill were assessed for moisture content by coulometric titration. A known weight of the sample was placed in a sample oven connected to a Karl Fisher reaction vessel. The sample was purged with dry nitrogen to remove any unbound moisture. It was then heated and the residual moisture measured. Each vial was subjected to the Karl Fisher reaction in a coulomat reaction vessel. The results were calculated as a percentage of moisture per vial. The final value was the average of all the vials tested. Results are presented in Table 3 below.

Example 11

Etanercept/Fundamental Parameters

The Tg, Tcry, and eutectic temperature of the etanercept formulation at 50 mg/ml in 10 mM Tris, 1% sucrose, 4% Mannitol, pH 7.4 was determined using the sub-ambient facility of the DSC. The Tg from the first scan was −27.1

C±2.9 C. The Tg from the second scan was −24.5 C±1.8 C. The crystallization temperature was −8.5 C±1.0 C. The Teut was −4.0 C.

Example 12

Etanercept/Effects of Freezing Rates and Vacuum on Structure, Stability, and Reconstitution In order to understand the effect of freezing rate on the structure, stability, and reconstitution of etanercept at 50 mg/ml, samples were lyophilized at two different freezing rates in the lyophilizer, namely 0.3 C/min and 0.7 C/min or frozen by dipping in liquid nitrogen for 5 minutes before loading onto the lyophilizer. The samples were then allowed to undergo the other steps of lyophilization Cycle 4 in Table 1. In addition to these differences in the freezing rates, the effect of vacuum during the freezing of the samples was also analyzed by subjecting the samples in the vials to 250 mTorr pressure during the freezing step. Samples exposed to vacuum during freezing were also subjected to a modified freezing cycle, wherein samples were frozen back only to −25 C and not to −50° C., after the annealing step. The samples were then subjected to primary drying after 1 hour at −25° C. After lyophilization the samples were analyzed for their secondary structure, using FTIR spectroscopy and their reconstitution properties.

In terms of cake appearance the samples subjected to freezing using liquid nitrogen had a lesser cake volume, compared to the cake volumes of the control vials, but did not appear collapsed. The samples subjected to a modified freezing cycle including vacuum during freezing and frozen back to a higher temperature of −25° C. after the annealing step had a skin layer, and the cake volume was lesser compared to the control vial. The vials subjected to the liquid nitrogen cooling and the modified freezing cycle had a higher moisture content, obviously due to the altered pore structure left after the sublimation of ice leading to inefficient mass transfer during the primary and secondary drying steps.

The FTIR analysis of the structure of the samples in the solid state shows that the secondary structure of the samples was not significantly altered compared to the samples subjected to the modified development cycle. The intermolecular b-sheet bands appearing at around 1615 cm$^{-1}$ and 1695 cm$^{-1}$ are due to the non-optimized formulation for the higher protein concentration. FTIR analysis of the samples, after reconstitution, show that the bands disappear in the solution and all the samples look alike in terms of their secondary structure.

The reconstitution properties of the samples subjected to these different cycles are shown in Table 2 below. The reconstitution time increased at higher freezing rates, and the corresponding vial appeared visually opalescent.

TABLE 2

| Samples | Reconstitution time (sec) | Height of form (mm) | Comments |
|---|---|---|---|
| −12° C. Annealing, 0.7° C./min Cooling | 62.6 ± 5.0 | 2.7 ± 0.3 | Effervescence observed on reconstitution. Some chunks observed initially but then dissolved. |
| −12° C. Annealing, 0.3° C./min Cooling | 70.0 ± 4.8 h | 2/4 ± 0.8 | Relatively more effervescence entrapped in solution observed on reconstitution. |
| −12° C. Annealing, Liquid Nitrogen Cooling | 125.2 ± 7.2 | 2.5 ± 0.2 | Layer of undissolved material observed initially on the top of solution. Turned turbid on reconstitution. |

Example 13

Etanercept/Effects of Annealing Regime on Structure, Stability and Reconstitution 50 mg/ml etanercept samples were subjected to lyophilization with annealing at −20° C., −15° C., −10° C. and −5° C. for 5 hours using Cycle 3 in Table 1. Samples were studied immediately after lyophilization and after 1 and 3 months of storage.

All the samples annealed at −15° C. and −10° C. had good cake structure. Mild cake shrinkage was observed in vials annealed at −20° C. and −5° C.

The moisture content of the vials was analyzed using Karl Fisher analysis as described above and NIR spectroscopy. The results are presented in Table 3 below.

TABLE 3

| Lyophilization Cycle | Moisture (post lyophilization) | Moisture (3 month storage at 37° C.) | Moisture (3 month storage at 29° C.) |
|---|---|---|---|
| 25 mg/ml Control | 0.39% w/w | — | — |
| 50 mg/ml −45° C. Secondary Drying | 0.81% w/w | — | — |
| 50 mg/ml −25° C. Secondary Drying, −20° C. Annealing | 0.85% w/w | 2.24% w/w | 2.08% w/w |
| 50 mg/ml −25° C. Secondary Drying, −15° C. Annealing | 1.03% w/w | 1.52% w/w | 1.83% w/w |
| 50 mg/ml −25° C. Secondary Drying, −10° C. Annealing | 0.78% w/w | 2.30% w/w | 1.91% w/w |
| 50 mg/ml −25° C. Secondary Drying, −5° C. Annealing | 0.9% w/w | 1.33% w/w | 1.26% w/w |

FTIR analysis of the sold state samples immediately after lyophilization showed that the secondary structures were the same for samples subjected to the different annealing conditions. However, they differed from the secondary structures of the liquid control and the starting material (25 mg/ml lyo sample), exhibiting loss in the native b-sheet band and the appearance of intermolecular b-sheet bands at 1615 cm$^{-1}$ and 1695 cm$^{-1}$. Immediately after reconstitution, the decreases in the native band and both of the intermolecular b-sheet bands in the annealed samples disappeared, and the FTIR spectra of all the annealed samples was the same as the liquid control and the starting material.

DSC analysis of the solid state samples shows that the crystallization temperature of the samples was around 55° C. to 60° C. and the Tg's were all above 120° C. Thus, the different annealing conditions do not affect the structure and stability of the formulation observed immediately after lyophilization.

SE-HPLC chromatogram showed the characteristic peaks for HMW aggregates, native monomeric protein, and LMW fragments. SE-HPLC of samples prepared at the different annealing temperatures showed more HMW aggregation than control samples, 1.5% compared to 0.5% in the control samples. The amount of LMW fragments had not increased in the lyophilized samples compared to the control sample.

Lyophilized samples were stored for 3 months at three different temperatures: 4° C., 29° C., and 37° C. There was no visual evidence of collapse in any of the samples under any of these conditions.

The moisture content of the samples post lyo and after 3 months in storage at 29° C. and 37° C. are shown below in Table 3. The moisture content of the differently lyophilized samples and the controls was determined immediately after lyophilization and after 3 months of storage at 29° C. and 37° C. As shown in Table 3, immediately after lyophilization the moisture content of the differently annealed samples ranged from 0.78% w/w to 1.03% w/w. The controls were 0.39% w/w and 0.81% w/w. After 3 months storage, the moisture content of all the samples increased somewhat at both storage temperatures.

FTIR spectra analysis of the solid-state samples showed no significant changes of the samples stored for 3 months at 4° C. and 29° C. However, FTIR analysis of the samples annealed at −20° C. and stored at 37° C. showed a shift in frequency of the b-sheet band absorption lines, indicating a change in structure of the protein prepared and stored under these conditions.

Stored samples were also analyzed by SE-HPLC. The analysis was carried out as described above. SE-HPLC analysis showed slight variations in the stability of the samples prepared at the different annealing temperatures. Generally, for a given condition of storage, all the samples were within approximately 1% or less of one another. A gradual loss of native protein and accompanying accumulation of LMW was observed with increasing time and increasing temperature.

Example 14

Etanercept/Effects of Secondary Drying Temperature on Structure, Stability, and Reconstitution The effect of lyophilizing the samples at two different secondary drying temperatures, 25° C. for 9 hours or 45° C. for 3 hours, on the structure and reconstitution of the samples was studied. FTIR spectra of the solid state samples showed that the secondary structure of the samples dried at 45° C. had a lesser intramolecular beta-sheet band at 1642 $cm^{-1}$. Samples dried at 45° C. also had a longer reconstitution time and formed a thicker foam layer than the samples dried at 25° C. The results are shown in Table 4.

TABLE 4

| Samples | Reconstitution Time | Height of Form (mm) | Comments |
| --- | --- | --- | --- |
| −20° C. Annealing, 45° C. Secondary Drying | ~90 sec | 6.4 ± 0.8 | Effervescence observed on reconstitution. Some chunks observed on the side of the vial but then dissolved. |
| −20° C. Annealing, 25° C. Secondary Drying | 41.6 ± 5.8 | 5.0 ± 1.4 | Effervescence observed on reconstitution. Some chunks observed initially but then dissolved. |
| −15° C. Annealing, 25° C. Secondary Drying | 42.5 ± 4.5 | 4.8 ± 1.4 | Effervescence observed on reconstitution. |
| −10° C. Annealing, 25° C. Secondary Drying | 68.3 ± 7.6 | 3.4 ± 2.2 | Reduced effervescence on reconstitution compared to the other two conditions. Slow dissolution of the cake. |
| −5° C. Annealing, 25° C. Secondary Drying | 94.5 ± 5.0 | 2.9 ± 0.7 | Reduced effervescence on reconstitution compared to the other two conditions. Slow dissolution of the cake. |

Example 15

Etanercept/Effects of Solution Degassing and Vacuum

Lyophilates were prepared by the procedure described in Cycle 4 in Table 1. Half of the sample formulation was degassed prior to lyophilization. The other half was treated exactly the same way, but was not degassed prior to lyophilization. Some samples were held for annealing at −12° C., as indicated in the Cycle 4 procedure. Other samples were held at −15° C. Samples were reconstituted either under vacuum or at ambient atmospheric pressure. Some samples were reconstituted in diluent before they were degassed. Other samples were reconstituted in the same diluent after degassing. The reconstitution properties of lyophilates prepared according to procedures incorporating one or more of these changes were observed. The reconstitution properties of these samples were compared with one another and with the reconstitution properties of lyophilates prepared exactly as described for Cycle 4 in Table 1. All samples were reconstituted in water to a protein concentration of 50 mg/ml.

Reconstitution times ranged from 45 seconds to 70 seconds. Foam height ranged from 1.6 mm to 6.5 mm. One sample exhibited effervescence. All the samples, except as noted below, generated foam on reconstitution. Best results were obtained for material prepared from the degassed sample formulation held at −12° C. for annealing that was reconstituted under vacuum using degassed diluent. These samples were fully dissolved in approximately 45 seconds, generated very little foam (foam height 1.6 mm or less), exhibited few bubbles or particulates, and were free of noticeable turbidity.

Second best results were observed for samples prepared the same way except that the sample formulation was not degassed before lyophilization. These samples had a reconstitution time of 65 seconds, generated a thin layer of foam (approximately 2 mm), and exhibited relatively small amounts of other undesirable characteristics.

Example 16

Etanercept/Effects of Freezing Cycle on Properties of the Lyophilized Cake

In order to understand the properties of the lyophilized cake in its relation to product stability and reconstitution, we analyzed the samples using X-ray powder diffractometry (XRPD) studies and a scanning electron microscope. The X-ray diffraction patterns were obtained from samples prepared at different annealing temperatures, different freezing rates, and different secondary drying temperatures. The samples exposed to higher annealing temperatures had higher crystalline mannitol peaks, d form being the most predominant, than those performed at −20° C. annealing. Also the mannitol hydrate peak decreases when the samples are subjected to higher annealing temperatures.

At 45° C. secondary drying temperature the amount of a crystalline form of mannitol seemed to increase, but the mannitol hydrate peak is much smaller than the sample subjected to 25° C. secondary drying temperature. The samples subjected to these secondary drying temperature were also annealed at −20° C. Lesser crystalline peaks of mannitol were observed in samples subjected to liquid nitrogen freezing.

Corresponding SEM micrographs showed that the samples that reconstituted faster had a more porous structure compared to samples that reconstituted more slowly.

Increasing the sucrose concentration to 4%, caused the formation of large planar particles. As a result these samples reconstituted more slowly than lyophilates prepared from the standard TMS formulation.

Example 17

Etanercept/Summary of the Results

The reconstitution properties of samples of etanercept (50 mg/ml) lyophilized using a 25° C. secondary drying step are better than samples lyophilized using a 45° C. secondary drying step. The reconstitution properties of samples of etanercept (50 mg/ml) lyophilized using a −12° C. annealing step are better than samples lyophilized using a −20° C. annealing temperature. Post-freezing annealing removes the effect of freezing rates on the pore structure, and thus on the reconstitution properties of the lyophilized cakes. Degassing the sample formulation and the diluent, and maintaining the sample under vacuum in the sample vial, improves the reconstitution properties of the 50 mg/ml lyo cake. Increasing sucrose concentration in the lyophilized formulation contributes to longer reconstitution times. The reconstitution properties of etanercept highly correlate with the crystallinity of the samples and the pore-structure of the lyophilized cake.

Using Tween 80 and Pluronic F68 in combination in the diluent improves the reconstitution properties.

Example 18

Fc-IL-1ra/Starting Preparation

Purified Fc-IL-1ra was obtained as a 100 mg/ml frozen liquid. It was dialyzed into the formulation buffer prior to lyophilization.

Example 19

Fc-IL-1ra/Lyophilization

Samples were lyophilized in a Virtis lyophilizer according to the general scheme depicted in FIG. 1 with the parameters set out in Table 5, except as otherwise noted. Thus, the annealing temperature was −12° C., unless otherwise stated.

TABLE 5

| FIG. 1 Reference | Step | Settings |
|---|---|---|
| A | Fc-IL-1ra Initial Protein Concentration | 100 mg/ml |
| A | Load Temperature | 4° C. |
| A | Freezing Step 1 | None |
| B & C | Freezing Step 2 | Ramp 0.5 to −50° C. and hold for 120 min |
| D & E | Annealing Step 1 | Ramp 1.3 to −12° C. and hold for 360 min |
| F & G | Annealing Step 2 | Ramp 0.6 to −50° C. and hold for 120 min |
| G | Chamber evacuation to pressure set point | 100 mTorr |
| H | Primary Drying Step 1 | Ramp 0.2 to −25° C. at 100 mTorr |
| I | Primary Drying Step 2 | Hold at −25° C. for 1600 min at 100 mTorr |
| J & K | Secondary Drying Step | Ramp 0.03 to 25° C. and hold for 800 min at 50 mTorr |
|  | Total Drying Time | 82.5 hr |

Example 20

Fc-IL-1ra/Reconstitution Properties and Stability

The integrity of the lyophilates was determined primarily by reconstitution time and by size-exclusion High Performance Liquid Chromatography under non-denaturing conditions (SE-HPLC).

Reconstitution time was determined by the same method used to measure etanercept reconstitution time, as described above. Quality assessment was based on the rapidity, completeness, and reliability of reconstitution.

SE-HPLC was carried out on a Toso Haas TSK-Gel G3000 SW×1 (30 cm×7.8 mm) column with a mobile phase of 50 mM potassium phosphate, 0.5M potassium chloride, 5% EtOH, pH 6.4, at a flow rate of 0.5 ml/min. SE-HPLC reliably and efficiently separated degradation species from intact Fc-IL-1ra based on their differences in molecular weight and charge. The areas under the peaks for intact protein and degradation product provided a quantitative measure of stability.

Other methods that can be used to resolve molecular species resulting from Fc-IL-1ra degradation in this regard include denaturing SE-HPLC, cation exchange HPLC, anion exchange HPLC, and SDS-PAGE under reducing and nonreducing conditions.

Example 21

Fc-IL-1ra/Degradation

Previous studies have shown that Fc-IL-1ra is prone to both physical and chemical degradation. The main mechanism of degradation that has prevented the molecule from being formulated as a liquid is aggregation (both covalent and noncovalent). Other minor forms of degradation include chemical degradation as detected by the loss of main peak by cation-exchange HPLC.

Fc-IL-1ra in the lyophilates obtained using Cycle 4 as described above, was intact and stable.

Example 22

Bulking Agents

The effects of bulking agents on the Fc-IL-1ra lyophilates was studied. Mannitol was found to promote shorter reconstitution times than glycine. The best results in this regard were obtained with 4% mannitol. 4% mannitol also produced the best crystallinity by annealing at three different temperatures (−11° C., −13° C., and −12° C.). Crystallinity correlated directly with ease of reconstitution. Best results in these experiments were obtained with 4% mannitol and an annealing temperature of −11° C.

However, formulations with 4% mannitol had a relatively high osmolarity (369 mOsm). In addition, in isotonic formulations (approximately 300 mOsm) the mannitol concentration also corresponded directly to the amount of main peak loss determined by SEC. In this regard, 4% mannitol showed the highest loss of the main peak of the tested mannitol concentrations.

Accordingly, the mannitol concentration for use with Fc-IL-1ra was selected to balance these two opposing effects of maintaining stability and providing adequate reconstitution properties while maintaining nearly physiological osmolarity. In accordance with preferred embodiments of the invention in this regard, the mannitol concentration is between 3.0% and 4.0%. Particularly preferred concentrations are between 3.0% and 3.8%. Especially preferred concentrations are between 3.0% and 3.6%. Especially highly preferred is the mannitol concentration of 3.3%.

Example 23

Fc-IL-1ra/Stabilizers and Lyoprotectants

Sucrose, trehalose, and arginine HCl were examined for their stabilizing effects on Fc-IL-1ra. Both sucrose and trehalose provided comparable stabilizing effects in the solid state. Other results indicated that arginine HCl might provide improved solid state stability.

Preferred stabilizers in accordance with the invention in this respect include sucrose and arginine HCl. Among particularly preferred formulations are 2% sucrose and 0.7% arginine HCl (35 mM).

Example 24

Buffers and pH

The effects of several buffer systems on the properties of the lyophilate and on reconstitution were examined, In particular histidine and glutamine were used at concentrations of 10 mM and 20 mM to buffer solutions to a series of pHs between 4.0 and 5.5. Samples prepared with the glutamate buffer exhibited reconstitution times 4 to 5 minutes longer than those of the samples prepared using histidine. Buffer at pH 4.5 and 5.0 best minimized aggregation during solid state storage. At a histidine concentration of 20 mM, solid state stability dramatically improved, accompanied by a relatively small increase in osmolarity. At 20 mM, histidine solid state stability was better at pH 5.0 than pH 4.5. (Due to the intrinsic buffering capacity of the protein, dialyzing the protein against a buffer at pH 5.0 produced formulations having a final pH of 5.3 to 5.4.)

Example 25

Fc-IL-1ra/Surfactants

The addition of polysorbate in the final dosage form decreased bubble dissipation time upon reconstitution and minimized aggregation that occurred during lyophilization and/or reconstitution. Unlike the pre-lyophilization stability properties, a minimum polysorbate concentration was required for adequate post-reconstitution liquid stability for the sucrose formulations, suggesting that some damage occurred during lyophilization and/or reconstitution for that formulation. Polysorbate 80 and polysorbate 20 behaved comparably.

Example 26

Stability of Etanercept Over Time

Etanercept at a concentration of 50 mg/ml in 12 mg/ml Tris, 40 mg/ml malmitol and 10 mg/ml sucrose at pH 7.4 was lyophilized, as described above, with annealing at −12° C. for 120 minutes and primary drying at 0° C. for 1080 minutes at 150 mTorr. Lyophilization was performed on a commercial lyophilizer (Edwards 0.6 Lyoflex). Bottles were individually thermocoupled. Shelves were pre-cooled to 5° C. and vials were equilibrated to the same temperature before ice crystallization and freezing. The shelf was supercooled to −50° C. The temperature was then raised to the annealing temperature (−12° C.) and held there for 120 minutes. The temperature then was dropped back to −50° C. and maintained at that temperature long enough for the samples to equilibrate. The temperature thereafter was ramped to the primary drying temperature (0° C.) under controlled pressure, and held at the primary drying temperature under controlled pressure for 1080 minutes. Following this, the temperature was ramped to the secondary drying temperature (25° C.) under controlled pressure, and held there under controlled pressure until drying was complete. At the end of the drying cycle the vials were stoppered under 150 mTorr, and then stored.

Samples were reconstituted in situ by addition of water. Reconstitution was assessed by visual inspection and UV absorbance, as described elsewhere herein. An $OD_{280}$ extinction coefficient of 1.14 was employed for a 1 mg/ml solution of etanercept to calculate the degree of reconstitution. Foam height was assessed by visual inspection and calibration using digital calipers, also as described elsewhere herein.

Stability of etanercept in the lyophilate was determined at several time points for storage at several temperatures. Stability was assessed for all samples by size exclusion high performance liquid chromatography ("SE-HPLC"). Briefly, 100 micrograms of each sample was denatured and reduced in guanidine HCl and DTT, and then alkylated with iodoacetamide. Approximately 30 micrograms of reduced and alkylated sample was analyzed on a tandem TosoHaas TSK G3000 SW×1 columns and eluted isocratically with 2.5 M guanidine-HCl, 100 mM sodium phosphate pH 6.5 at a flow rate of 0.6 ml/min for 45 minutes. Peaks were detected by absorbance at 215 nm. The amounts of fragments, intact monomers, and high molecular weight/misfolded proteins were calculated from the detected peak areas.

Representative results are depicted in FIG. 2, showing that etanercept prepared as described above is stable for extended periods of storage at both reduced and elevated temperatures.

Example 27

Use of Raman Spectroscopy to Determine Polymorphs

Mannitol polymorphs (crystalline alpha, beta and delta mannitol, mannitol hydrate and amorphous mannitol) were determined in etanercept formulations during lyophilization in real time by normalized second derivative Raman spectra using a Partial Least Squares ("PLS") algorithm (also referred to herein as "PLS Raman" and "PLS Raman Spectroscopy" and the like).

Raman spectra were acquired with a ChemImage Corporation FALCON II™ Molecular Chemical Imaging (MCI) Raman spectroscopy system, using a 532 nm excitation beam from a Spectra Physics Millennia II Laser Source laser. The sample was held in an Olympus Model BX51 microscope platform (see below). The excitation beam from the laser was focused on the sample through a 20× objective. The focused beam covered a circular area with a diameter of approximately 154 μm. Spectra were acquired through a grating with 300 grooves/mm, which provided a wide signal window for the Raman bands. Signals were detected on a back illuminated CCD (1340×100 pixels) operated at 40° C.

The sample was held in the stage in a Linkman Scientific Instruments, Ltd. FDCS 196 freeze drying cryostat ("cryostage") modified to couple it with the Raman spectroscopy system. The stage provided temperature and pressure control from, respectively, −196 to 125° C. and from 50 mTorr to 750 Torr. Raman spectra were acquired from samples in situ through a glass window in the top of the cryostage.

In brief, the method involves: obtaining a Raman spectrum for each polymorph over a broad range; normalizing the Raman spectra against their C—H stretch band at about 2800 $cm^{-1}$; deriving derivative spectra from the normalized spectra; computationally simulating a calibration set of spectra by linear addition of the normalized derivative spectra; generating a quantitation procedure using the Partial Least Squares algorithm and the calibration set; and then applying the procedure to the Raman spectrum of a sample to calculate the relative amounts of the polymorphs therein.

Figure 3:
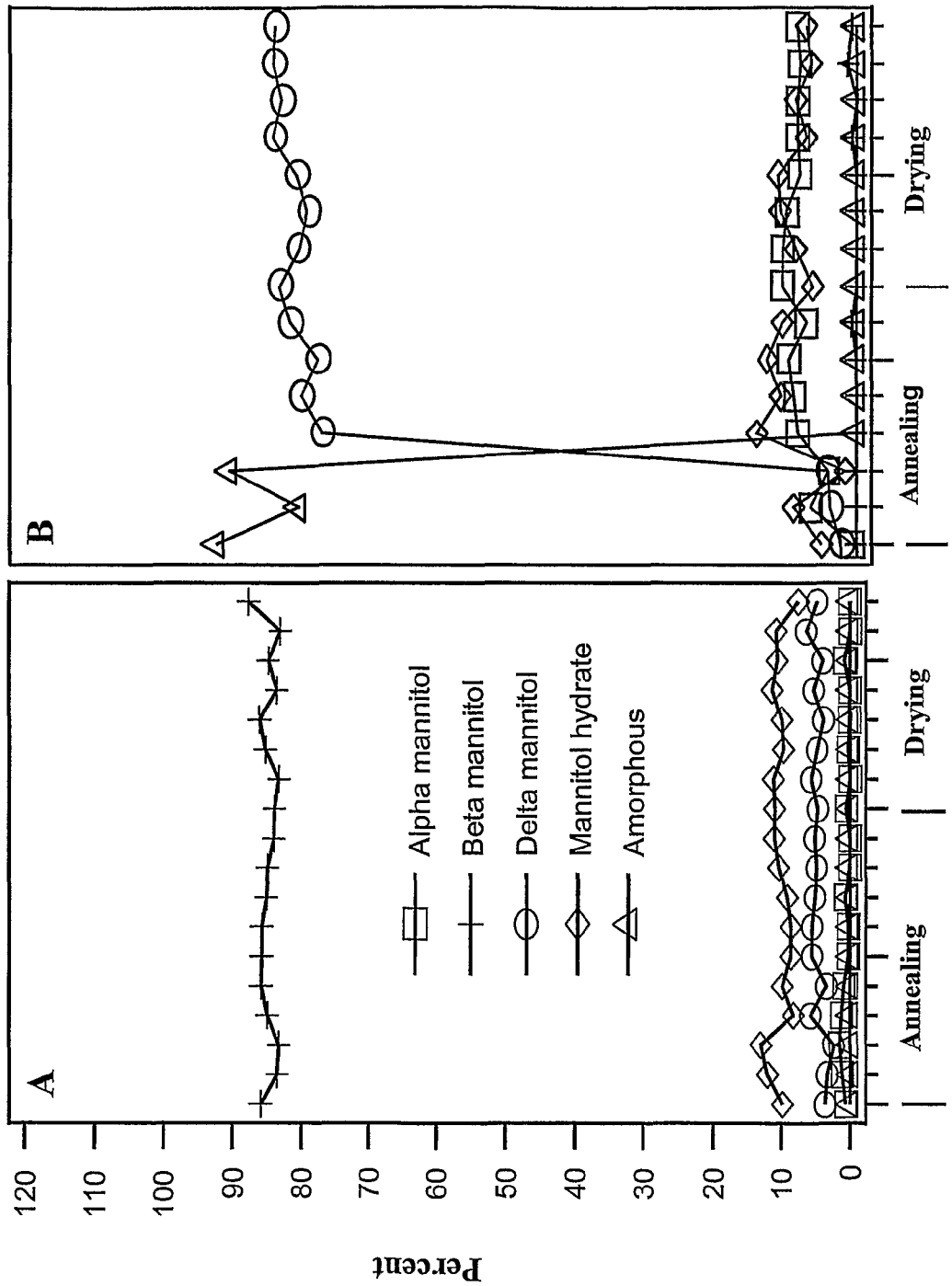
FIG. 3 is a graph showing the distribution of the mannitol polymorphs determined by in process PLS Raman Imaging Spectroscopy for lyophilization procedures that differ only in cooling rates: Panel (A) 1° C./min and Panel (B) 10° C./min. The percent of alpha, beta, and delta mannitol, mannitol hydrate and amorphous mannitol is shown over the course of annealing and drying steps, as indicated.

FIG. 3 illustrates the ability of the method to determine individually the five Mannitol polymorphs in real time under different lyophilization conditions.

Figure 6:
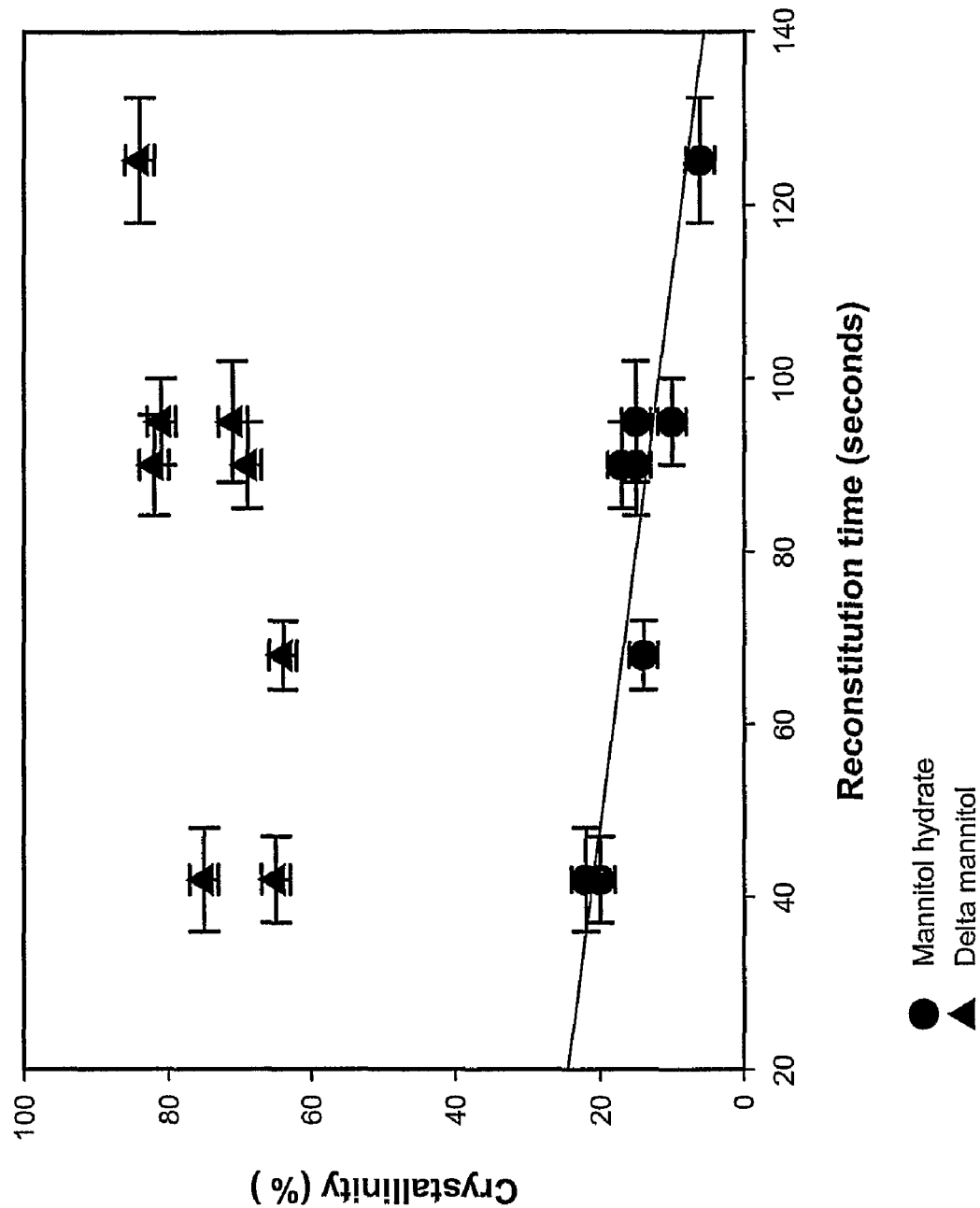
FIG. 6 is a graph showing the relationship between reconstitution time and the percent of mannitol polymorphs, particularly delta mannitol.

FIG. 6 shows the relationship between reconstitution time and both percent mannitol hydrate (circles) and percent delta mannitol (triangles) for several related formulations. Polymorphs were determined using the Raman method described above. Reconstitution times were determined as described elsewhere herein.

Figure 7:
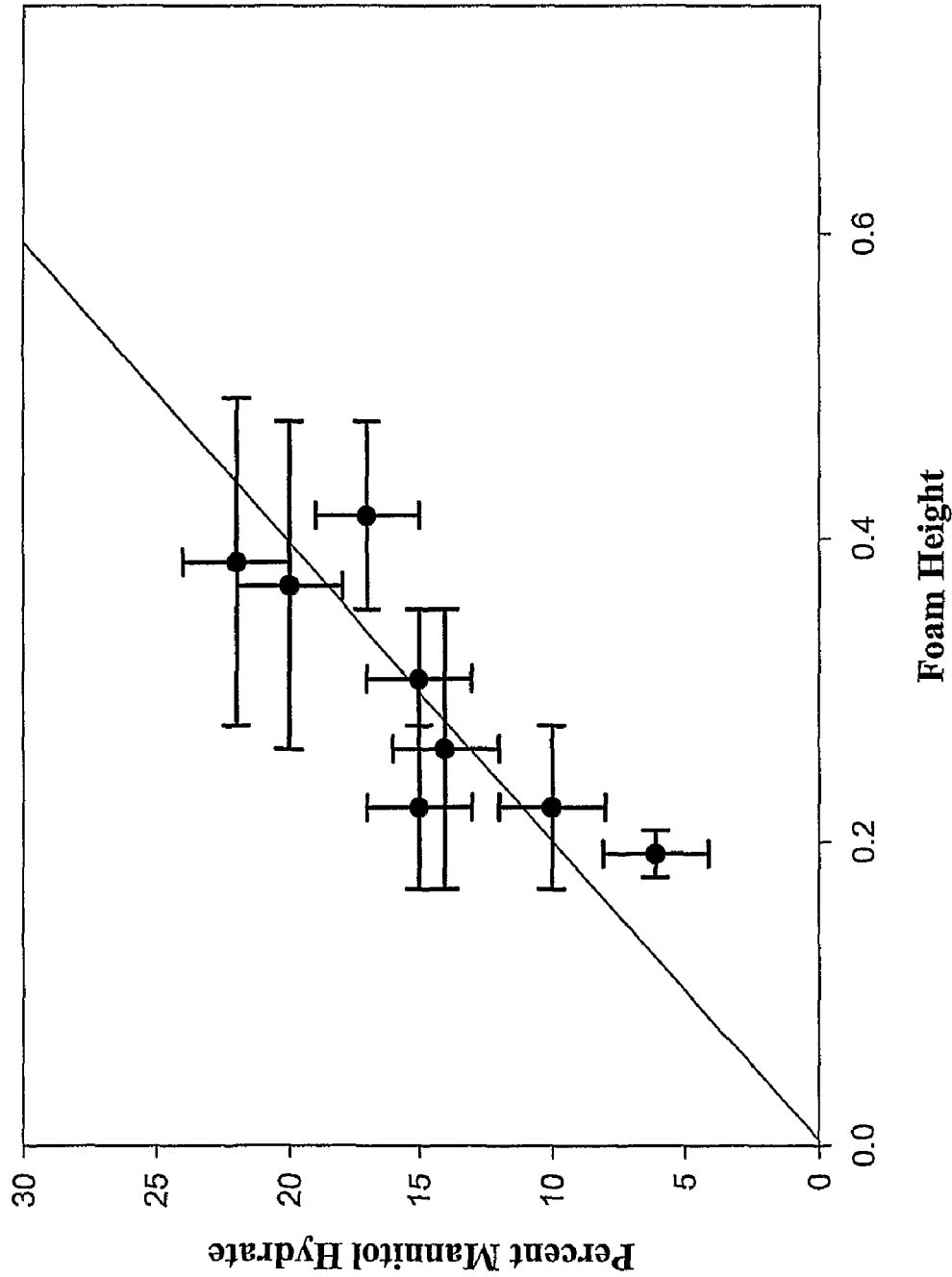
FIG. 7 is a graph showing the relationship between foam height and the percent of mannitol hydrate in the lyophilate.

FIG. 7 illustrates the relationship between foam height and percent mannitol hydrate for several related formulations. Mannitol hydrate percentages were determined by the Raman method described above. Foam heights were determined as described elsewhere herein.

As illustrated in this Example, the method is useful for, among a great many other things, real time imaging and quantification of the distribution of polymorphs in a sample during lyophilization, particularly for instance, for observing their crystallization and transformation during a lyophilization process.

Example 28

Etanercept Reconstitution and Foam Height as a Function of Mannitol Concentration at Two Annealing Temperatures Etanercept solutions containing several concentrations of mannitol were prepared, lyophilized, and reconstituted as described above. Reconstitution times and foam heights were determined in accordance with procedures described elsewhere herein. Results are depicted graphically in FIG. 4.

As seen in the graph, faster reconstitution times were observed for the samples annealed at −12° C. then for those annealed at −15° C. Reconstitution times for samples annealed at both temperatures remained the same from 2% to 2.5% mannitol. However, a sharp decrease in reconstitution time was observed at 2.5% to 2.6% mannitol for samples annealed at −12° C. annealing and at 2.4% to 2.5% mannitol for the samples annealed at −15° C. For both annealing conditions, reconstitution times plateau above 3.5% mannitol.

Foam heights for all samples were inversely proportional to reconstitution time.

What is claimed is:

1. A lyophilate comprising a protein and mannitol, wherein the mannitol is comprised of at least 70% delta mannitol, not more than 20% mannitol hydrate, and not more than 10% amorphous mannitol, wherein the surface area of the lyophilate is equal to or greater than 1.2 $m^2/g$.

2. A lyophilate according to claim 1, wherein the mannitol is comprised of at least 70% delta mannitol, not more than 10% amorphous mannitol, and not more than 20% mannitol hydrate plus alpha mannitol plus beta mannitol, wherein the surface area of the lyophilate is equal to or greater than 1.2 $m^2/g$.

3. A lyophilate according to claim 1 or 2 further comprising sucrose.

4. A lyophilate according to claim 1 or 2 further comprising a surfactant.

5. A lyophilate according to claim 4 wherein the surfactant is a polysorbate or Pluronic F68 or both.

6. A lyophilate according to claim 1 or 2 further comprising one or more of a stabilizing agent, a lyoprotectant, or a surfactant.

7. A lyophilate according to claim 1 or 2, wherein the protein is an antibody, or a variant, derivative, fragment, or mimetic thereof.

8. A lyophilate according to claim 7, wherein the antibody is a human or humanized antibody, or a variant, derivative, fragment, or mimetic thereof.

9. A lyophilate according to claim 8, wherein the antibody is a human or humanized antibody.

10. A lyophilate according to claim 1 or 2, wherein the protein comprises a region of a human or humanized antibody, or a variant, derivative, fragment, or mimetic thereof.

11. A lyophilate according to claim 10 wherein the region is a Fc region, or a variant, derivative, fragment, or mimetic thereof.

12. A lyophilate according to claim 11 wherein the region is a Fc region.

13. A lyophilate according to claim 1 or 2, wherein the protein is a fusion protein comprising a Fc region, or a variant, derivative, fragment, or mimetic thereof; and a ligand-binding moiety of a ligand binding protein, or a variant, derivative, fragment, or mimetic thereof.

14. A lyophilate according to claim 13 wherein the protein is a fusion protein comprising a Fc region and a ligand-binding moiety of a ligand binding protein.

15. A lyophilate according to claim 13 wherein the ligand binding moiety is a TNF binding moiety of a TNF receptor, or a variant, derivative, fragment, or mimetic thereof; or an IL-1 binding moiety of a protein ligand of an IL-1 receptor, or a variant, derivative, fragment, or mimetic thereof.

16. A lyophilate according to claim 1 or 2, wherein the protein is a peptibody.

* * * * *